United States Patent
Drummond et al.

(10) Patent No.: US 12,194,034 B2
(45) Date of Patent: Jan. 14, 2025

(54) NEUTROPHIL EXOCYTOSIS INHIBITORS

(71) Applicant: IMMUNYX PHARMA LTD., Jerusalem (IL)

(72) Inventors: Daryl C. Drummond, Lincoln, MA (US); Seth Jonah Salpeter, Jerusalem (IL)

(73) Assignee: IMMUNYX PHARMA LTD., Jerusalem (IL)

( * ) Notice: Subject to any disclaimer, the term of this patent is extended or adjusted under 35 U.S.C. 154(b) by 0 days.

(21) Appl. No.: 18/617,768

(22) Filed: Mar. 27, 2024

(65) Prior Publication Data

US 2024/0293390 A1    Sep. 5, 2024

Related U.S. Application Data

(63) Continuation of application No. PCT/IL2022/051340, filed on Dec. 15, 2022.

(60) Provisional application No. 63/289,771, filed on Dec. 15, 2021.

(51) Int. Cl.
| | |
|---|---|
| *A61K 31/4545* | (2006.01) |
| *A61K 9/107* | (2006.01) |
| *A61K 9/127* | (2006.01) |
| *A61K 9/50* | (2006.01) |
| *A61K 31/4196* | (2006.01) |
| *A61K 31/454* | (2006.01) |
| *A61K 47/64* | (2017.01) |
| *A61K 47/69* | (2017.01) |
| *A61P 35/00* | (2006.01) |
| *C07D 249/08* | (2006.01) |
| *C07D 401/06* | (2006.01) |
| *C07D 401/10* | (2006.01) |
| *C07D 401/14* | (2006.01) |

(52) U.S. Cl.
CPC ........ *A61K 31/4545* (2013.01); *A61K 9/1075* (2013.01); *A61K 9/127* (2013.01); *A61K 9/5015* (2013.01); *A61K 31/4196* (2013.01); *A61K 31/454* (2013.01); *A61K 47/64* (2017.08); *A61K 47/6925* (2017.08); *A61P 35/00* (2018.01); *C07D 249/08* (2013.01); *C07D 401/06* (2013.01); *C07D 401/10* (2013.01); *C07D 401/14* (2013.01)

(58) Field of Classification Search
CPC .. A61K 31/4545; A61K 9/1075; A61K 9/127; A61K 9/5015; A61K 31/4196; A61K 31/454; A61K 47/64; A61K 47/6925; A61P 35/00; C07D 249/08; C07D 401/06; C07D 401/10; C07D 401/14

See application file for complete search history.

(56) References Cited

FOREIGN PATENT DOCUMENTS

| | | |
|---|---|---|
| CN | 105859696 A | 8/2016 |
| EP | 0053325 A1 | 6/1982 |
| WO | 2022003674 A1 | 1/2022 |

OTHER PUBLICATIONS

Stingaci E, Zveaghinteva M, Pogrebnoi S, Lupascu L, Valica V, Uncu L, Smetanscaia A, Drumea M, Petrou A, Ciric A, Glamoclija J, Sokovic M, Kravtsov V, Geronikaki A, Macaev F. New vinyl-1,2,4-triazole derivatives as antimicrobial agents: Synthesis, biological evaluation and molecular docking studies. Bioorg Med Chem Lett. Sep. 1, 2020;30(17):127368. doi: 10.1016/j.bmcl.2020. 127368. Epub Jun. 26, 2020. PMID: 32738986.

Ruan, Y. et al. (2011). Synthesis and antifungal activity of new 1-(2,4-dichloro phenyl)-3-aryl-2-(1H-1,2,4-triazol-1-yl) prop-2-en-1-one derivatives. African Journal of Pharmacy and Pharmacology. 5. 602-607. 10.5897/AJPP11.080.

Johnson JL, Ramadass M, He J, Brown SJ, Zhang J, Abgaryan L, Biris N, Gavathiotis E, Rosen H, Catz SD. Identification of Neutrophil Exocytosis Inhibitors (Nexinhibs), Small Molecule Inhibitors of Neutrophil Exocytosis and Inflammation: Druggability of the Small GTPase Rab27a. J Biol Chem. Dec. 9, 2016;291(50):25965-25982. doi: 10.1074/jbc.M116.741884. Epub Oct. 4, 2016. PMID: 27702998; PMCID: PMC5207069.

Vols S, Kaisar-Iluz N, Shaul ME, Ryvkin A, Ashkenazy H, Yehuda A, Atamneh R, Heinberg A, Ben-David-Naim M, Nadav M, Hirsch S, Mitesser V, Salpeter SJ, Dzikowski R, Hayouka Z, Gershoni JM, Fridlender ZG, Granot Z. Targeted nanoparticles modify neutrophil function in vivo. Front Immunol. Oct. 5, 2022;13:1003871. doi: 10.3389/fimmu.2022.1003871. PMID: 36275643; PMCID: PMC9580275.

Gupta et al. High-Throughput Real-Time Imaging Technique To Quantify NETosis and Distinguish Mechanisms of Cell Death in Human Neutrophils. J Immunol. Jan. 15, 2018;200(2):869-879. doi: 10.4049/jimmunol.1700905. Epub Dec. 1, 2017. PMID: 29196457; PMCID: PMC5760330.

PCT International Search Report for International Application No. PCT/IL2022/051340, mailed Apr. 4, 2023, 5pp.

PCT Written Opinion for International Application No. PCT/IL2022/051340, mailed Apr. 4, 2023, 9pp.

*Primary Examiner* — John M Mauro
(74) *Attorney, Agent, or Firm* — The Roy Gross Law Firm, LLC; Roy Gross

(57) ABSTRACT

The present invention is directed to compounds and compositions comprising thereof. Further, methods of use such as for the treatment and prevention of a neutrophil-associated disease or condition in a subject in need thereof are also provided.

20 Claims, 19 Drawing Sheets
Specification includes a Sequence Listing.

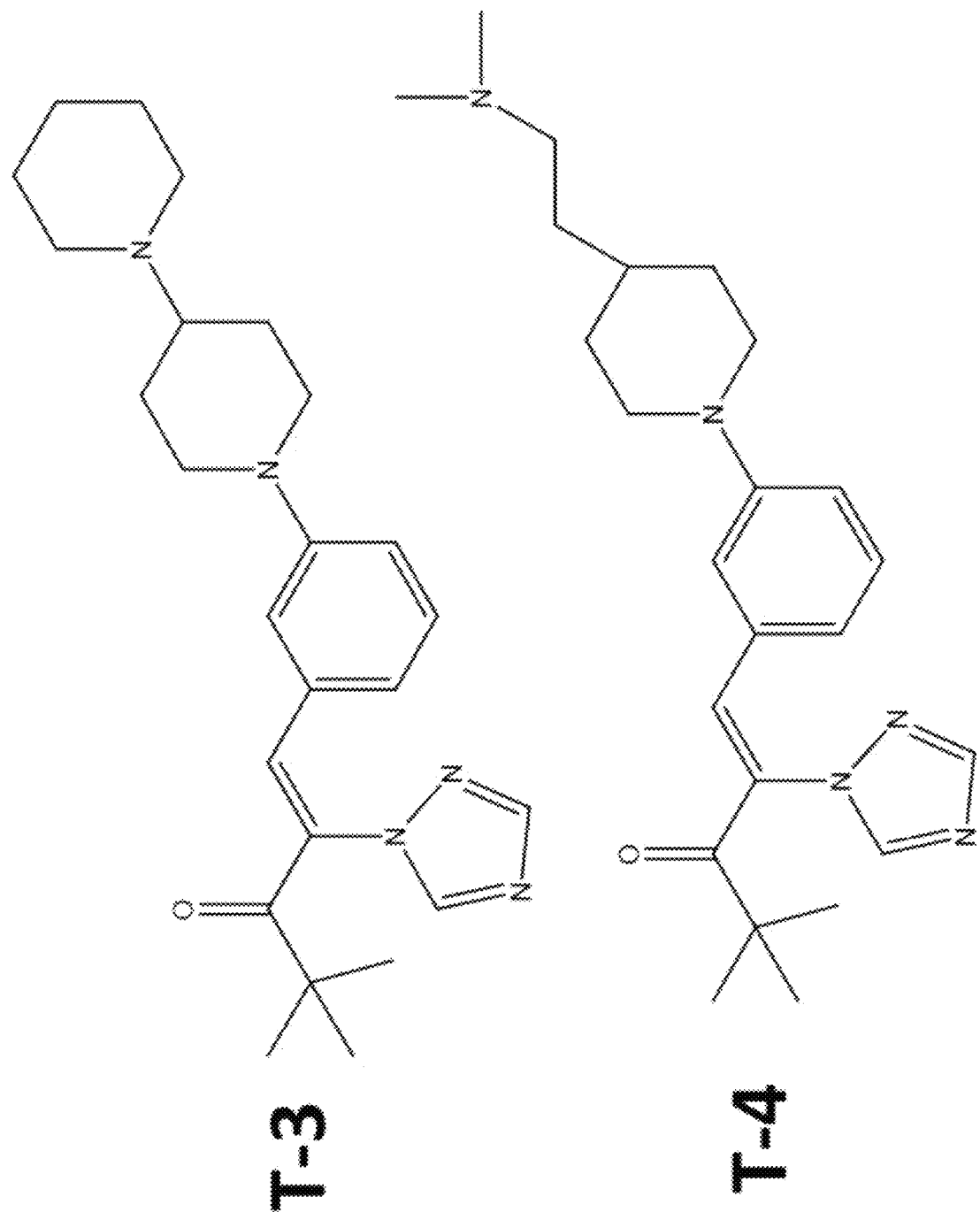
Figure 1_continued

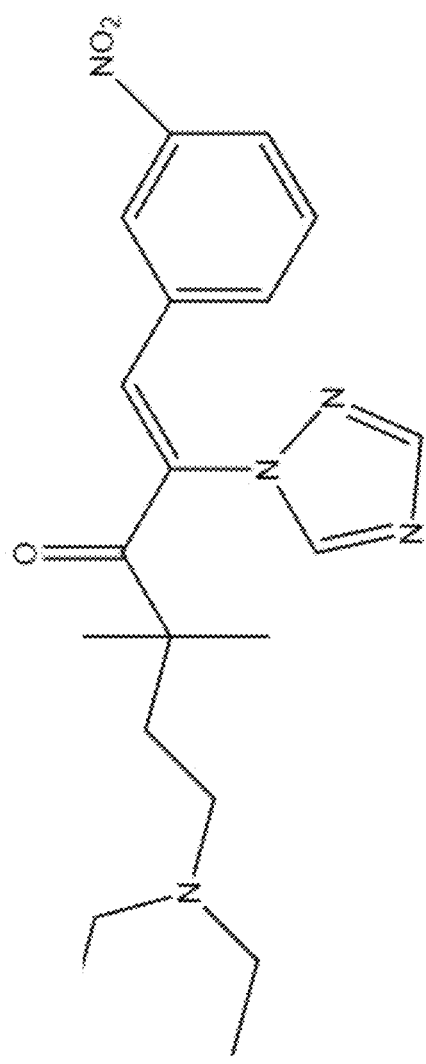
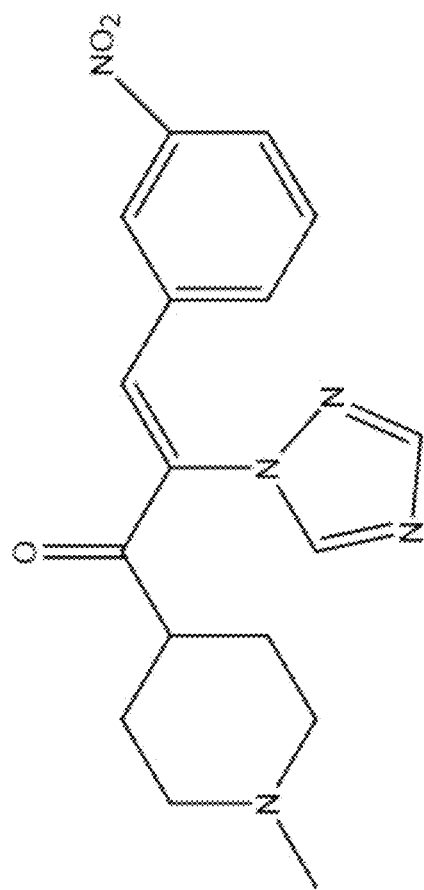
Figure 1_continued_1

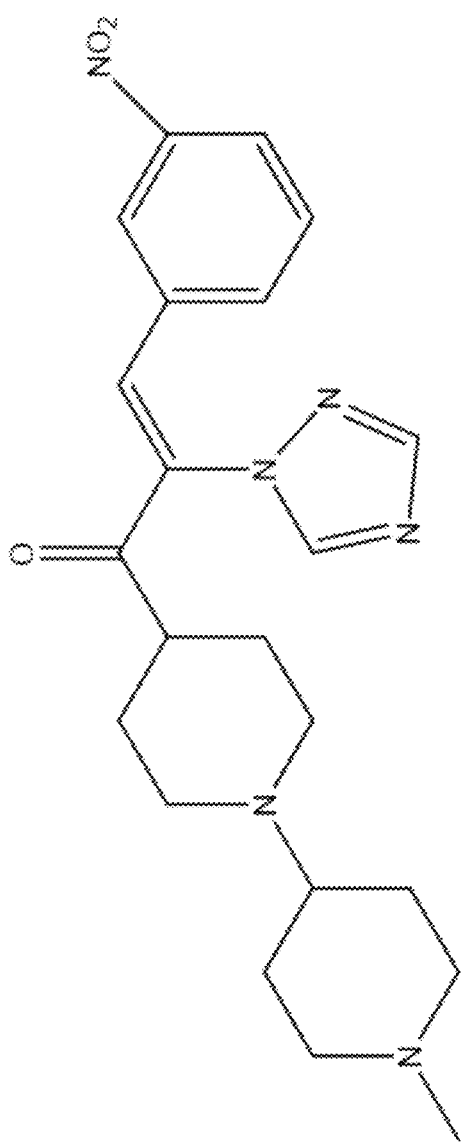
Figure 1_continued_2

SEQUENCE LISTING

```
Sequence total quantity: 14
SEQ ID NO: 1            moltype = AA  length = 15
FEATURE                 Location/Qualifiers
source                  1..15
                        mol_type = protein
                        organism = synthetic construct
SEQUENCE: 1
KFPDLDSRRL PHMSL                                                   15

SEQ ID NO: 2            moltype = AA  length = 12
FEATURE                 Location/Qualifiers
source                  1..12
                        mol_type = protein
                        organism = synthetic construct
SEQUENCE: 2
LATTHMVFSP DH                                                      12

SEQ ID NO: 3            moltype = AA  length = 13
FEATURE                 Location/Qualifiers
source                  1..13
                        mol_type = protein
                        organism = synthetic construct
SEQUENCE: 3
PSSNLESTPL SLL                                                     13
```

```
SEQ ID NO: 4            moltype = AA   length = 13
FEATURE                 Location/Qualifiers
source                  1..13
                        mol_type = protein
                        organism = synthetic construct
SEQUENCE: 4
SSLMTTQLIA TSI                                                          13

SEQ ID NO: 5            moltype = AA   length = 12
FEATURE                 Location/Qualifiers
source                  1..12
                        mol_type = protein
                        organism = synthetic construct
SEQUENCE: 5
PELDSKPYFP PL                                                           12

SEQ ID NO: 6            moltype = AA   length = 12
FEATURE                 Location/Qualifiers
source                  1..12
                        mol_type = protein
                        organism = synthetic construct
SEQUENCE: 6
ELVTASMPRP NN                                                           12

SEQ ID NO: 7            moltype = AA   length = 12
FEATURE                 Location/Qualifiers
source                  1..12
                        mol_type = protein
                        organism = synthetic construct
SEQUENCE: 7
SLESSPMAQL PQ                                                           12

SEQ ID NO: 8            moltype = AA   length = 12
FEATURE                 Location/Qualifiers
source                  1..12
                        mol_type = protein
                        organism = synthetic construct
SEQUENCE: 8
SELRSTPLLV PS                                                           12

SEQ ID NO: 9            moltype = AA   length = 10
FEATURE                 Location/Qualifiers
source                  1..10
                        mol_type = protein
                        organism = synthetic construct
SEQUENCE: 9
LQIQSWSSSP                                                              10

SEQ ID NO: 10           moltype = AA   length = 10
FEATURE                 Location/Qualifiers
source                  1..10
                        mol_type = protein
                        organism = synthetic construct
SEQUENCE: 10
STMTILGTGS                                                              10

SEQ ID NO: 11           moltype = AA   length = 12
FEATURE                 Location/Qualifiers
source                  1..12
                        mol_type = protein
                        organism = synthetic construct
SEQUENCE: 11
TETSLRIVST NP                                                           12

SEQ ID NO: 12           moltype = AA   length = 12
FEATURE                 Location/Qualifiers
source                  1..12
                        mol_type = protein
                        organism = synthetic construct
SEQUENCE: 12
LSIVSGSALN HL                                                           12

SEQ ID NO: 13           moltype = AA   length = 10
FEATURE                 Location/Qualifiers
source                  1..10
                        mol_type = protein
                        organism = synthetic construct
SEQUENCE: 13
LTLVSERPMI                                                              10
```

```
SEQ ID NO: 14        moltype = AA  length = 11
FEATURE              Location/Qualifiers
source               1..11
                     mol_type = protein
                     organism = synthetic construct
SEQUENCE: 14
LQIQSWSSSP C                                                          11
```

NEUTROPHIL EXOCYTOSIS INHIBITORS

CROSS-REFERENCE TO RELATED APPLICATIONS

This application is a Continuation of PCT Application No. PCT/IL2022/051340, filed on 15 Dec. 2022 which claims the benefit of priority of U.S. Provisional Patent Application No. 63/289,771 filed Dec. 15, 2021, the contents of which are incorporated herein by reference in their entirety.

REFERENCE TO AN ELECTRONIC SEQUENCE LISTING

The contents of the electronic sequence listing (IMUX-P-003-PCT SQL.xml; Size: 12,970 bytes; and Date of Creation: Dec. 11, 2022) is herein incorporated by reference in its entirety.

FIELD OF THE INVENTION

The present invention is in the field of neutrophil pathology.

BACKGROUND OF THE INVENTION

Neutrophils are potent effector cells in a wide range of infectious, inflammatory and autoimmune conditions as well as cancer. In certain instances, the neutrophils' natural role as cytotoxic, inflammation causing cells can have adverse consequences. Uncontrolled neutrophil secretion represents a major hazard. Diseases characterized by excessive neutrophil-mediated tissue damage require therapeutics that can temporarily inhibit the neutrophils effector functions, but without causing neutrophil cell death and neutropenia. Therapeutics that can balance the need to inhibit effector function while not killing neutrophils are greatly needed.

SUMMARY OF THE INVENTION

The present invention provides a compound represented by any one of the formulas disclosed herein. Compositions comprising the compound and nanoparticles comprising the compound are also provided. Methods of treating neutrophil-associated diseases or conditions are also provided.

According to a first aspect, there is provided a compound represented by any one of the formulas provided herein.

According to another aspect, there is provided a compound including any stereoisomer or a salt thereof, wherein the compound is represented by Formula I:

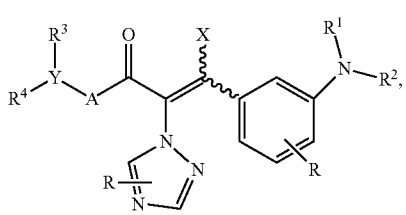

(I)

or by Formula:

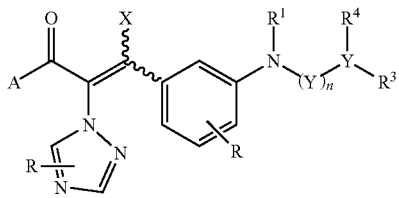

wherein:
A represents a methyl group, isopropyl group, tert-butyl group, a linear or branched $C_1$-$C_{10}$ alkyl group, a linear or branched $C_2$-$C_{10}$ alkyl group substituted or not substituted, a substituted $C_2$-$C_{10}$ alkyl group, optionally substituted $C_3$-$C_{10}$ cycloalkyl group comprising one or more carbocyclic rings, an optionally substituted $C_2$-$C_{10}$ alkyl group comprising one or more heteroatom(s), a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof;

Y is absent or is selected from the group consisting of N, NH, $NR^1$, CH, $HCR^1$, $CH_2$, S, SH, and O;

n is an integer between 0 and 5;

X is hydrogen or represents a substituent selected from the group consisting of: a halo group, a methyl group, isopropyl group, $C_2$-$C_{10}$ alkyl group, a substituted $C_2$-$C_{10}$ alkyl group, an alkoxy group, an amino group, and a hydroxy group;

each R independently is absent or represents one or more substituents each independently comprising any one of a methyl group, isopropyl group, $C_2$-$C_{10}$ alkyl group, a substituted $C_2$-$C_{10}$ alkyl group, halo, oxo, —$NO_2$, amino, hydroxy, —CN, —OH, -$CONH_2$, —$CONR'_2$, —$CNNR'_2$, —$CSNR'_2$, —CONH—OH, —CONH—$NH_2$, —NHCOR, —NHCSR, —NHCNR, —NC(=O)OR, —NC(=O)NR', —NC(=S)OR', —NC(=S)NR', —$SO_2R'$, —SOR', —SR', —$SO_2OR'$, —$SO_2N(R')_2$, —$NHNR'_2$, —NNR', $C_1$-$C_6$ haloalkyl, optionally substituted $C_1$-$C_6$ alkyl, —$NH_2$, —NR'R', —NH($C_1$-$C_6$ alkyl), —N($C_1$-$C_6$ alkyl)$_2$, $C_1$-$C_6$ alkoxy, $C_1$-$C_6$ haloalkoxy, hydroxy ($C_1$-$C_6$ alkyl), hydroxy ($C_1$-$C_6$ alkoxy), alkoxy ($C_1$-$C_6$ alkyl), alkoxy ($C_1$-$C_6$ alkoxy), $C_1$-$C_6$ alkyl-$NR'_2$, $C_1$-$C_6$ alkyl-SR', —CONH($C_1$-$C_6$ alkyl), —CON($C_1$-$C_6$ alkyl)$_2$, —$CO_2H$, —$CO_2R'$, —OCOR, —OCOR', —OC(=O)OR', —OC(=O)NR', —OC(=S)OR', —OC(=S)NR', —OR', —NR'R', or a combination thereof; wherein each R' independently represents hydrogen, or is selected from the group comprising optionally substituted $C_1$-$C_{10}$ alkyl, optionally substituted $C_3$-$C_{10}$ cycloalkyl, optionally substituted $C_3$-$C_{10}$ heterocyclyl, optionally substituted heteroaryl, optionally substituted aryl, amino, hydroxy, halo, oxo, cyano, optionally substituted $C_1$-$C_{10}$ alkyl, or any combination thereof as allowed by valency; $R^1$ and $R^2$ are each independently selected from the group comprising hydrogen, oxygen, $C_1$-$C_{20}$ alkyl group, optionally substituted linear or branched $C_1$-$C_{20}$ aminoalkyl group, optionally substituted linear, branched or cyclic $C_1$-$C_{20}$ alkyl group optionally comprising one or more heteroatom(s), a substituted $C_1$-$C_{20}$ alkyl group, a $C_1$-$C_{20}$ haloalkyl group, a substituted $C_1$-$C_{20}$ haloalkyl group, an aliphatic linear or branched $C_3$-$C_{20}$ aminoalkyl group optionally comprising one or more heterocyclic ring(s), or wherein $R^1$ and Y are interconnected so as to form an optionally substituted 4 to 8-membered ring, or wherein $R^1$ and $R^2$ are interconnected so as to form an optionally substituted 4 to 8-membered ring optionally comprising one or more heteroatoms, or any combination thereof;

$R^3$ is hydrogen, or is absent, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a thioalkoxy group, a thioalkyl group, a hydroxy group, a mercapto group, an allyl group, $C_1$-$C_{10}$ ether group, a vinyl group, a cyano group, a nitro group, a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^3$ and A are interconnected so as to form an optionally substituted 4 to 8-membered ring; or $R_3$ and Y are interconnected so as to form an optionally substituted 4 to 8-membered ring and $R^4$ is absent, hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof, or wherein $R^3$ and $R^4$ are interconnected so as to form an optionally substituted 4 to 8-membered ring.

According to some embodiments, if $R^1$ and $R^2$ is oxygen, then Y is N.

According to some embodiments, the compound is represented by Formula IIa:

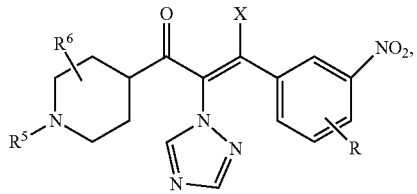

(IIa)

or Formula IIb:

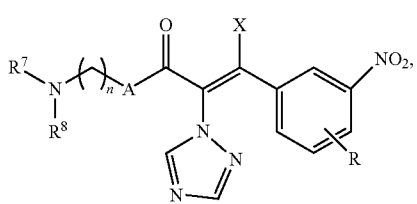

(IIb)

wherein:

$R^5$ and $R^6$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or any combination thereof;

n is an integer ranging between 0 and 5; and $R^7$ and $R^8$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^7$ and $R^8$ are interconnected so as to form an optionally substituted 4 to 8-membered ring.

According to some embodiments, the compound is represented by Formula IIIa:

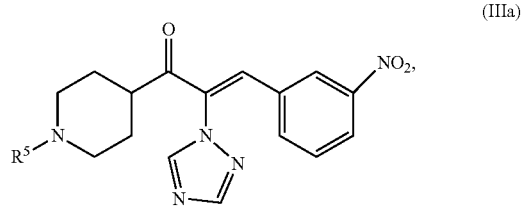

(IIIa)

or Formula IIIb:

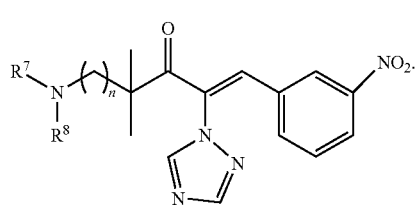

(IIIb)

According to some embodiments, the compound is represented by Formula:

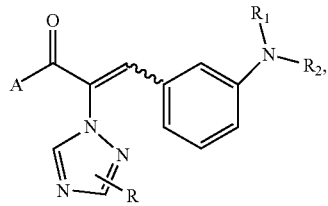

wherein A is selected from the group comprising a methyl group, isopropyl group, tert-butyl group, a linear or branched $C_1$-$C_{10}$ alkyl group, optionally substituted $C_3$-$C_{10}$ cycloalkyl group comprising one or more carbocyclic rings, a linear or branched $C_2$-$C_{10}$ alkyl group, a linear or branched substituted $C_2$-$C_{10}$ alkyl group, $R^1$ and $R^2$ are each independently selected from the group comprising hydrogen, optionally substituted linear, branched or cyclic $C_1$-$C_{20}$ alkyl group optionally comprising one or more nitrogen atom(s); an optionally substituted $C_1$-$C_{20}$ alkyl group; an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; or wherein $R^1$ and $R^2$ are interconnected so as to form one or more 4 to 8-membered ring(s) optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group, or any combination thereof; and wherein at least one of $R^1$ and $R^2$ is any one of branched or cyclic $C_1$-$C_{20}$ alkyl group comprising one or more nitrogen atom(s); an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group.

According to some embodiments, the compound is represented by Formula IVa:

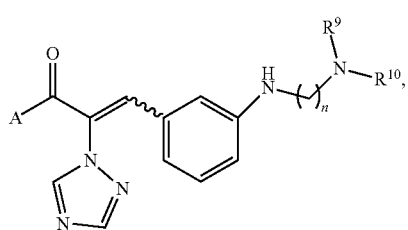

or Formula IVb:

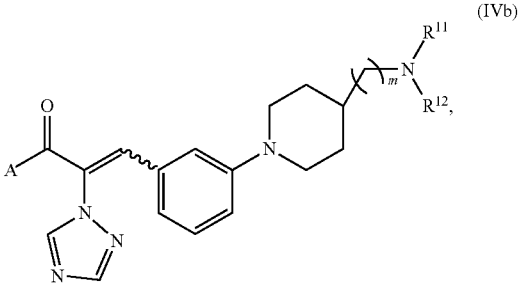

wherein:

$R^9$ and $R^{10}$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof; or $R^9$ and $R^{10}$ are interconnected so as to form one or more optionally substituted 4 to 8-membered ring(s);

m is an integer ranging between 0 and 7; and $R^{11}$ and $R^{12}$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group, a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^{11}$ and $R^{12}$ are interconnected so as to form an optionally substituted 4 to 8-membered ring.

According to some embodiments, the compound is represented by Formula:

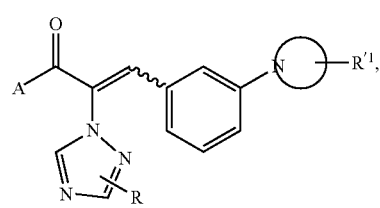

or by Formula:

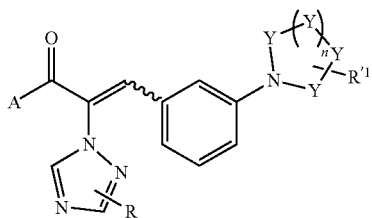

wherein n is 1-3; wherein each Y is independently CHR'¹ or NR'¹; and wherein R'¹ is absent or represents one or more substituents each independently selected from the group comprising an optionally substituted linear, branched or cyclic $C_1$-$C_{20}$ alkyl group optionally comprising one or more nitrogen atom(s); an optionally substituted $C_1$-$C_{20}$ alkyl group; an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; halo, oxo, —NO$_2$, amino, hydroxy, —CN, —OH, —CONH$_2$, —CONR'$_2$, —CNNR'$_2$, —CSNR'$_2$, —CONH—OH, —CONH—NH$_2$, —NHCOR, —NHCSR, —NHCNR, —NC(=O)OR, —NC(=O)NR', —NC(=S)OR', —NC(=S)NR', —SO$_2$R', —SOR', —SR', —SO$_2$OR', —SO$_2$N(R')$_2$, —NHNR'$_2$, —NNR', $C_1$-$C_6$ haloalkyl, optionally substituted $C_1$-$C_6$ alkyl, —NH$_2$, —NR'R', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy ($C_1$-$C_6$ alkoxy), alkoxy($C_1$-$C_6$ alkyl), alkoxy($C_1$-$C_6$ alkoxy), $C_1$-$C_6$ alkyl-NR'$_2$, $C_1$-$C_6$ alkyl-SR', —CONH($C_1$-$C_6$ alkyl), —CON($C_1$-$C_6$ alkyl)$_2$, —CO$_2$H, —CO$_2$R', —OCOR, —OCOR', —OC(=O)OR', —OC(=O)NR', —OC(=S) OR', —OC(=S)NR', —OR', —NR'R', or a combination thereof; wherein each R' independently represents hydrogen, or is selected from the group comprising optionally substituted $C_1$-$C_{10}$ alkyl, optionally substituted $C_3$-$C_{10}$ cycloalkyl, optionally substituted $C_3$-$C_{10}$ heterocyclyl, optionally substituted heteroaryl, optionally substituted aryl, amino, hydroxy, halo, oxo, cyano, optionally substituted $C_1$-$C_{10}$ alkyl, or a combination thereof.

According to some embodiments, A is tert-butyl.

According to some embodiments, the compound is represented by Formula:

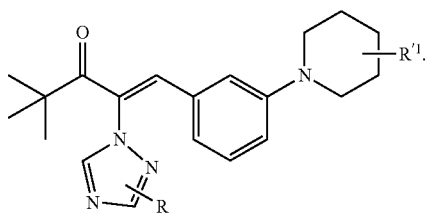

According to some embodiments, R'¹ is absent or represents one or more substituents each independently selected from the group comprising an optionally substituted cyclic $C_5$-$C_6$ aliphatic ring comprising one or more nitrogen atom(s); an optionally substituted linear, branched or cyclic $C_1$-$C_{20}$ alkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; halo, oxo, —NO$_2$, amino, hydroxy, —CN, —OH, —CONH$_2$.

According to some embodiments, R'¹ is an optionally substituted cyclic $C_5$-$C_6$ aliphatic ring comprising one or more nitrogen atom(s); and wherein the optionally substituted cyclic $C_5$-$C_6$ aliphatic ring is bound via a nitrogen atom.

According to some embodiments, the compound is selected from the group consisting of:

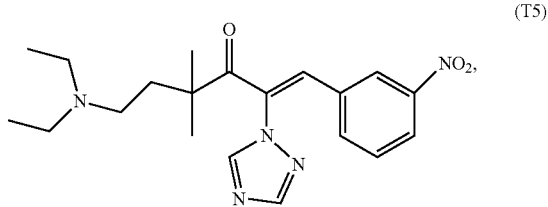

(T5)

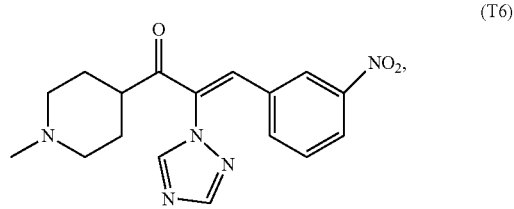

(T6)

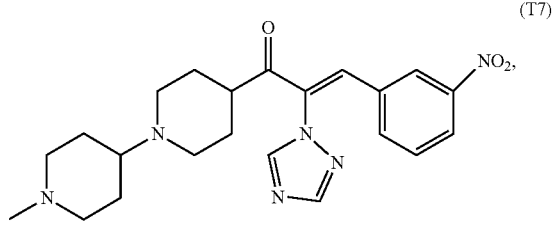

(T7)

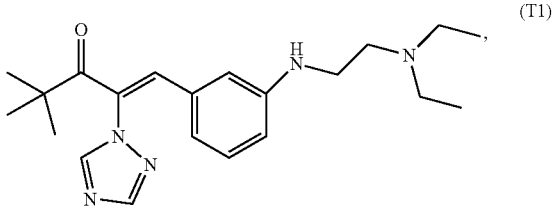

(T1)

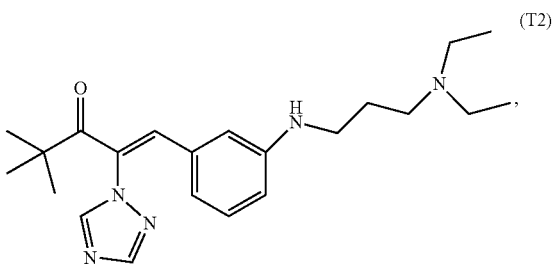

(T2)

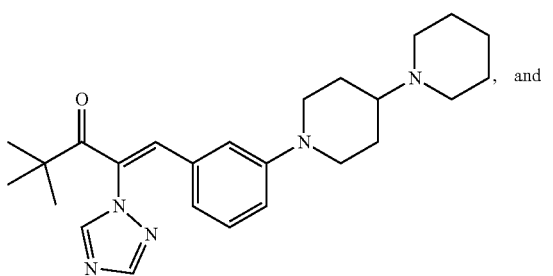

(T3)

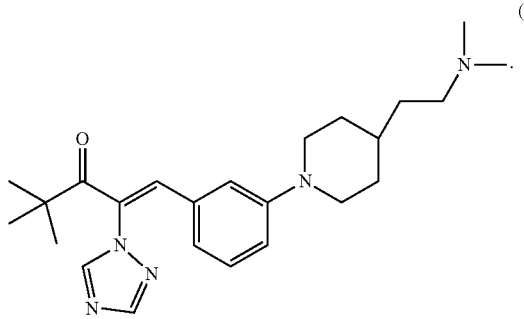

(T4)

According to some embodiments, the compound is selected from the group consisting of T1, T3 and T4 including any cis-, or trans-isomer thereof. According to some embodiments, the compound is selected from the group consisting of T1, T3 and T4.

According to some embodiments, the compound is T3.

According to some embodiments, the compound is a Z-isomer.

According to another aspect, there is provided a nanoparticle comprising a core and a shell, wherein the shell comprises a lipid layer, and the core comprises the compound of the present invention.

According to some embodiments, the lipid layer comprises, a phospholipid and a sterol.

According to some embodiments, the nanoparticle is in a form of liposome or micelle.

According to some embodiments, the nanoparticle is characterized by a size of between 50 nanometers (nm) and 500 nm.

According to some embodiments, the nanoparticle further comprises a peptide comprising an amino acid sequence selected from SEQ ID NO: 1-13.

According to some embodiments, the nanoparticle comprises SEQ ID NO: 9.

According to some embodiments, the peptide is conjugated to an 8-amino-3,6-dioxaoctanoic acid (Doa) residue.

According to some embodiments, the nanoparticle comprises a peptide multimer comprising a branched scaffold comprising at least 4 peptides comprising an amino acid sequence selected from SEQ ID NO: 1-13.

According to some embodiments, the peptide is attached to the outside of the shell.

According to some embodiments, the peptide is covalently conjugated to the outside of the shell.

According to some embodiments, the peptide further comprises a C-terminal cysteine residue that is conjugated to a maleimide in the shell by a thiol-maleimide reaction.

According to another aspect, there is provided a pharmaceutical composition, comprising the compound of the present invention, or the nanoparticle of the present invention, and a pharmaceutically acceptable carrier.

According to some embodiments, the pharmaceutical composition is for use in treating a neutrophil-associated disease or condition.

According to some embodiments, the pharmaceutical composition is for use in treating a disease or condition associated with accumulation of neutrophils to a diseased or injured tissue or site.

According to some embodiments, the disease or condition is selected from the group consisting of: a cancer, an inflammatory disease or condition and an inflammatory autoimmune disease or condition.

According to some embodiments, the disease or condition is an inflammatory disease or condition.

According to some embodiments, the inflammatory disease or condition is selected from chronic obstructive pulmonary disease (COPD), inflammatory bowel disease (IBD), peritonitis and an inflammatory skin disorder or disease.

According to some embodiments, the inflammatory disease or condition is IBD.

According to some embodiments, the disease or condition is cancer.

According to some embodiments, the cancer is selected from the group consisting of: kidney cancer, hepatocellular carcinoma (HCC), and head and neck squamous cell carcinoma (HNSCC).

According to some embodiments, the cancer is kidney cancer. According to some embodiments, the kidney cancer comprises renal cell carcinoma (RCC).

According to some embodiments, the composition is formulated for at least one of: systemic administration, intravenous administration, subcutaneous administration, topical administration, rectal administration, oral administration, intratumoral administration and local administration to a site of inflammation.

According to another aspect, there is provided a method of treating a neutrophil-associated disease or condition in a subject in need thereof, the method comprising administering to the subject the pharmaceutical composition of the present invention.

According to some embodiments, the disease or condition is selected from the group consisting of: a cancer, an inflammatory disease or condition and an inflammatory autoimmune disease or condition.

According to some embodiments, the disease or condition is an inflammatory disease or condition.

According to some embodiments, the inflammatory disease or condition is selected from COPD, IBD and peritonitis.

According to some embodiments, the inflammatory disease or condition is IBD.

According to some embodiments, the disease or condition is cancer. According to some embodiments, the cancer is kidney cancer.

According to some embodiments, the disease or condition is an inflammatory skin condition.

According to some embodiments, the administering comprises any one of: systemic administration, intravenous administration, subcutaneous administration, topical administration, rectal administration, oral administration, intratumoral administration and local administration to a site of inflammation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

By a first aspect, there is provided a compound represented by any one of Formula I to Formula IVb as described herein.

Figure 1:
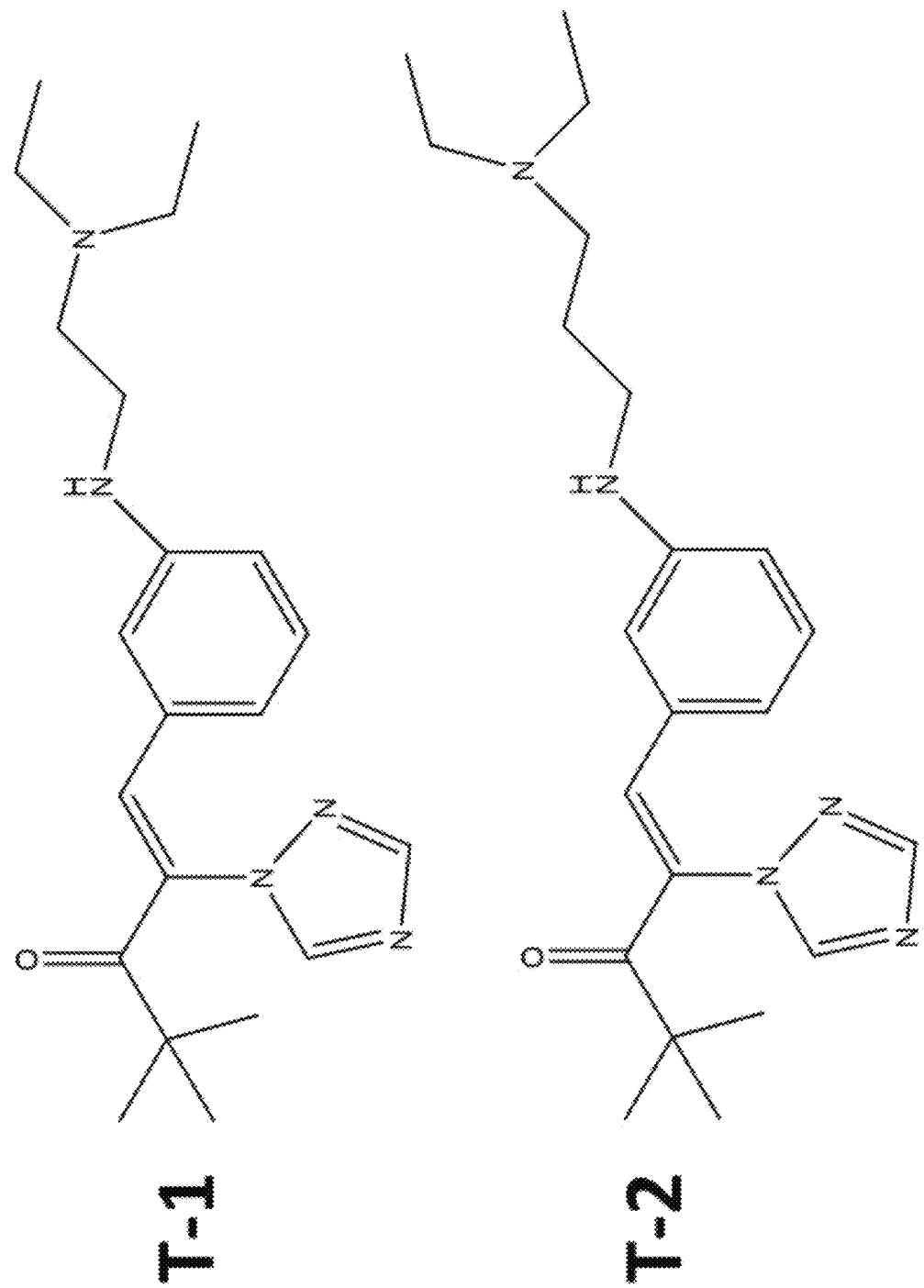
FIG. 1: Images of the chemical structures of the compounds T1 to T7.

By another aspect, there is provided a compound represented by Formula I as described herein. By another aspect, there is provided a compound represented by Formula II as described herein. By another aspect, there is provided a compound represented by Formula IIa as described herein. By another aspect, there is provided a compound represented by Formula IIb as described herein. By another aspect, there is provided a compound represented by Formula III as described herein. By another aspect, there is provided a compound represented by Formula IIIa as described herein. By another aspect, there is provided a compound represented by Formula IIIb as described herein. By another aspect, there is provided a compound represented by Formula IIIc as described herein. By another aspect, there is provided a compound represented by Formula IV as described herein. By another aspect, there is provided a compound represented by Formula IVa as described herein. By another aspect, there is provided a compound represented by Formula IVb as described herein. By another aspect, there is provided a compound provided in FIG. 1.

By another aspect, there is provided a nanoparticle comprising a compound of the invention.

By another aspect, there is provided a composition comprising a compound of the invention. By another aspect, there is provided a composition comprising a nanoparticle of the invention.

By another aspect, there is provided a method of treating, preventing or ameliorating a disease or condition comprising administering a compound of the invention, thereby treating a disease or condition.

By another aspect, there is provided a method of treating, preventing or ameliorating a disease or condition comprising administering a pharmaceutical composition of the invention, thereby treating a disease or condition.

By another aspect, there is provided a compound or a composition of the invention, for use in the treatment, prevention or amelioration of a disease or condition.

Compounds

According to some embodiments, the present invention provides a compound including any stereoisomer and/or any salt thereof, wherein the compound is represented by Formula I:

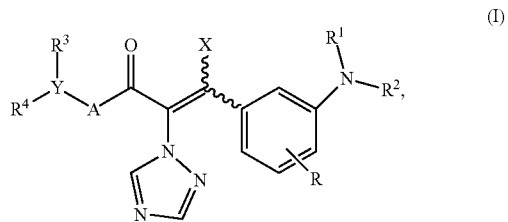

or by Formula:

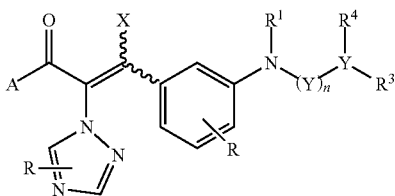

wherein: A represents a methyl group, isopropyl group, tert-butyl group, $C_2$-$C_{10}$ alkyl group, a substituted $C_2$-$C_{10}$ alkyl group, a $C_1$-$C_{10}$ haloalkyl group, a linear or branched $C_1$-$C_{10}$ alkyl group, a linear or branched $C_2$-$C_{10}$ alkyl group substituted or not substituted, optionally substituted $C_3$-$C_{10}$ cycloalkyl group comprising one or more carbocyclic rings, an optionally substituted $C_2$-$C_{10}$ alkyl group comprising one or more heteroatom(s), a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof; n is an integer between 0 and 5; Y is absent or is selected from the group consisting of N, NH, $NR^1$, $HCR^1$, $CH_2$, $C(R^1)_2$, CH, S, SH, and O; X is hydrogen or represents a substituent selected from the group consisting of: a halo group, a methyl group, isopropyl group, $C_2$-$C_{10}$ alkyl group, a substituted $C_2$-$C_{10}$ alkyl group, an alkoxy group, an amino group, and a hydroxy group; each R independently is absent or represents one or more substituents each independently comprising any one of a methyl group, isopropyl group, $C_2$-$C_{10}$ alkyl group, a substituted $C_2$-$C_{10}$ alkyl group, halo, oxo, —$NO_2$, amino, hydroxy, —CN, —OH, —$CONH_2$, —$CONR'_2$, —$CNNR'_2$, —$CSNR'_2$, —CONH—OH, —CONH—$NH_2$, —NHCOR, —NHCSR, —NHCNR, —NC(=O)OR, —NC(=O)NR', —NC(=S)OR', —NC(=S)NR', —$SO_2R'$, —SOR', —SR', —$SO_2OR'$, —$SO_2N(R')_2$, —$NHNR'_2$, —NNR', $C_1$-$C_6$ haloalkyl, optionally substituted $C_1$-$C_6$ alkyl, —$NH_2$, —NR'R', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy ($C_1$-$C_6$ alkoxy), alkoxy($C_1$-$C_6$ alkyl), alkoxy($C_1$-$C_6$ alkoxy), $C_1$-$C_6$ alkyl-$NR'_2$, $C_1$-$C_6$ alkyl-SR', —CONH($C_1$-$C_6$ alkyl), —CON($C_1$-$C_6$ alkyl)$_2$, —$CO_2H$, —$CO_2R'$, —OCOR, —OCOR', —OC(=O)OR', —OC(=O)NR', —OC(=S)OR', —OC(=S)NR', —OR', —NR'R', or a combination thereof; wherein each R' independently represents hydrogen, or is selected from the group comprising optionally substituted $C_1$-$C_{10}$ alkyl, optionally substituted $C_3$-$C_{10}$ cycloalkyl, optionally substituted $C_3$-$C_{10}$ heterocyclyl, optionally substituted heteroaryl, optionally substituted aryl, amino, hydroxy, halo, oxo, cyano, optionally substituted $C_1$-$C_{10}$ aminoalkyl, optionally substituted $C_1$-$C_{10}$ hydroxyalkyl, or any combination thereof as allowed by valency;

$R^1$ and $R^2$ are each independently selected from the group comprising hydrogen, oxygen, $C_1$-$C_{20}$ alkyl group, optionally substituted linear or branched $C_1$-$C_{20}$ aminoalkyl group, optionally substituted linear, branched or cyclic $C_1$-$C_{20}$ alkyl group optionally comprising one or more heteroatom(s), a substituted $C_1$-$C_{20}$ alkyl group, a $C_1$-$C_{20}$ haloalkyl group, a substituted $C_1$-$C_{20}$ haloalkyl group, an aliphatic linear or branched $C_3$-$C_{20}$ aminoalkyl group optionally comprising one or more heterocyclic ring(s), or wherein $R^1$ and Y are interconnected so as to form an optionally substituted 4 to 8-membered ring, or wherein $R^1$ and $R^2$ are interconnected so as to form an optionally substituted 4 to 8-membered ring optionally comprising one or more heteroatoms, or any combination thereof; $R^3$ is absent, hydrogen, represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a thioalkoxy group, a thioalkyl group, a hydroxy group, a mercapto group, an allyl group, $C_1$-$C_{10}$ ether group, a vinyl group, a cyano group, a nitro group, a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^3$ and Y are interconnected so as to form an optionally substituted 4 to 8-membered ring; or $R^3$ and A are interconnected so as to form an optionally substituted 4 to 8-membered ring; and $R^4$ is absent, hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof or wherein $R^3$ and $R^4$ are interconnected so as to form an optionally substituted 4 to 8-membered ring.

In some embodiments, $R^3$ is hydrogen or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a thioalkoxy group, a thioalkyl group, a hydroxy group, a mercapto group, an allyl group, $C_1$-$C_{10}$ ether group, a vinyl group, a cyano group, a nitro group, a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof. In some embodiments, $R^3$ and A are interconnected so as to form an optionally substituted 4 to 8-membered ring.

In some embodiments, if Y is absent, then $R^3$ and $R^4$ is absent.

In some embodiments, if $R^1$ and $R^2$ is oxygen, then Y is N.

According to some embodiments, the present invention provides a compound represented by Formula IIa or IIb (including any stereoisomer thereof). In some embodiments, the compound is represented by Formula IIa:

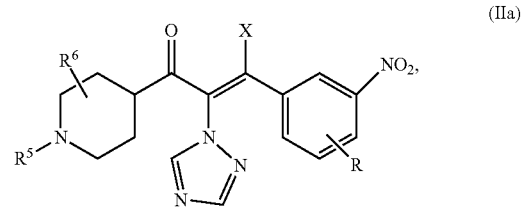

or Formula IIb:

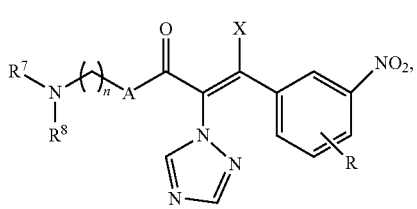

(IIb)

or Formula IIIb:

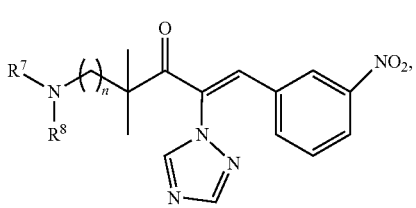

(IIIb)

wherein n, $R^5$, $R^6$ and $R^7$ are as described hereinabove.

According to some embodiments, the present invention provides a compound represented by Formula IIIc. In some embodiments, the compound is represented by formula IIIc:

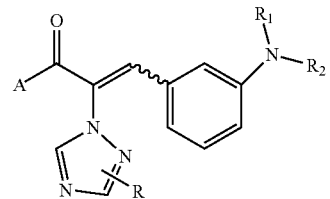

wherein $R^{13}$ is hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or any combination thereof; and $R^6$ is as described hereinabove.

According to some embodiments, the present invention provides a compound represented by Formula IV, IVa or IVb (including any stereoisomer thereof). In some embodiments, the compound is represented by Formula IV:

wherein: $R^5$ and $R^6$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or any combination thereof; n is an integer ranging between 0 and 5; and $R^7$ and $R^8$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^7$ and $R^8$ are interconnected so as to form an optionally substituted 4 to 8-membered ring. In some embodiments, n is an integer ranging between 0 and 4, between 0 and 3, or between 0 and 2. Each possibility represents a separate embodiment of the invention. In some embodiments, n is 0, 1, 2, 3, 4 or 5. Each possibility represents a separate embodiment of the invention.

According to some embodiments, the present invention provides a compound represented by Formula IIIa or IIIb (including any stereoisomer thereof). In some embodiments, the compound is represented by Formula IIIa:

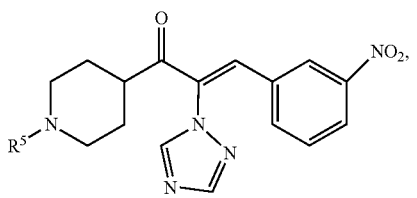

(IIIa)

wherein A is selected from the group comprising a methyl group, isopropyl group, tert-butyl group, a linear or branched $C_1$-$C_{10}$ alkyl group, optionally substituted $C_3$-$C_{10}$ cycloalkyl group comprising one or more carbocyclic rings, a linear or branched $C_2$-$C_{10}$ alkyl group, a linear or branched substituted $C_2$-$C_{10}$ alkyl group, $R^1$ and $R^2$ are each independently selected from the group comprising hydrogen, optionally substituted linear, branched or cyclic $C_1$-$C_{20}$ alkyl group optionally comprising one or more nitrogen atom(s); an optionally substituted $C_1$-$C_{20}$ alkyl group; an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; or wherein $R^1$ and $R^2$ are interconnected so as to form one or more 4 to 8-membered ring(s) optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group, or any combination thereof; and wherein at least one of $R^1$ and $R^2$ is any one of branched or cyclic $C_1$-$C_{20}$ alkyl group comprising one or more nitrogen atom(s); an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group.

In some embodiments, the compound is represented by Formula IV, wherein A represents a $C_2$-$C_{10}$ branched or linear alkyl; wherein R is optionally absent, and wherein at least one of $R^1$ and $R^2$ is a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group. In some embodiments, the compound is represented by Formula IV, wherein A represents a $C_2$-$C_{10}$ branched or linear alkyl; wherein R is optionally absent, and wherein at least one of $R^1$ and $R^2$ is a $C_5$-$C_{20}$ aminoalkyl group comprising between 1, 2, or 3 nitrogen atom(s) and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group. In some embodiments, the compound is represented by Formula IV, wherein A represents a $C_2$-$C_{10}$ branched or linear alkyl; wherein R is optionally absent, and wherein at least one of $R^1$ and $R^2$ is a cyclic (e.g, a polycyclic) $C_5$-$C_{20}$ aminoalkyl group comprising one or more aliphatic rings, wherein each ring comprises 1, 2, or 3 nitrogen atom(s) and is optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group.

In some embodiments, the term "stereoisomer" encompasses a cis-isomer and/or a trans-isomer of the compound.

In some embodiments, the compound is represented by Formula IVa:

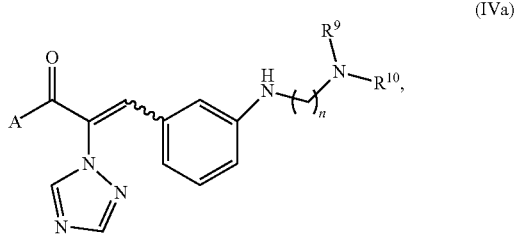

(IVa)

or Formula IVb:

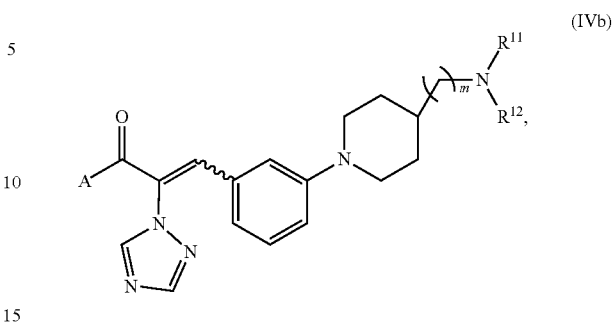

(IVb)

wherein: $R^9$ and $R^{10}$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof; or $R^9$ and $R^{10}$ are interconnected so as to form an optionally substituted 4 to 8-membered ring; m is an integer ranging between 0 and 7; and $R^{11}$ and $R^{12}$ are each independently selected from the group comprising hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^{11}$ and $R^{12}$ are interconnected so as to form an optionally substituted 4 to 8-membered ring. In some embodiments, m is an integer ranging between 0 and 6, between 0 and 5, between 0 and 4, between 0 and 3, or between 0 and 2. Each possibility represents a separate embodiment of the invention. In some embodiments, m is 0, 1, 2, 3, 4, 5, 6 or 7. Each possibility represents a separate embodiment of the invention.

In some embodiments, the compound is represented by Formula:

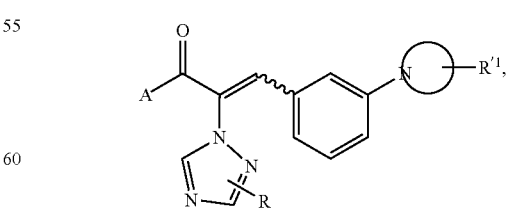

wherein A and R are as described herein, $R'^1$ is absent or represents one or more substituents each independently selected from the group comprising an optionally substituted linear, branched or cyclic $C_1$-$C_{20}$ alkyl group optionally comprising one or more nitrogen atom(s); an optionally substituted C₁-C₂₀ alkyl group; an optionally substituted linear or branched C₅-C₂₀ alkyl-aminoalkyl group; a linear, branched or cyclic C₅-C₂₀ aminoalkyl group comprising one or more nitrogen atoms and optionally substituted by one or more substituents independently selected from C₁-C₁₀ alkyl group, cyclic or non-cyclic C₁-C₁₀ alkylamino group, and cyclic or non-cyclic C₁-C₁₀ aminoalkyl group; halo, oxo, —NO₂, amino, hydroxy, —CN, —OH, —CONH₂, —CONR'₂, —CNNR'₂, —CSNR'₂, —CONH—OH, —CONH—NH₂, —NHCOR, —NHCSR, —NHCNR, —NC(=O)OR, —NC(=O)NR', —NC(=S)OR', —NC(=S)NR', —SO₂R', —SOR', —SR', —SO₂OR', —SO₂N(R')₂, —NHNR'₂, —NNR', C₁-C₆ haloalkyl, optionally substituted C₁-C₆ alkyl, —NH₂, —NR'R', —NH(C₁-C₆ alkyl), —N(C₁-C₆ alkyl)₂, C₁-C₆ alkoxy, C₁-C₆ haloalkoxy, hydroxy(C₁-C₆ alkyl), hydroxy(C₁-C₆ alkoxy), alkoxy(C₁-C₆ alkyl), alkoxy(C₁-C₆ alkoxy), C₁-C₆ alkyl-NR'₂, C₁-C₆ alkyl-SR', —CONH(C₁-C₆ alkyl), —CON(C₁-C₆ alkyl)₂, —CO₂H, —CO₂R', —OCOR, —OCOR', —OC(=O)OR', —OC(=O)NR', —OC(=S)OR', —OC(=S)NR', —OR', —NR'R', or a combination thereof; wherein each R' independently represents hydrogen, or is selected from the group comprising optionally substituted C₁-C₁₀ alkyl, optionally substituted C₃-C₁₀ cycloalkyl, optionally substituted C₃-C₁₀ heterocyclyl, optionally substituted heteroaryl, optionally substituted aryl, amino, hydroxy, halo, oxo, cyano, optionally substituted C₁-C₁₀ alkyl, or a combination thereof.

In some embodiments, the compound is represented by Formula:

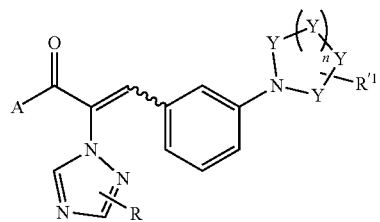

wherein n is 1-3; wherein each Y is independently CHR'¹ or NR'¹; and wherein R'¹ is as described herein. In some embodiments, up to 2 Y are NR'¹. In some embodiments, each Y is CHR'¹. In some embodiments, A is tert-butyl.

In some embodiments, the compound is represented by Formula:

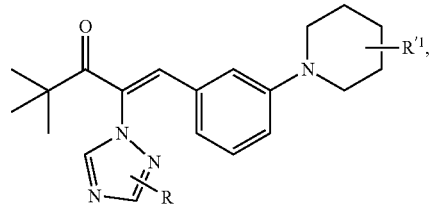

wherein R and R'¹ are as described herein. In some embodiments, the compound is as described hereinabove, wherein R'¹ is absent or represents one or more substituents each independently selected from the group comprising an optionally substituted cyclic C₅-C₆ aliphatic ring comprising one or more nitrogen atom(s); an optionally substituted linear, branched or cyclic C₁-C₂₀ alkyl group; a linear, branched or cyclic C₅-C₂₀ aminoalkyl group comprising one or more nitrogen atoms and optionally substituted by one or more substituents independently selected from C₁-C₁₀ alkyl group, cyclic or non-cyclic C₁-C₁₀ alkylamino group, and cyclic or non-cyclic C₁-C₁₀ aminoalkyl group; halo, oxo, —NO₂, amino, hydroxy, —CN, —OH, —CONH₂. In some embodiments, the compound is as described hereinabove, wherein R' is an optionally substituted cyclic C₅-C₆ aliphatic ring comprising one or more nitrogen atom(s); and wherein said optionally substituted cyclic C₅-C₆ aliphatic ring is bound via a nitrogen atom.

In some embodiments, the compound is selected from the group consisting of

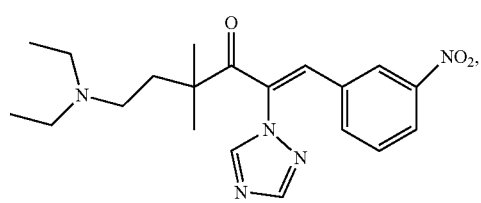
(T5)

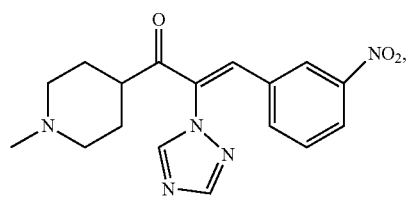
(T6)

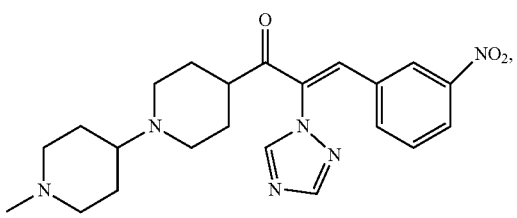
(T7)

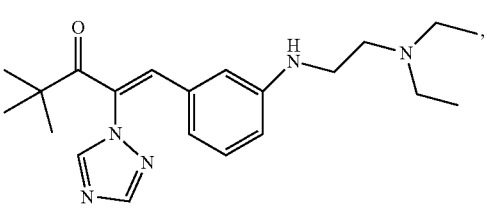
(T1)

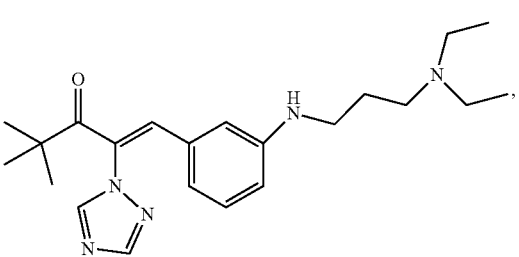
(T2)

-continued

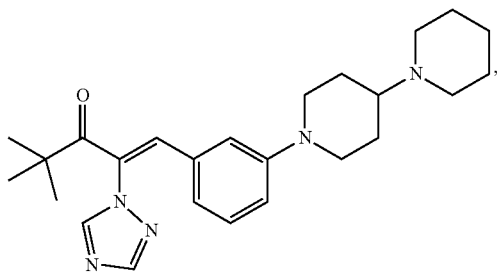
(T3)

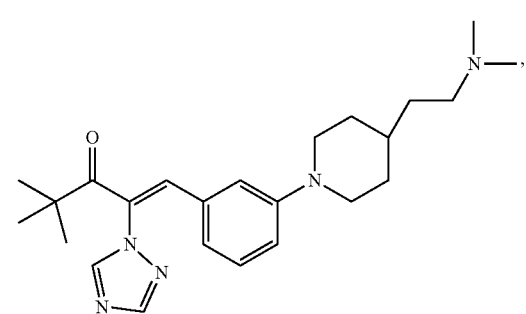
(T4)

including any stereoisomer thereof.
In some embodiments, the compound is

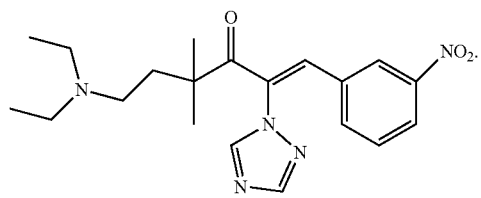
(T5)

In some embodiments, the compound is

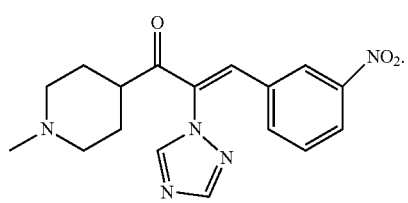
(T6)

In some embodiments, the compound is

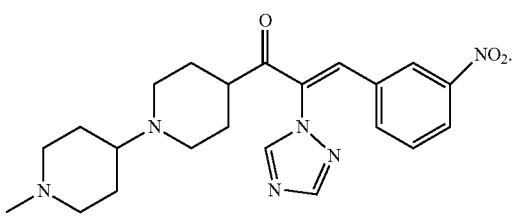
(T7)

In some embodiments, the compound is

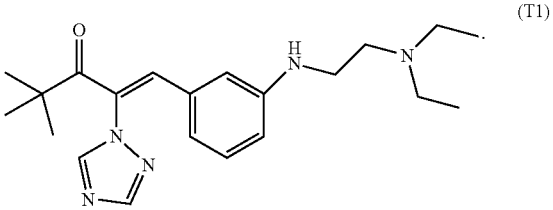 [SMILES: CCN(CC)CCNc1cccc(/C=C(/C(=O)C(C)(C)C)n2cncn2)c1]
(T1)

In some embodiments, the compound is

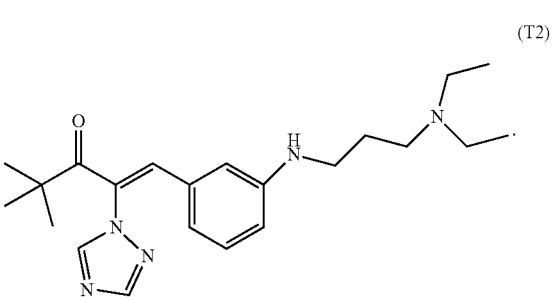 [SMILES: CCN(CC)CCCNc1cccc(/C=C(/C(=O)C(C)(C)C)n2cncn2)c1]
(T2)

In some embodiments, the compound is

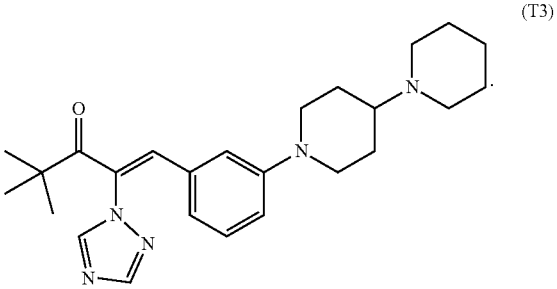 [SMILES: CC(C)(C)C(=O)/C(=C/c1cccc(N2CCC(N3CCCCC3)CC2)c1)n1cncn1]
(T3)

In some embodiments, the compound is

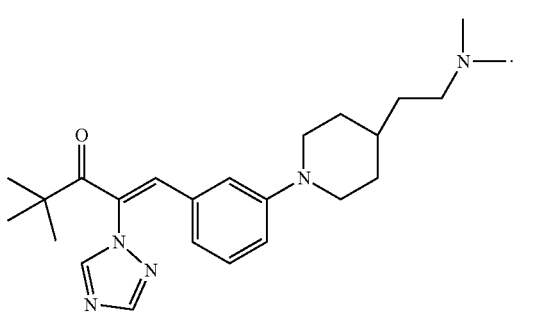
(T4)

In some embodiments, the compound is selected T1, T2 and T4. In some embodiments, the compound is a Z (or cis) isomer of the compound. In some embodiments, the compound is an E (or trans) isomer of the compound. In some embodiments, the compound the T1 Z isomer. In some embodiments, the compound is the T1 E isomer. In some embodiments, the compound is the T3 Z isomer. In some embodiments, the compound is the T3 E isomer. In some embodiments, the compound is the T4 Z isomer. In some embodiments, the compound is the T4 E isomer. It will be understood by a skilled artisan that the Z and E isomers refer to the carbon-carbon double bond that is found outside of the carbon ring. Each of T1-T7 contain only one the carbon-carbon double bond that is outside of the carbon ring.

Figure 8A:
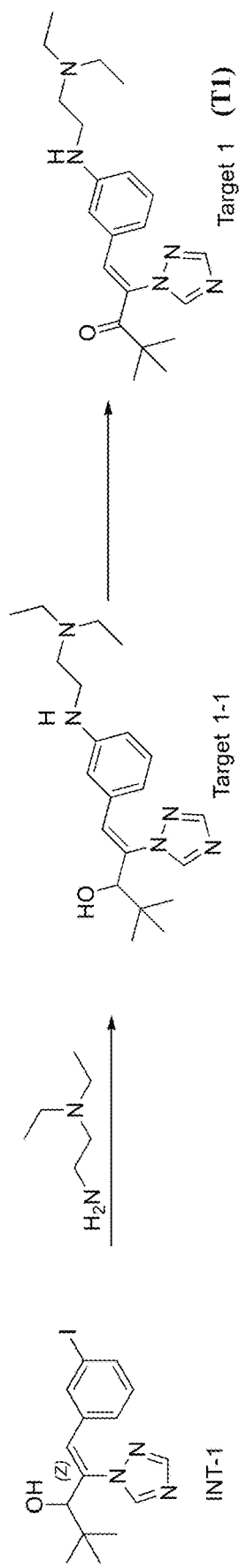
FIGS. 8A-C: Overview of synthesis mechanisms for production of (8A-B) compound T1 and (8C) compounds of Formula IV.
Figure 8B:
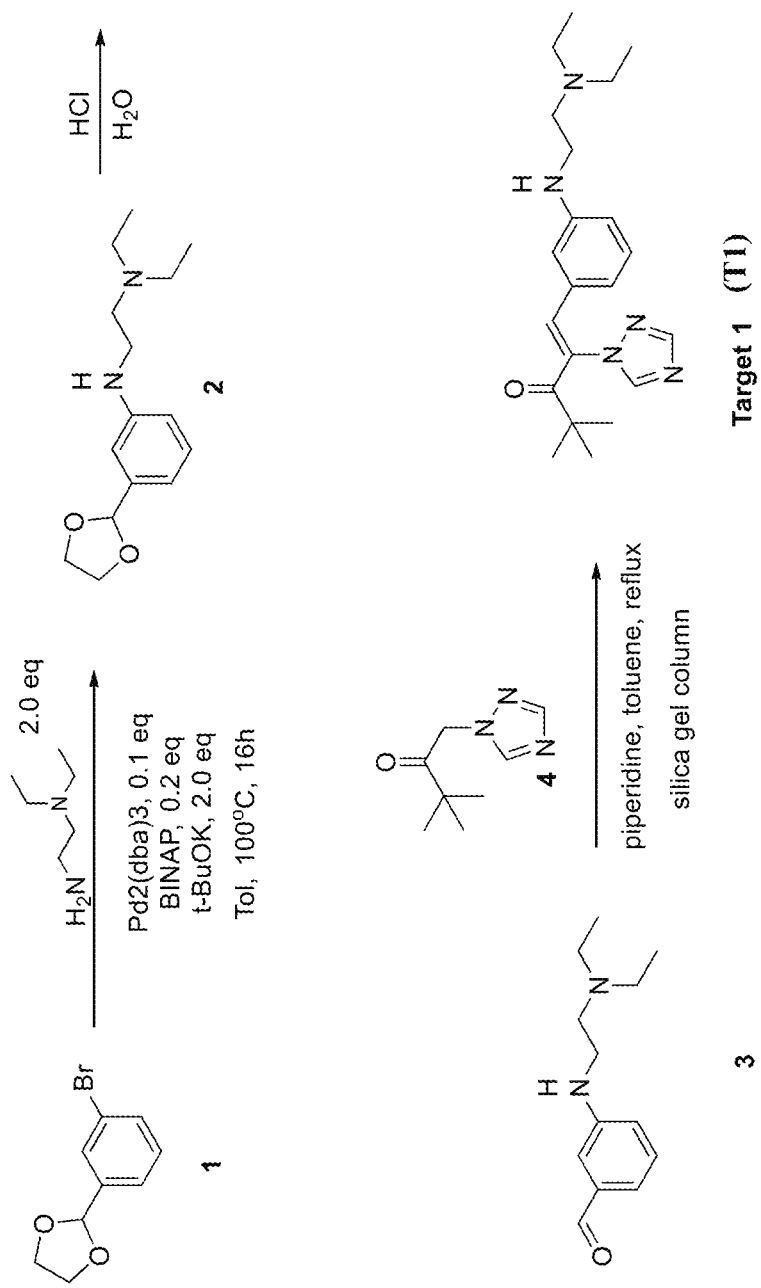

Reference is now made to FIGS. 8A and 8B which provide two different synthesis mechanisms for the production of compound T1. Both of these mechanisms can be used to create the T1 compound, both as a mixture of Z isomer and an E isomer, which can be separated by liquid chromatography (such as by using a chiral liquid chromatography column, which are well-known in the art) so as to result in a substantially pure Z or E isomer.

Figure 8C:
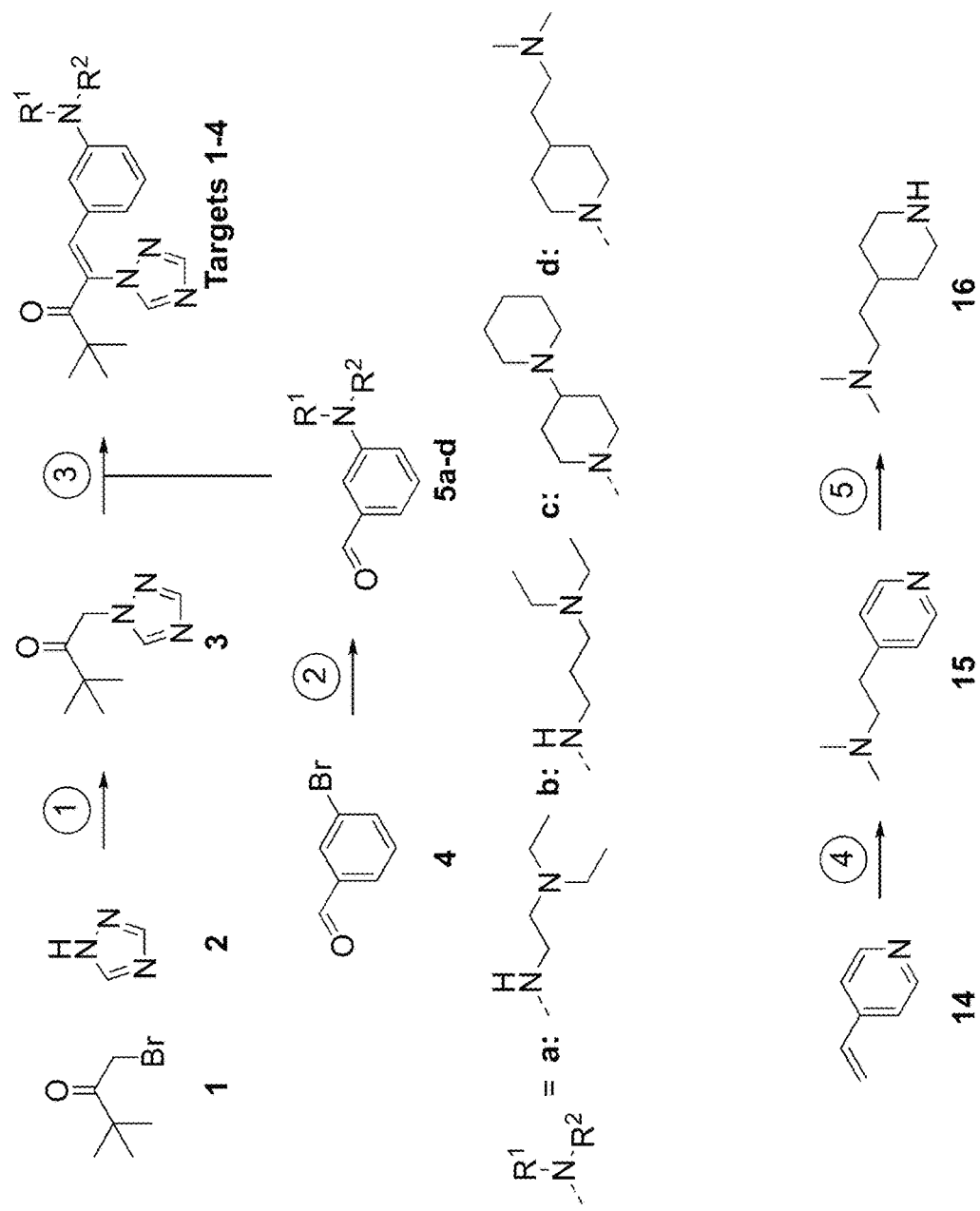

FIG. 8C provides a general synthesis mechanism for the production of compounds of Formula IV. Exemplary reaction conditions of each synthetic steps are provided hereinbelow.

Step 1: 1 (1 eq.), 2 (1.05 eq.), $K_2CO_3$ (1.05 eq.), acetone, reflux, 18 h.

Step 2: 4 (1 eq.), 16 (1.5 eq.), $K_2CO_3$ (2 eq.), CuI (0.1 eq.), DMSO, 80° C., 20 h.

Step 3 is performed as presented in FIG. 8B.

Step 4: 14 (1 eq.), $Me_2NH \cdot HCl$ (2 eq.), MeOH, reflux, 18 h

Step 5: 15 (1 eq.), H2 (1 atm.), $PtO_2$ (10% w/w), HCl (12M/H2O; 18 eq.), MeOH, RT, 6 h.

Figure 9A:
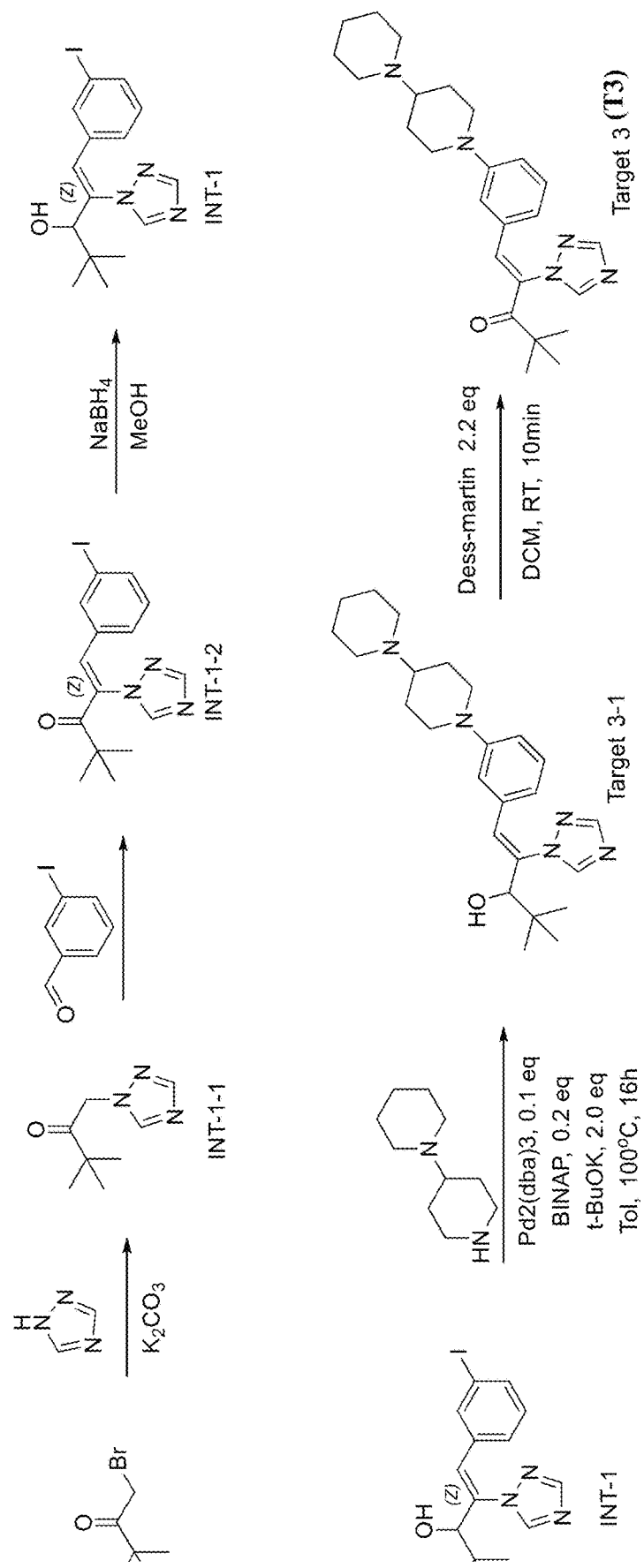
FIGS. 9A-B: Overview of a synthesis mechanisms for production of (9A) compound T3, and (9B) compounds of Formulae IIa-IIIc.

Reference is also made to FIG. 9A which provides a synthesis mechanism for the production of compound T3. Both the Z and E isomers can be produced (at the INT-1 stage) and then separated by liquid chromatography (such as by using a chiral liquid chromatography column, which are well-known in the art) so as to result in a substantially pure Z or E isomer of INT-1. Each of the Z/E INT-1 can be further reacted according to the synthetic steps presented in FIG. 9A, so as to result in a substantially pure Z or E isomer of T3.

Figure 9B:
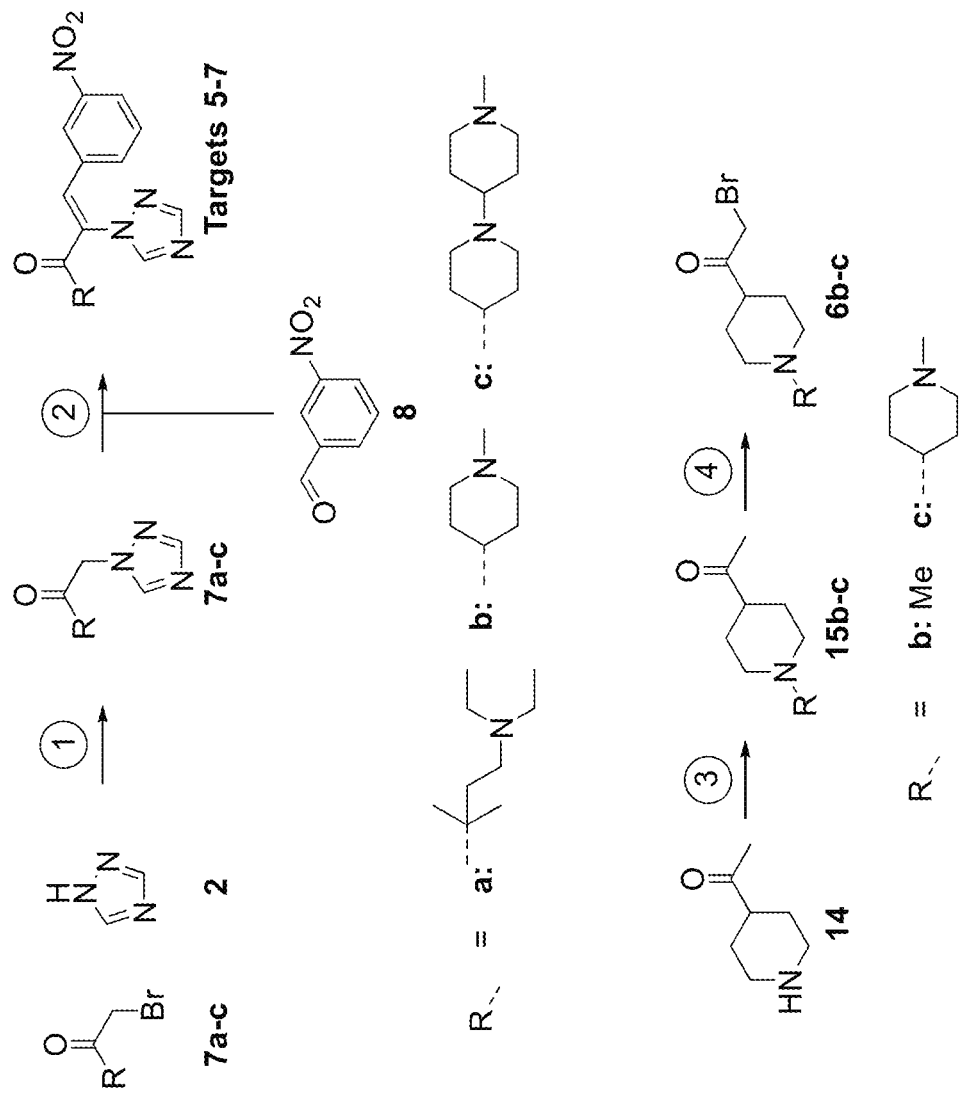

FIG. 9B provides a non-limiting general synthesis mechanism for the production of compounds of Formulae IIa-IIIc. Exemplary reaction conditions of each synthetic steps are provided hereinbelow.

Steps 1 and 2 are performed as described hereinabove.

Step 3. 14 (1 eq.), 4-bromo-1-methylpiperidine (1.1 eq.), $K_2CO_3$ (2.6 eq.), dioxane, 100° C., 20 h.

Step 4: NaBr (0.11 eq.), DMF, 150° C., 24 h.

In some embodiments, the compound is an inhibitor of neutrophil function or activity. In some embodiments, the compound is a neutrophil exocytosis inhibitor. In some embodiments, the compound inhibits neutrophils. In some embodiments, inhibiting neutrophils comprises inhibiting neutrophil activation. In some embodiments, inhibiting neutrophils comprises inhibiting neutrophil degranulation. In some embodiments, inhibiting neutrophils comprises inhibiting neutrophil exocytosis. In some embodiments, inhibiting neutrophils comprises inhibiting reactive oxygen species (ROS) production. In some embodiments, ROS production is ROS secretion. In some embodiments, inhibiting neutrophils comprises inhibiting neutrophil mediated killing. In some embodiments, inhibiting neutrophils comprises inhibiting neutrophil mediated cytotoxicity. In some embodiments, inhibiting neutrophils comprises inhibiting protease secretion. In some embodiments, inhibiting neutrophils comprises inhibiting NET production. In some embodiments, inhibiting neutrophils does not inhibit NET production. In some embodiments, inhibiting neutrophils comprises inhibiting inflammation. In some embodiments, the compound inhibits binding of RAB27a to SYTL1. Ras-related protein Rab-27a (RAB27a) is a small GTPase essential for neutrophil exocytosis. Synaptotagmin-like protein 1 (SYTL1) is also known as JFC1 and is a Rab27a effector that regulates trafficking, docking and exocytosis. In some embodiments, the compound is at least as effective as Nexinhib20. In some embodiments, the compound is superior to Nexinhib20. In some embodiments, the compound is at least as effective as Trifluoperazine (Stelazine®). In some embodiments, the compound is superior to Trifluoperazine (Stelazine®).

Nanoparticle

According to some embodiments, the present invention provides a nanoparticle comprising a compound of the invention. In some embodiments, the nanoparticle comprises a core. In some embodiments, the nanoparticle comprises a shell. In some embodiments, the core faces the shell. In some embodiments, the shell is a lipid layer. In some embodiments, the core is aqueous. In some embodiments, the core is hydrophilic. In some embodiments, the shell comprises a lipid layer and the core comprises a compound as described hereinabove. In some embodiments, the lipid layer comprises a phospholipid. In some embodiments, the compound is in the shell. In some embodiments, the compound is in the core. In some embodiments, the compound is dissolved in the aqueous core. In some embodiments, the compound is dissolved in an aqueous solution and loaded into the nanoparticle. In some embodiments, the compound is dissolved in an aqueous solution and loaded into the core. In some embodiments, a portion of the compound is in the shell and a portion is of the compound is in the core. In some embodiments, a hydrophobic portion of the compound is in the shell. In some embodiments, a hydrophobic portion is a hydrophobic moiety. In some embodiments, a hydrophilic portion of the compound is in the core. In some embodiments, a hydrophilic portion is a hydrophilic moiety.

In some embodiments, a compound as described herein is loaded into the nanoparticle. In some embodiments, a compound as described herein is carried by the nanoparticle (e.g., by interactions with the shell).

In some embodiments, the nanoparticle is a sub-micron size particle. In some embodiments, the nanoparticle is characterized by a particle size between 50 nm and 500 nm, between 70 nm and 500 nm, between 80 nm and 500 nm, between 100 nm and 500 nm, between 50 nm and 200 nm, between 70 nm and 200 nm, between 80 nm and 200 nm, between 100 nm and 200 nm, between 50 nm and 150 nm, between 70 nm and 150 nm, between 80 nm and 150 nm, between 100 nm and 150 nm, between 50 nm and 100 nm, between 70 nm and 100 nm, between 80 nm and 100 nm, between 80 nm and 130 nm, between 90 nm and 150 nm, between 90 nm and 120 nm, between 100 nm and 130 nm, between 130 nm and 150 nm, between 150 nm and 200 nm, between 200 nm and 300 nm, between 80 nm and 300 nm, between 50 nm and 300 nm, between 50 nm and 80 nm, between 80 nm and 150 nm, including any range between. Each possibility represents a separate embodiment of the invention. In some embodiments, a nanoparticle comprises an average size of about 100 nm. In some embodiments, a nanoparticle comprises an average size of between 70 and 150 nm. In some embodiments, a nanoparticle comprises an average size of between 100 and 150 nm. In some embodiments, a nanoparticle comprises an average size of between 80 and 100 nm. The size of the nanoparticle can be determined by any method known in the art, such as for example dynamic light scattering (DLS) for determining the hydrodynamic diameter of the particles and transmission electron microscopy (TEM) for determining the accurate geometric nanoparticle size.

According to some embodiments, the size of the nanoparticle is within the range of 50-1000, 100-1000, 200-1000, 250-1000, 300-1000, 500-1000, 600-1000, 700-1000, 50-900, 100-900, 200-900, 250-900, 300-900, 500-900, 600-900, 700-900, 50-800, 100-800, 200-800, 250-800, 300-800, 500-800, 600-800, 700-800, 50-600, 100-600, 200-600, 250-600, 300-600, 500-600, or 50-200 nm. Each possibility represents a separate embodiment of the present invention. According to some embodiments, the nanoparticle is selected from a nanosphere and a nanorod. As used herein, the term "nanosphere" refers to a nanoparticle having a spherical shape. The term "nanorod" refers to a nanoparticle having a rod-like shape. According to some embodiments, the nanoparticle is a liposome. According to other embodiments, the nanoparticle is a polymeric nanoparticle. According to additional embodiments, the polymeric nanoparticle comprises poly(lactic-co-glycolic acid) (PLGA). According to additional embodiments, the nanoparticle is a metallic nanoparticle. According to some embodiments, the nanoparticle is a DSPE-PEG nanoparticle. According to some embodiments, the nanoparticle is a DSPE-PEG-Maleimide nanoparticle. According to some embodiments, the PEG is 3400. According to some embodiments, the PEG is 2000. According to some embodiments, the PEG is 5000. According to particular embodiments, the nanoparticle is fluorescently-labeled. According to some embodiments, the nanoparticle is modified with PEG. According to some embodiments, the nanoparticle comprises a PLGA core. In some embodiments, the nanoparticle is coated with a reactive agent. In some embodiments, the reactive agent is suitable for conjugating the peptide, peptide multimer or peptide complex to the nanoparticle. Reactive groups for conjugation are well known in the art and examples of such are provided herein below. According to some embodiments, the reactive group is a binding or capture group. In some embodiments, the binding or capture group is for binding or capturing a peptide or a linker or spacer. In some embodiments, the reactive group is streptavidin (SA). In some embodiments, the SA is for binding a peptide/multimer/complex comprising biotin. In some embodiments, the reactive group is a thiol. In some embodiments, the thiol is for binding a peptide/multimer/complex comprising a cysteine. In some embodiments, the cysteine is a free cystine. In some embodiments, the cysteine is in a linker. In some embodiments, the linkage is a maleimide linkage.

In some embodiments, the nanoparticle is characterized by a diameter at least 50 nm, at least 60 nm, at least 70 nm, at least 80 nm, at least 90 nm, or at least 100 nm, including any value therebetween. Each possibility represents a separate embodiment. In some embodiments, the nanoparticle is characterized by a diameter at most 130 nm, at most 150 nm, at most 170 nm, at most 180 nm, at most 200 nm, at most 250 nm, at most 300 nm, including any value therebetween. Each possibility represents a separate embodiment of the invention.

In some embodiments, the lipid layer comprises, a phospholipid and a sterol. In some embodiments, the sterol comprises cholesterol. In some embodiments, the phospholipid comprises a zwitterionic lipid, an anionic lipid, or a PEG-ylated lipid including any combination thereof. In some embodiments, the nanoparticle is in a form of liposome or micelle. In some embodiments, the nanoparticle is a liposome. In some embodiments, the nanoparticle is a micelle.

In some embodiments, the lipid is or comprises one or more phospholipids. In some embodiments, the phospholipid is a liposome forming lipid. As used herein, the term "liposome forming lipid" encompasses phospholipids which upon dispersion or dissolution thereof in an aqueous solution at a temperature above a transition temperature (Tm), undergo self-assembly so as to form stable liposomes. As used herein, the term Tm refers to a temperature at which phospholipids undergo phase transition from solid (ordered phase, also termed as a gel phase) to a fluid (disordered phase, also termed as fluid crystalline phase). Tm also refers to a temperature (or to a temperature range) at which the maximal change in heat capacity occurs during the phase transition.

In some embodiments, the lipid layer and/or nanoparticle comprises 45-70, 45-65, 45-60, 45-55, 45-50, 50-70, 50-65, 50-60, 50-55, 55-70, 55-65, 55-60, 60-70, 60-65, or 65-70 mole percentage phospholipid. Each possibility represents a separate embodiment of the invention. In some embodiments, the lipid layer comprises 50-65 mole percentage phospholipid. In some embodiments, the lipid layer comprises 50-65 mole percentage phospholipid.

In some embodiments, the nanoparticle encapsulates the compound. In some embodiments, the nanoparticle comprises a hydrophilic core and the compound is in the core. In some embodiments, the nanoparticle comprises a hydrophobic core and the compound is in the core. In some embodiments, the compound is associated with the surface of the nanoparticle. In some embodiments, the compound is linked or conjugated to the surface of the nanoparticle by a sidechain of the compound. In some embodiments, the compound is embedded in the shell of the nanoparticle by a sidechain of the compound.

According to some embodiments, the present invention provides a composition comprising a plurality of nanoparticles as described hereinabove.

In some embodiments, the nanoparticles of the invention are characterized by a polydispersity index of less than 0.6, less than 0.5, less than 0.3, less than 0.2, or less than 0.1, including any value therebetween. Each possibility represents a separate embodiment of the invention. In some embodiments, the nanoparticles of the invention are characterized by a polydispersity index of less 0.1.

In some embodiments, the nanoparticles of the invention are characterized by a polydispersity index of between 0.001 and 0.3, between 0.001 and 0.2, between 0.001 and 0.1, between 0.005 and 0.3, between 0.005 and 0.2, between 0.005 and 0.1, between 0.01 and 0.3, between 0.01 and 0.2, between 0.01 and 0.1, between 0.05 and 0.3, between 0.05 and 0.2, or between 0.05 and 0.1, including any value and range therebetween. Each possibility represents a separate embodiment of the invention. In some embodiments, the nanoparticles of the invention are characterized by a median size, as described hereinabove, and are further characterized by polydispersity index of between 0.001 and 0.3, between 0.001 and 0.2, between 0.001 and 0.1, between 0.005 and 0.3, between 0.005 and 0.2, between 0.005 and 0.1, between 0.01 and 0.3, between 0.01 and 0.2, between 0.01 and 0.1, between 0.05 and 0.3, between 0.05 and 0.2, or between 0.05 and 0.1, including any value and range therebetween. Each possibility represents a separate embodiment of the invention.

In some embodiments, at least 80%, at least 85%, at least 90%, at least 95%, at least 97% by weight of the nanoparticles of the invention are characterized by a particle size in a range of between 50 nm and 500 nm, between 50 nm and 300 nm, between 50 nm and 200 nm, between 80 nm and 200 nm, between 80 nm and 100 nm, between 80 nm and 150 nm, between 80 nm and 130 nm, between 100 nm and 150 nm, between 150 nm and 200 nm, between 200 nm and 250 nm, between 250 nm and 300 nm, including any value and range therebetween. Each possibility represents a separate embodiment of the invention.

The terms "particle size" and "particle diameter" are used herein interchangeably and refer to an average cross section size of the nanoparticles (e.g., a largest linear distance between two points on the surface of the nanoparticle) within a liquid composition. In some embodiments, the term "average cross section size" may refer to either the average of at least e.g., 70%, 80%, 90%, or 95% of the particles, or in some embodiments, to the median size of the plurality of nanoparticles. In some embodiments, the term "average cross section size" refers to a number average of the plurality of nanoparticles. In some embodiments, the term "average cross section size" may refer to an average diameter of substantially spherical nanoparticles.

In some embodiments, the nanoparticle of the invention is or comprises a lipid-based particle. In some embodiments, the nanoparticle of the invention is or comprises a liposome. In some embodiments, liposomes refer to vesicles with an internal core surrounded by a lipid bilayer/s and are widely used as drug carriers. This is greatly due to their unique characteristics such as good biocompatibility, low toxicity, lack of immune system activation, and the ability to incorporate both hydrophobic and hydrophilic compounds. As described herein, liposomes are known in the art as artificial vesicles composed of a substantially spherical lipid bilayer which typically, but not exclusively, comprises phospholipids, sterol, e.g., cholesterol, and other lipids.

In some embodiments, "vesicle" and "carrier" are synonymous and refer to a particle (e.g., the nanoparticle of the invention) comprising a core and a shell encapsulating or enclosing the core. In some embodiments, the nanoparticle of the invention comprises a core and a shell encapsulating or enclosing the core. In some embodiments, the core is a hollow core, or a core filled with a solid or liquid material. In some embodiments, the nanoparticle of the invention may have a spherical or any other geometrical shape. In some embodiments, the nanoparticle of the invention comprises a unilamellar or multilamellar membrane (or lipid layer). In some embodiments, the nanoparticle of the invention comprises one or more different types of nanoparticles. In some embodiments, "by different types" it is meant to refer to liposomes that encapsulate different active agents (e.g., the compounds of the present invention). In some embodiments, "by different types" it is meant to refer to liposomes that are of different structure and configurations.

In some embodiments, the liposomes disclosed herein can be any one or combination of vesicles selected from the group consisting of small unilamellar vesicles (SUV), large unilamellar vesicles (LUV), multilamellar vesicles (MLV), multivesicular vesicles (MVV), large multivesicular vesicles (LMVV, also referred to, at times, by the term giant multivesicular vesicles, "GMV"), oligolamellar vesicles (OLV), and others. In some embodiments, the liposomes are large unilameller vesicles (LUV). Methods of preparing and characterizing pharmaceutical liposome compositions are known in the field (see, e.g., Lasic D. Liposomes: From physics to applications, Elsevier, Amsterdam 1993; G. Greroriadis (ed.), Liposome Technology, 3rd edition, vol. 1-3, CRC Press, Boca Raton, 2006; Hong et al., U.S. Pat. No. 8,147, 867, incorporated by reference herein in their entirety for all purposes).

In some embodiments, the liposomes are characterized by a proper packing parameter. As used herein and in the art, "packing parameter" is a relative measure of a given lipid composition, and depend on factors such as size relationships between lipid head groups and lipid hydrocarbon chains, charge, and the presence of stabilizers such as cholesterol. It should also be noted that the packing parameter may be not constant. In some embodiments, the parameter is dependent on various conditions which effect each the volume of the hydrophobic chain, the cross-sectional area of the hydrophilic head group, and the length of the hydrophobic chain. Factors can affect these include, but are not limited to, the properties of the solvent, the solvent temperature, and the ionic strength of the solvent.

In some embodiments, the proper packing parameter is in the range of 0.3 to 1, e.g., 0.3, 0.5, 0.7, 0.9, or 1, including any value and range therebetween.

The term "core", as used herein, refers to the central portion of the particle, with a different composition than the shell. In some embodiments, the core is enclosed by the shell. In some embodiments, the core is bound to the inner portion of the shell. In some embodiments, the core comprises a compound as described hereinabove enclosed by the shell.

In some embodiments, the core is a liquid. In some embodiments, the core comprises an aqueous solution. In some embodiments, the core comprises an aqueous solution of a compound as described herein. In some embodiments, the core comprises a compound as described herein, substantially located therewithin.

In some embodiments, there is a composition comprising a plurality of nanoparticles of the invention, wherein the nanoparticles are the same or different. In some embodiments, by "different nanoparticles" it is meant to refer to particles that encapsulate different active agents (e.g., the compounds of the present invention).

In some embodiments, the shell is or comprises a lipid layer. In some embodiments, the shell is in a form of a membrane. In some embodiments, the shell comprises one or more lipid layers. In some embodiments, the shell comprises a lipid bilayer. The term 'shell,' as used herein, refers to the outer portion of the particle, with a different composition than the core.

In some embodiments, the lipid layer comprises a phospholipid. In some embodiments, the phospholipid encompasses a single phospholipid species or a plurality of chemically distinct phospholipids. In some embodiments, the phospholipid is or comprises a liposome forming lipid, wherein the liposome forming lipid is as described herein above.

In some embodiments, at least one of the liposome forming lipid is a phospholipid having one or two C14 to C24 hydrocarbon tails, typically, acyl, alkyl or alkenyl chain) and have varying degrees of unsaturation, from being fully saturated to being fully, partially or non-hydrogenated lipids (the level of saturation may affect rigidity of the liposome thus formed (typically liposomes formed from lipids with saturated chains are more rigid than liposomes formed from lipids of same chain length in which there are un-saturated chains, especially having cis double bonds). In some embodiments, at least one of the liposome forming lipid is a phospholipid having one or two C14 to C20, C16 to C20, or C16 to C18 hydrocarbon tails, including any value and range therebetween. Each possibility represents a separate embodiment of the invention. In some embodiments, at least one of the liposome forming lipid is fully saturated.

Further, the lipid membrane may be of natural source (e.g., naturally occurring phospholipids), semi-synthetic or fully synthetic lipid, as well as electrically neutral, negatively, or positively charged.

In some embodiments, the primary liposome forming phospholipid is characterized by a Tm greater than about 40° C., greater than about 45° C., greater than about 50° C., greater than about 52° C., including any range between.

In some embodiments, the liposome forming phospholipid comprises one or more saturated and/or unsaturated hydrocarbon tails. In some embodiments, each hydrocarbon tail independently comprises between 14 and 24, between 16 and 24, between 17 and 24, between 17 and 20, between 14 and 17, between 20 and 24, between 18 and 20 carbon atoms, including any range between. In some embodiments, the hydrocarbon tails of the lipid have the same or different chemical composition.

In some embodiments, the phospholipid is hydrogenated soy phosphatidyl choline (HSPC), 1,2-Distearoyl-sn-glycero-3-phosphorylethanolamine (DSPE), distearoylphosphatidylcholine (DSPC), or egg sphingomyelin (ESM). In some embodiments, the phospholipid is HSPC. In some embodiments, the phospholipid is DSPC. In some embodiments, the phospholipid is a combination of HSPC and DSPC. The term "phospholipid" as used herein refers to any one phospholipid or combination of phospholipids capable of forming liposomes. Neutral phospholipids can include diacylphosphatidylcholines, dialkylphosphatidylcholines, sphingomyelins, and diacylphosphatidylethanolamines. Phosphatidylcholines (PC), including those obtained from egg, soybeans or other plant sources or those that are partially or wholly synthetic, or of variable lipid chain length and unsaturation are suitable for use in the present compositions. Synthetic, semisynthetic and natural product phosphatidylcholines but including, not limited to, distearoylphosphatidylcholine (DSPC), DSPE, hydrogenated soy phosphatidylcholine (HSPC), soy phosphatidylcholine (soy PC), egg phosphatidylcholine (egg PC), hydrogenated egg phosphatidylcholine (HEPC), and dipalmitoylphosphatidylcholine (DPPC) are suitable phosphatidylcholines for use in the preparation of liposomes. Charged phospholipids can include phosphatidylglycerols, cardiolipins, or headgroup modified lipids such as N-succinyl-phosphatidylethanolamines, N-glutaryl-phosphatidylethanolamines, and PEG-derivatized phosphatidylethanolamines.

In some embodiments, the lipid layer comprises one or more sterols. Non-limiting examples of sterols include but are not limited to β-sitosterol, β-sitostanol, stigmasterol, stigmastanol, campesterol, campestanol, ergosterol, avenasterol, brassicasterol, fucosterol, cholesterol (CHOL), cholesteryl hemisuccinate, and cholesteryl sulfate, or any combination thereof.

In some embodiments, the sterol is a plant derived sterol, namely, a phytosterol. In accordance with this embodiment, the sterol is selected from the group consisting of β-sitosterol, β-sitostanol, stigmasterol, stigmastanol, campesterol, campestanol, ergosterol, avenasterol, brassicasterol and any combination thereof.

In some embodiments, the lipid layer and/or nanoparticle comprises 30-55, 33-55, 35-55, 37-55, 40-55, 43-55, 45-55, 47-55, 50-55, 53-55, 30-53, 33-53, 35-53, 37-53, 40-53, 43-53, 45-53, 47-53, 50-53, 30-50, 33-50, 35-50, 37-50, 40-50, 43-50, 45-50, 47-50, 30-47, 33-47, 35-47, 37-47, 40-47, 43-47, 45-47, 30-45, 33-45, 35-45, 37-45, 40-45, 43-45, 30-43, 33-43, 35-43, 37-43, 40-43, 30-40, 33-40, 35-40, 37-40, 30-37, 33-37, 35-37, 30-35, 33-35, or 30-33 mole percentage sterol. Each possibility represents a separate embodiment of the invention. In some embodiments, the lipid layer comprises 33-50 mole percentage sterol. In some embodiments, the nanoparticle comprises 33-50 mole percentage sterol.

In some embodiments, the liposomes comprise polymer-conjugated lipids that can be used in the liposomal formulation to increase the lifetime of circulation via reducing liposome clearance by liver and spleen, or to improve the stability of liposomes against aggregation during storage. Polymer-conjugated lipids may include poly(ethylene glycol)-conjugated (pegylated)phospholipids (PEG-lipids) such as PEG(Mol. weight 2,000) methoxy-poly(ethylene glycol)-1,2-distearoyl-sn-glycerol (PEG(2000)-distearoylglycerol, PEG-DSG), PEG(Mol. weight 2,000) 1,2-distearoyl-sn-glycero-3-phosphoethanolamine-N-[methoxy(polyethylene glycol)-2000] (PEG(Mol. weight 2,000)-distearoylphosphatidylethanolamine, PEG-DSPE or DSPE-PEG), or PEG (Mol. weight 2,000) N-palmitoyl-sphingosine-1-{succinyl [methoxy(polyethylene glycol)-2000]} (PEG-ceramide). The molecular weight of the PEG portion in the PEG-lipid component can also vary from 1,500-5,500 g/mol, but is preferably about 2,000 MW. In some embodiments, the PEG is PEG3400. In some embodiments, the PEG comprises a MW of about 5000. Other polymers used for conjugation to lipid anchors may include poly(2-methyl-2-oxazoline) (PMOZ), poly(2-ethyl-2-oxazoline) (PEOZ), polyamide oligomers, polysarcosine, poly-N-vinylpyrrolidone (PVP), polyglycerol, poly(hydroxyethyl L-asparaginc) (PHEA), and poly(hydroxyethyl L-glutamine) (PHEG).

In some embodiments, the nanoparticles of the invention encapsulate an effective amount (e.g., therapeutically effective amount) of a compound as described hereinabove. In some embodiments, the nanoparticles of the invention are characterized by a loading of the compound of the invention (also refers to herein, as active compound or active agent) sufficient for utilizing thereof in the treatment or prevention of a disease.

In some embodiments, the process to generate the liposomes with the compound therein includes the steps of (a) preparing a liposome containing a trapping agent composed of an ammonium or substituted ammonium salt of a polyanion, (b) subsequently removing trapping agent from the outside of the liposomes to form an electrochemical gradients across the lipid membrane, and (c) adding the active compound desired to be encapsulated under conditions effective for the compound to enter the liposome and be stabilized as the corresponding salt with the remaining intraliposomal polyanion. Liposome compositions containing a trapping agent in the interior of the liposome can be made by formation of the liposomes in a solution of the trapping agent. The transmembrane concentration gradient of the trapping agent can be formed across the liposome by the removal of the trapping agent outside of or dilution of the liposomes either following liposome formation or before loading (entrapping) of the drug.

In some embodiments the salt form in the interior of the liposomes is a polyanion such as citrate, sulfate, sucroseoctasulfate, dextran sulfate, suramin, polyphosphate, or inositol hexaphosphate. In some embodiments the intraliposomal salt of the drug is precipitated or gelated to improve retention of the drug upon administration.

In some embodiments, the composition of the invention comprises an effective amount (e.g., therapeutically effective amount) of a compound as described herein. In some embodiments, the composition of the invention is a pharmaceutical composition comprising a therapeutically effective amount of a compound, as described herein.

As used herein, a "therapeutically effective amount" or "an amount effective" refers to an amount effective, at dosages and for periods of time necessary, to achieve the desired therapeutic result. The therapeutically effective amount of the therapeutic agent will depend on the nature of the disorder or condition and on the particular agent and can be determined by standard clinical techniques known to a person skilled in the art. As used herein, the term "a therapeutically active agent" describes a chemical substance, which exhibit a therapeutic activity when administered to a subject.

In some embodiments, the nanoparticle (e.g., liposome) of the invention is composed of the pharmaceutically acceptable ingredients (such as phospholipids and/or sterol) or pharmaceutically acceptable salt thereof.

The invention is based, at least in part, on the surprising finding that the compounds of the invention can be easily loaded into nanoparticles and in particular lipid-based nanoparticles (i.e., liposomes). The unique structures of the compounds of the invention allow for effective loading into nanoparticles such that a therapeutically effective dose of the compounds can be easily loaded. These compounds are high useful and superior to other similar compounds known in the art in that they can be efficiently and highly loaded into nanoparticles (i.e., liposomes).

In some embodiments, the nanoparticle further comprises a peptide that binds to neutrophils. In some embodiments, the peptide is a neutrophil-targeting peptide. In some embodiments, the peptide is attached or linked to the surface of the nanoparticle. In some embodiments, the peptide is attached or linked to the shell of the nanoparticle. In some embodiments, the peptide is attached or linked to the outside of the nanoparticle. In some embodiments, linked is covalently linked. In some embodiments, the outside is the side not facing the core. In some embodiments, the peptide is attached to the nanoparticle. In some embodiments, the peptide is attached to the nanoparticle and is free to interact with a neutrophil external to the nanoparticle.

In some embodiments, the peptide is conjugated to an activated-PEG lipid, such as maleimide-terminated-PEG-distearoylphosphatidylethanolamine (DSPE). The PEG linker is between 1,500-5,000 MW, and between 1,900-3,600. Preferably the PEG linker is larger (e.g., 3,400 MW) than the PEG used for preventing aggregation or extending circulation lifetimes (e.g., 2,000 MW). In some embodiments, the nanoparticle comprises DSPE-PEG. In some embodiments, the lipid layer comprises DSPE-PEG. In some embodiments, the activated-PEG lipid is DSPE-PEG. In some embodiments, the DSPE-PEG comprises a maleimide moiety.

In some embodiments, the lipid layer and/or nanoparticle comprises 1-10, 2-10, 3-10, 4-10, 5-10, 6-10, 7-10, 8-10, 9-10, 1-9, 2-9, 3-9, 4-9, 5-9, 6-9, 7-9, 8-9, 1-8, 2-8, 3-8, 4-8, 5-8, 6-8, 7-8, 1-7, 2-7, 3-7, 4-7, 5-7, 6-7, 1-6, 2-6, 3-6, 4-6, 5-6, 1-5, 2-5, 3-5, 4-5, 1-4, 2-4, 3-4, 1-3, 2-3, or 1-2 mole percentage activated-PEG lipid. Each possibility represents a separate embodiment of the invention. In some embodiments, the lipid layer comprises 2-5 mole percentage activated-PEG lipid. In some embodiments, the nanoparticle comprises 2-5 mole percentage activated-PEG lipid.

The term "neutrophils" as used herein refers to the type of leucocyte most numerous in mammals, which forms an important part of the innate immune system. Neutrophils form part of a family of polymorphonuclear cells (PMN) with basophils and eosinophils. Neutrophils are normally found in the bloodstream. During the starting (acute) phase of inflammation, particularly as a result of bacterial infection, and certain forms of cancer, neutrophils are among the first immune cells migrating towards the site of inflammation/tumor. They migrate through the blood vessels, then through interstitial tissue, following chemical signals, such as interleukin-8 (IL-8) and C5a. The term "neutrophils" as used herein encompasses all types of neutrophils, either mature, immature, high-density or low-density, including but not limited to High Density Neutrophils—HDNs and Low Density Neutrophils (LDNs).

The term "peptide" refers to a short chain of amino acid residues linked by peptide bonds, i.e., a covalent bond formed between the carboxyl group of one amino acid and an amino group of an adjacent amino acid. The term "peptide" refers to short sequences having up to 50 amino acids. A chain of amino acids monomers longer than 50 amino acid is referred as a "polypeptide". Such polypeptides, when having more than 50 amino acid residues, can also be classified as proteins, more particularly, proteins of low or medium molecular weight.

The term "peptide" encompasses also the term "peptide analog". The term "peptide analog" and "analog" are used herein interchangeably and refer to an analog of a peptide having at least 80% identity with the original peptide, wherein the analog retains the activity of the original peptide. Thus, the terms "analog" and "active analog" may be used interchangeably. The term "analog" refers to a peptide which contains substitutions, rearrangements, deletions, additions and/or chemical modifications in the amino acid sequence of the parent peptide. According to some embodiments, the peptide analog has at least 80%, at least 90% or at least 95% sequence identity to the original peptide. According to one embodiment, the analog has about 70% to about 95%, about 80% to about 90% or about 85% to about 95% sequence identity to the original peptide. According to some embodiments, the analog of the present invention comprises the sequence of the original peptide in which 1 or 2 deletions, additions and/or substitutions were made.

The term "peptide" encompasses also the term "peptide fragment". The term "fragment" refers to a fragment of the original peptide or of an analog thereof in which 1 or 2 amino acid residues have been deleted, wherein the fragment retains the activity of the original peptide or analog. Thus, the terms "fragment" and "active fragment" may be used interchangeably.

The substitutions of the amino acids may be conservative or non-conservative substitution. The non-conservative substitution encompasses substitution of one amino acid by any other amino acid. In one particular embodiment, the amino acid is substituted by a non-natural amino acid.

The term "analog" encompasses also the term "conservative analog". Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. One of skill will recognize that individual substitutions, is a "conservatively modified analog" where the alteration results in the substitution of an amino acid with a chemically similar amino acid. Conservative substitution tables providing functionally similar amino acids are well known in the art. One typical example of conservative substitution is provided below.

The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4)

Arginine (R), Lysine (K); (5) Isoleucine (I), Leucine (L), Methionine (M), Valine (V); and (6) Phenylalanine (F), Tyrosine (Y), Tryptophan (W). In other embodiments, the conservative substitution encompass substitution with a chemically similar non-natural amino acid.

Thus, in some embodiments, the analog is a conservative analog of the peptide. According to some embodiments, the conservative analog of the present invention comprises the sequence of the original peptide in which 1 or 2 conservative substitutions were made. According to another embodiment, the analog consists of the amino acid sequence of the original peptide in which 1 or 2 conservative substitutions were made. Thus, the analog consists of the amino acid sequence of the original peptide with 1 or 2 conservative substitutions.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-cthynyl-phenylalanine, p-propargly-oxy-phenylalanine, m-cthynyl-phenylalanine, p-bromophenylalanine, p-iodophenylalanine, p-azidophenylalanine, p-acctylphenylalanine, azidonorleucine, 6-cthynyl-tryptophan, 5-cthynyl-tryptophan, 3-(6-chloroindolyl) alanine, 3-(6-bromoindolyl)alanine, 3-(5-bromoindolyl) alanine, azidohomoalaninc, p-chlorophenylalanine, α-aminocaprylic acid, O-methyl-L-tyrosine, N-acetylgalactosamine-a-threonine, and N-acetylgalactosamine-α-serine. According to one embodiment, the substitution is substitution with a non-natural amino acid.

In some embodiments, the peptide comprises an amino acid sequence selected from the group consisting of: KFPDLDSRRLPHMSL (SEQ ID NO: 1); LATTHMVFSPDH (SEQ ID NO: 2); PSSNLESTPLSLL (SEQ ID NO: 3); SSLMTTQLIATSI (SEQ ID NO: 4); PELDSKPYFPPL (SEQ ID NO: 5); ELVTASMPRPNN (SEQ ID NO: 6); SLESSPMAQLPQ (SEQ ID NO: 7); SELRSTPLLVPS (SEQ ID NO: 8); LQIQSWSSSP (SEQ ID NO: 9); STMTILGTGS (SEQ ID NO: 10); TETSLRIVSTNP (SEQ ID NO: 11); LSIVSGSALNHL (SEQ ID NO: 12); and LTLVSERPMI (SEQ ID NO: 13) or a salt thereof. In some embodiments, the peptide comprises an amino acid sequence selected from the group consisting of SEQ ID NO: 1-13. In some embodiments, the peptide consists of an amino acid sequence selected from the group consisting of SEQ ID NO: 1-13. In some embodiments, the peptide comprises or consists of SEQ ID NO: 1. In some embodiments, the peptide comprises or consists of SEQ ID NO: 2. In some embodiments, the peptide comprises or consists of SEQ ID NO: 3. In some embodiments, the peptide comprises or consists of SEQ ID NO: 4. In some embodiments, the peptide comprises or consists of SEQ ID NO: 5. In some embodiments, the peptide comprises or consists of SEQ ID NO: 6. In some embodiments, the peptide comprises or consists of SEQ ID NO: 7. In some embodiments, the peptide comprises or consists of SEQ ID NO: 8. In some embodiments, the peptide comprises or consists of SEQ ID NO: 9. In some embodiments, the peptide comprises or consists of SEQ ID NO: 10. In some embodiments, the peptide comprises or consists of SEQ ID NO: 11. In some embodiments, the peptide comprises or consists of SEQ ID NO: 12. In some embodiments, the peptide comprises or consists of SEQ ID NO: 13. In some embodiments, the peptide comprises or consists of an amino acid sequence selected from SEQ ID NO: 1 to 8 and binds human neutrophils. In some embodiments, the peptide comprises or consists of an amino acid sequence selected from SEQ ID NO: 9 to 13 and binds murine neutrophils.

As used herein the term "salts" refers to both salts of carboxyl groups and to acid addition salts of amino or guanidino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides, analogs and salts of the present invention may be produced by any method known in the art, including recombinant and synthetic methods. Synthetic methods include exclusive solid phase synthesis, partial solid phase synthesis, fragment condensation, or classical solution synthesis. Solid phase peptide synthesis procedures are well known to one skilled in the art. Synthetic methods to produce peptides include but are not limited to FMOC solid phase peptide synthesis described, for example in Fields G. B., Noble R., Int. J. Pept. Protein Res., 35: 161-214, 1990.

In some embodiments, synthetic peptides are purified by preparative high-performance liquid chromatography and the peptide sequence is confirmed via amino acid sequencing by methods known to one skilled in the art.

In some embodiments, recombinant protein techniques, well known in the art, are used to generate peptides and peptide multimers (consisting of non-branched structures) of the present invention.

According to some embodiments, the peptide comprises at most 500, 450, 400, 350, 300, 250, 200, 150, 100, 90, 80, 70, 60, 50, 45, 40, 35, 30, 25, 20, 15 or 10 amino acids. Each possibility represents a separate embodiment of the invention. In some embodiments, the peptide comprises at most 100 amino acids. In some embodiments, the peptide comprises at most 50 amino acids. In some embodiments, the peptide comprises at most 30 amino acids. In some embodiments, the peptide comprises up to 30 amino acids. In some embodiments, the peptide comprises at most 20 amino acids. In some embodiments, the peptide comprises at most 15 amino acids.

According to some embodiments, the peptide comprises 6-100, 6-50, 6-40, 6-30, 6-25, 6-20, 6-15, 5-12, 6-10, 10-100, 10-50, 10-40, 10-30, 10-25, 10-20, 10-15, 10-12, 12-100, 12-50, 12-40, 12-30, 12-25, 12-20, 12-15, 15-100, 15-50, 15-40, 15-30, 15-25, or 15-20, amino acids. Each possibility represents a separate embodiment of the present invention. According to some embodiments, the peptide comprises at least 6 amino acids. According to some embodiments, the peptide comprises at least 8 amino acids. According to some embodiments, the peptide comprises at least 10 amino acids. According to some embodiments, the peptide comprises at least 12 amino acids. According to some embodiments, the peptide comprises at least 15 amino acids.

According to some embodiments, the peptide is conjugated to at least one moiety capable of increasing solubility. According to some embodiments, the peptide is conjugated to at least one moiety capable of increasing permeability. According to some embodiments, the peptide is conjugated at least one moiety capable of increasing solubility or permeability. According to some embodiments, at least one is a plurality of moieties. In some embodiments, a plurality is 2. In some embodiments, a plurality is at least 2, 3, 4, 5, 6, 7, 8, 9, or 10. Each possibility represents a separate embodiment of the invention.

According to other embodiments, the peptide is conjugated to at least one linker or spacer. According to further embodiments, the peptide is conjugated to at least one moiety capable of increasing solubility or permeability and optionally to at least one linker or spacer. According to yet further embodiments, the peptide is conjugated to at least one moiety capable of increasing solubility or permeability and to at least one linker or spacer. According to yet further embodiments, the peptide is conjugated to at least one moiety capable of increasing solubility or permeability and to at least one linker or spacer, wherein the at least one moiety capable of increasing solubility or permeability and the at least one linker or spacer are covalently linked to each other.

In some embodiments, the linker is an amino acid linker. In some embodiments, the linker is a chemical linker. In some embodiments, the linker is a bond. In some embodiments, the bond is a covalent bond. In some embodiments, the bond is a peptide bond. In some embodiments, the spacer is an amino acid spacer. In some embodiments, the linker or spacer comprises at least 1, 2, 3, 4, 5, 6, 7, 8, 9 or 10 amino acids. Each possibility represents a separate embodiment of the invention. In some embodiments, the linker or spacer is a single amino acid. In some embodiments, the linker or spacer comprises at most 1, 2, 3, 4, 5, 6, 7, 8, 9, 10, 11, 12, 13, 14, 15, 20, 25, 30, 35, 40, 45, 50, 60, 70, 75, 80, 90, or 100 amino acids. Each possibility represents a separate embodiment of the invention. In some embodiments, the linker or spacer comprises at most 1 amino acid. In some embodiments, the linker or spacer comprises at most 10 amino acids.

In some embodiments, the linker is a cysteine residue. In some embodiments, the linker is a lysine residue. In some embodiments, the linker is at least one repeat of the dipeptide lysine-alanine. In some embodiments, the linker is at least two repeats of the dipeptide KA. In some embodiments, the linker is two repeats of the dipeptide KA. In some embodiments, the linker comprises or consists of KAKA (SEQ ID NO: 16).

In some embodiments, a first peptide is separated from a second peptide by a spacer. In some embodiments, a first peptide is linked to a second peptide by a linker. In some embodiments, a peptide is separated from a moiety by a spacer. In some embodiments, a peptide is linked to a moiety by a linker. In some embodiments, a first moiety and a second moiety are separated by a spacer. In some embodiments, a first moiety and a second moiety are linked by a linker. In some embodiments, the linkage is a C-terminal linkage. In some embodiments, the linkage is an N-terminal linkage. In some embodiments, the linkage is not an N-terminal linkage. In some embodiments, there is no linkage to the N-terminus of the peptide. In some embodiments, the peptide comprises a free N-terminus.

According to some embodiments, the peptide is conjugated to at least one moiety via the peptide's C-terminus. According to some embodiments, the peptide is conjugated to the at least one linker or spacer via the peptide's C-terminus. According to some embodiments, the N-terminus of the peptide is not modified. According to other embodiments, the peptide has a free amine group on its N-terminus. Without being bound to any theory or mechanism, it is speculated that the amine group in the N-terminus of the peptides may be involved in the binding to neutrophils.

Moieties capable of increasing solubility are well known in the art and any such moiety may be employed for the peptide of the invention. Moieties that are capable of increasing solubility include but are not limited to: 8-amino-3,6-dioxaoctanoic acid (Doa) residues, polyethylene-glycol (PEG) in any length and peptides comprising the amino acid sequence GGGS (SEQ ID NO: 17) or GGGGS (SEQ ID NO: 18). In some embodiments, the moiety is a DOA residue. In some embodiments, the moiety is PEG. In some embodiments, the linker comprises at least one repeat of SEQ ID NO: 17. In some embodiments, the linker comprises at least one repeat of SEQ ID NO: 18. In some embodiments, the linker comprises or consists of at least 1, 2, 3, 4, or 5 repeats of SEQ ID NO: 17. Each possibility represents a separate embodiment of the invention. In some embodiments, the linker comprises or consists of at least 1, 2, 3, 4, or 5 repeats of SEQ ID NO: 18. Each possibility represents a separate embodiment of the invention.

According to specific embodiments, the moiety capable of increasing solubility comprises an 8-amino-3,6-dioxaoctanoic acid (Doa) residue. According to some embodiments, the peptides are conjugated to 1,2,3,4 or 5 Doa residues. Each possibility represents a separate embodiment of the present invention. According to some embodiments, the peptides are conjugated to 2 Doa residues. According to further embodiments, the Doa residues are covalently connected to each other, to the peptide sequence and/or to a linker. According to some embodiments, the peptides are conjugated to two units of Doa residues covalently connected to each other. In some embodiments, the covalent linkage is a peptide linkage. In some embodiments, the peptide and the residue are in a single amino acid chain.

The terms "conjugated" or "peptide conjugate" as used herein refer to a molecule in which a peptide moiety is attached (i.e., coupled or linked), either directly or via a linker or spacer, by means of covalent chemical bonding to at least one peptidic or non-peptidic molecule.

The terms "linker" and "spacer" are used herein interchangeably and refer to any molecule that covalently binds and therefore linking two molecules. Non-limiting examples of the linker are amino acids, peptides, or any other organic substance that can be used to allow distance between two linked molecules. According to specific embodiments, the linker is a flexible linker. According to specific embodiments, the linker is a flexible peptide. According to further specific embodiments, the linker is a flexible peptide comprising at least one glycine residue. According to particular embodiments, the linker comprises plurality of Lysine residues. According to some specific embodiments, the linker comprises 3-12 Lysine residues. According to particular embodiments, the linker comprises a 3-maleimidopropionic acid (Mpa) residue.

According to some embodiments, a peptide conjugate comprising at least one peptide selected from SEQ ID NO: 1 to 13 and at least one moiety capable of increasing solubility is attached to the nanoparticle. According to other embodiments, a peptide conjugate comprising at least one peptide selected from SEQ ID NO: 1 to 13 and at least one linker or spacer is attached to the nanoparticle. According to further embodiments, the peptide conjugates comprise at least one peptide selected from SEQ ID NO: 1 to 13, at least one moiety capable of increasing solubility and optionally at least one linker or spacer. According to yet further embodiments, the peptide conjugates comprise at least one peptide selected from SEQ ID NO: 1 to 13, at least one moiety capable of increasing solubility and at least one linker or spacer. According to yet further embodiments, the peptide conjugates comprise at least one moiety capable of increasing solubility and at least one linker or spacer, wherein the at least one moiety capable of increasing solubility and the at least one linker or spacer are covalently linked to each other.

According to some embodiments, the peptide conjugates comprise at least one peptide selected from SEQ ID NO: 1 to 13 and 1,2,3,4 or 5 units of a Doa residue. Each possibility represents a separate embodiment of the present invention. According to further embodiments, the peptide conjugates comprise at least one peptide selected from SEQ ID NO: 1 to 13 and 2, 3, 4 or 5 units of a Doa residue, wherein the Doa residues are covalently connected to each other to the peptide sequence and/or to a linker.

According to further embodiments, the peptide conjugates comprise at least one peptide selected from SEQ ID NO: 1 to 13, at least one Doa residue and at least one Mpa residue.

According to some embodiments, the peptide conjugate comprises at least one moiety capable of increasing solubility, wherein the at least one moiety is conjugated to the peptide via the peptide's C-terminus. According to some embodiments, peptide conjugate comprises at least one linker or spacer, wherein the at least one linker or spacer is conjugated to the peptide via the peptide's C-terminus. According to some embodiments, the N-terminus of the peptide conjugate is not modified. According to other embodiments, the peptide conjugate has a free amine group on its N-terminus.

According to some embodiments, the peptide conjugate has a structure according to Formula V:

Peptide-Doa-Doa-C (Formula V) wherein "C" is a Cysteine residue, and wherein "Peptide" denotes a peptide of the invention or a salt thereof. In some embodiments, "Peptide" denotes a peptide of the invention or a salt thereof.

According to some embodiments, a peptide multimer, comprising a plurality of peptides is attached to the nanoparticle.

According to some embodiments, the plurality of peptides is a plurality of same peptide. According to some embodiments, the plurality of peptides is a plurality of different peptides. According to some embodiments, the peptides are identical or different peptides. According to some embodiments, the present invention provides a peptide multimer comprising a plurality of identical or different peptides selected from peptides of the invention or salts thereof. According to other embodiments, the present invention provides a peptide multimer for use in targeting to human neutrophils, wherein the peptide multimer comprises a plurality of identical or different peptides selected from the group consisting of SEQ ID NO: 1-8 or salts thereof. According to other embodiments, the present invention provides a peptide multimer for use in targeting to murine neutrophils, wherein the peptide multimer comprises a plurality of identical or different peptides selected from the group consisting of SEQ ID NO: 9-13 or salts thereof.

The terms "peptide multimer" and "multimeric peptide" are used interchangeably herein and refer to a construct that contains a plurality (at least two, typically at least three or more) of peptides, not necessarily adjacent.

According to some embodiments, the peptide multimer is a branched molecule. According to other embodiments, the peptide multimer is a non-branched molecule. According to other embodiments, the peptide multimer is a linear molecule. According to other embodiments, the peptide multimer is a circular molecule.

According to some embodiments, the peptide multimer comprises at most 4, 6, 8, 10, 12, 14, 16, 18, 20, 25, 30, 35, 40, 45 or 50 peptides. Each possibility represents a separate embodiment of the present invention. According to some embodiments, the peptide multimer comprises at least 2, 4, 6, 8, 10, 12, 14, or 16 peptides. Each possibility represents a separate embodiment of the present invention. According to some embodiments, the peptide multimer comprises 2-20, 2-16, 2-14, 2-12, 2-10, 2-8, 2-6 or 2-4 identical or different peptides. Each possibility represents a separate embodiment of the present invention. According to some embodiments, the peptide multimer comprises 2-20, 2-16, 2-14, 2-12, 2-10, 2-8, 2-6 or 2-4 peptides. Each possibility represents a separate embodiment of the present invention. According to some embodiments, the peptide multimer comprises 2-20 peptides. According to some embodiments, the peptide multimer comprises 2-4 peptides. According to some embodiments, the peptide multimer comprises 2 peptides. According to some embodiments, the peptide multimer comprises 4 peptides. According to some embodiments, the peptide multimer comprises 16 peptides. According to specific embodiments, the peptide multimer comprises 4 identical or different peptides.

According to some embodiments, the peptides in the peptide multimer are covalently linked to each other directly or through a linker or spacer. According to other embodiments, the peptides in the peptide multimer are covalently linked to a scaffold directly or through a linker or spacer.

According to some embodiments, the peptide multimer comprises a plurality of identical or different peptide conjugates. According to some embodiments, the peptide multimer comprises peptide conjugates comprising at least one peptide selected from SEQ ID NO: 1-8. According to some embodiments, the peptide multimer comprises peptide conjugates comprising at least one peptide selected from SEQ ID NO: 9-13. According to some embodiments, the peptide multimer comprises 2-20, 2-16, 2-14, 2-12, 2-10, 2-8, 2-6 or 2-4 identical or different peptide conjugates comprising at least one peptide selected from SEQ ID NO: 1-8. According to other embodiments, the peptide multimer comprises 2-20, 2-16, 2-14, 2-12, 2-10, 2-8, 2-6 or 2-4 identical or different peptide conjugates comprising at least one peptide selected from SEQ ID NO: 9-13. According to specific embodiments, the peptide multimer comprises 4 identical or different peptide conjugates.

According to some embodiments, the peptide conjugates in the peptide multimer are covalently linked to each other directly or through a linker or spacer. According to other embodiments, the peptide conjugates in the peptide multimer are covalently linked to a scaffold directly or through a linker or spacer. According to further embodiments, the peptide conjugates in the peptide multimer are non-covalently linked to a scaffold directly or through a linker or spacer. According to some embodiments, the scaffold is a branched scaffold. According to other embodiments, the scaffold is a non-branched scaffold.

According to some embodiments, each one of the peptides or peptide conjugates is bound to the nanoparticle directly or via a linker or spacer. In some embodiments, a peptide monomer is linked or bound to the nanoparticle directly or via a linker or spacer. In some embodiments, the linker is a cysteine residue. In some embodiments, the thiol group of the cysteine residue is reacted with a maleimide on the nanoparticle. According to other embodiments, the peptides or peptide conjugates are covalently attached to each other and at least one peptide/peptide conjugate is bound to the nanoparticle directly or via a linker or spacer. According to some embodiments, each one of the peptides or peptide conjugates is bound to a scaffold directly or via a linker or spacer. According to other embodiments, the peptides or peptide conjugates are covalently attached to each other and at least one peptide/peptide conjugate is bound to a scaffold directly or via a linker or spacer.

According to some embodiments, the scaffold is a peptidic or polypeptidic scaffold. According to other embodiments, the peptidic or polypeptidic scaffold connects the peptides to each other on a single location in the scaffold, or to a different location on a scaffold. Each possibility represents a separate embodiment of the invention. According to some embodiments, the scaffold comprises at least one Lysine (Lys) residue. According to other embodiments, the scaffold comprises at least three Lys residues. According to further embodiments, the at least three Lys residues are connected together by amide bonds to form a branched multimeric scaffold. According to some embodiments, at least one amide bond is formed between the epsilon amine of a Lys residue and the carboxy group of another Lys residue.

According to some embodiments, the peptide multimer comprises the molecule Mpa-Cysteine-peptide.

According to some embodiments, the peptide multimer comprises a molecule of the scheme:

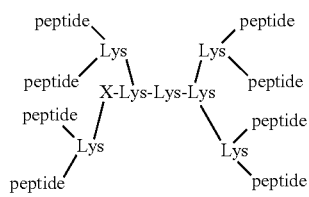

wherein X represents the peptide's C-terminus selected from carboxy acid, amide or alcohol group and optionally a linker or spacer, and each "peptide" independently denotes a peptide of the invention or a salt thereof.

According to some specific embodiments, at least one of the peptides is present in multiple copies. According to some embodiments, the multiple copies are linked thereby forming a multi-target peptide multimer. According to some embodiments, the peptide copies are linked through a linker. According to other embodiments, the peptide copies are linked directly. According to further embodiments, the multimer comprises copies linked both directly and via a linker.

According to some embodiments, the peptide multimer comprises a plurality of neutrophil-binding peptides arranged in an alternating sequential polymeric structure B(X1X2X3 . . . Xm)nB or in a block copolymer structure B(X1)nZ(X2)nZ(X3)nZ . . . (Xm)n, wherein B is an optional sequence of 1-10 amino acid residues; n is at each occurrence independently an integer of 2-50; m is an integer of 3-50; each of X1, X2 . . . Xm is an identical or different peptide of the invention; Z at each occurrence is a bond or a spacer of 1-4 amino acid residues. Each possibility represents a separate embodiment of the present invention.

The term "block copolymer structure" means that all the copies of a single peptide contained in the multimer are arranged adjacently.

According to some embodiments, the scaffold comprises or formed from a polyethylene glycol (PEG) molecule(s) or a modified PEG molecule(s). According to certain embodiments, the scaffold comprises a branched PEG molecule. According to some embodiments, the branched molecule comprises at least two sites available to bind a peptide of the present invention. According to other embodiments, the scaffold comprises from 2 to 100, 3 to 90, 4 to 60, 5 to 50, 6 to 40, 7 to 35, 8 to 30, 9 to 25 or 10 to 20, or 2 to 50 sites available to bind a peptide.

According to some embodiments, the PEG molecule is a branched molecule, comprising at least two separate connections to a peptide. According to other embodiments, the PEG is bound to additional PEG molecules. According to certain embodiments, multiple PEG molecules are bound to provide a multi-armed PEG molecule. According to certain embodiments, the peptides are connected to the PEG scaffold through amide bonds formed between amino groups of an NH2-PEG molecule. According to yet other embodiments, at least one peptide is connected to PEG scaffold though a Lys residue.

According to some embodiments, the peptide multimer comprises a branched scaffold comprising at least one Lys residue linked to the peptides or peptide conjugates directly or through a spacer or linker. According to specific embodiments, the peptide multimer comprises a branched scaffold comprising at two Lys residues linked to the peptides or peptide conjugates directly or through a spacer or linker. According to further specific embodiments, the peptide multimer comprises a branched scaffold comprising the amino acid sequence Lys-Ala-Lys-Ala (KAKA, SEQ ID NO: 16) linked to the peptides or peptide conjugates directly or through a spacer or linker.

According to some embodiments, the peptide multimer further comprises a biotin moiety covalently attached to the peptide multimer directly or via a spacer or linker. According to some embodiments, the biotin is attached to the peptide multimer through the C-terminus. The biotin moiety makes the peptide multimer accessible for fluorescent detection and manipulation. According to other embodiments, the peptide multimer further comprises a biotin moiety, wherein the biotin moiety is non-covalently attached to the peptide multimer. According to some embodiments, the peptide multimer further comprises an avidin moiety attached to the peptide multimer directly or via a spacer or linker. According to some embodiments, the peptide multimer further comprises a streptavidin moiety attached to the peptide multimer directly or via a spacer or linker. According to further embodiments, the peptide multimer comprises a biotin moiety and an avidin/streptavidin moiety attached to each other through biotin-avidin interactions.

According to some embodiments, the multimeric peptide is homo-multimeric. According to other embodiments, the multimeric peptide is hetero-multimeric.

As used herein, the term "homo-multimeric" refers to a multimeric peptide comprising multiple copies of a single peptide. According to some embodiments, the multimeric peptide comprises 2-20, 2-16, 2-14, 2-12, 2-10, 2-8, 2-6 or 2-4 identical peptides.

The term "hetero-multimeric" as used herein refers to a multimeric peptide comprising one or more copies of at least two different peptides. The term "different peptides" refers to peptides having different sequence and not to two copies of the same peptide. According to some embodiments, the multimeric peptide comprises one or more copies of at least two different peptides of the invention. According to specific embodiments, the multimeric peptide comprises one or more copies of at least two different peptides of the invention.

According to some embodiments, the hetero multimeric peptide comprises 2, 3, 4, 5 ,6, 7 or 8 different peptide sequences of the invention or a salt thereof.

It has been shown that a peptide multimer comprising 4 copies of a single neutrophil-binding peptide, binds more efficiently to circulating neutrophils than a monomer of the peptide. Without being bound to any theory or mechanism, it is believed that a hetero-multimeric peptide comprising at least two substantially different peptides would target even higher percent of neutrophils than a homo-multimeric peptide.

According to some embodiments, the hetero-multimeric peptide comprises 2-20, 2-10 or 2-5 copies of at least one of the different peptides. According to other embodiments, the hetero-multimeric peptide comprises 2-20, 2-10 or 2-5 copies of at least two of the different peptides. According to further embodiments, the hetero-multimeric peptide comprises 2-20, 2-10 or 2-5 copies of at least three of the different peptides. Each possibility represents a separate embodiment of the present invention.

According to specific embodiments, the peptide multimer is a tetramer peptide presenting the neutrophil-binding peptide on 4 branches. According to further embodiments, at least one peptide in the tetramer has a free amine group on its N-terminus. According to yet further embodiments, each one of the neutrophil-binding peptides in the tetramer has a free amine group on the N-terminus. According to specific embodiments, the multimer peptide is a tetramer peptide presenting 4 copies of one neutrophil-binding peptide on 4 branches. According to further specific embodiments, the multimer peptide is a tetramer peptide presenting 4 copies of one neutrophil-binding peptide on 4 branches, wherein at least one copy of the neutrophil-binding peptide has a free amine group on its N-terminus. According to further embodiments, the multimer peptide is a tetramer peptide presenting 4 copies of one neutrophil-binding peptide on 4 branches, wherein each one of the copies of the neutrophil-binding peptide has a free amine group on its N-terminus.

According to some embodiments, the peptide multimer comprises a structure according to Formula VI:

(SEQ ID NO: 16)

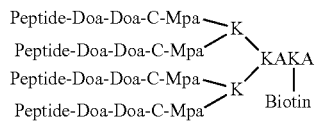

Formula VI wherein each "Peptide" independently denotes a peptide of the invention or a salt thereof.

According to some embodiments, the peptide multimer comprises a structure according to Formula VI, wherein each "Peptide" independently denotes a peptide of the invention or a salt thereof, wherein at least 2 peptides are different. According to other embodiments, the peptide multimer comprises a structure according to Formula VI, wherein each "Peptide" independently denotes a peptide of the invention or a salt thereof, wherein at least 3 peptides are different. According to other embodiments, the peptide multimer comprises a structure according to Formula VI, wherein each "Peptide" independently denotes a different peptide sequence, wherein each peptide sequence comprises a sequence selected from the group consisting of SEQ ID NO: 1 to 13 or a salt thereof. According to some embodiments, the peptide multimer comprises a structure according to Formula VI, wherein each "Peptide" independently denotes a peptide of the invention or a salt thereof, wherein at least 2 peptides are identical. According to other embodiments, the peptide multimer comprises a structure according to Formula VI, wherein each "Peptide" independently denotes a peptide of the invention or a salt thereof, wherein at least 3 peptides are identical. According to yet other embodiments, the peptide multimer comprises a structure according to Formula VI, wherein "Peptide" denotes a peptide of the invention or a salt thereof. According to other embodiments, the peptide multimer comprises a structure according to Formula VI, wherein each "Peptide" independently denotes a peptide of the invention or a salt thereof, wherein 4 peptides are identical.

According to some embodiments, the peptide multimer comprises a structure according to Formula VII:

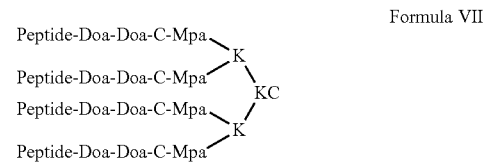

Formula VII wherein each "Peptide" independently denotes a peptide of the invention or a salt thereof.

According to some embodiments, the peptide multimer comprises a structure according to Formula VII, wherein each "Peptide" independently denotes a peptide of the invention or a salt thereof, wherein at least 2 peptides are different. According to other embodiments, the peptide multimer comprises a structure according to Formula VII, wherein each "Peptide" independently denotes a peptide of the invention or a salt thereof, wherein at least 3 peptides are different. According to other embodiments, the peptide multimer comprises a structure according to Formula VII, wherein each "Peptide" independently denotes a different peptide sequence, wherein each peptide sequence comprises a sequence selected from the group consisting of SEQ ID NO: 1 to 13 or a salt thereof. According to some embodiments, the peptide multimer comprises a structure according to Formula VII, wherein each "Peptide" independently denotes a peptide of the invention or a salt thereof, wherein at least 2 peptides are identical. According to other embodiments, the peptide multimer comprises a structure according to Formula VII, wherein each "Peptide" independently denotes a peptide of the invention or a salt thereof, wherein at least 3 peptides are identical. According to yet other embodiments, the peptide multimer comprises a structure according to Formula VII, wherein "Peptide" denotes a peptide of the invention or a salt thereof. According to other embodiments, the peptide multimer comprises a structure according to Formula VII, wherein each "Peptide" independently denotes a peptide of the invention or a salt thereof, wherein 4 peptides are identical.

In some embodiments, a peptide complex comprising at least two peptide multimers is attached to the nanoparticle. As used herein, the term "peptide complex" refers to a construct that contains a plurality (at least two, typically at least three or more) of identical or different peptide multimers, not necessarily adjacent. According to some embodiments, the peptide complex comprises at least two peptide multimers, wherein the peptide multimers comprise at least one peptide of the invention or a salt thereof. According to certain embodiments, the present invention provides a peptide complex for use in targeting to human neutrophils wherein the peptide complex comprises at least two peptide multimers, wherein the peptide multimers comprise at least one peptide comprising a sequence selected from SEQ ID NO: 1 to 13 or a salt thereof. According to some embodiments, the peptide multimers in the peptide complex are covalently connected to each other directly or via a linker or spacer. According to some embodiments, the linker or spacer is selected from the group consisting but not limited to amino acids, peptides, and any other organic substance that can be used to allow distance between two linked molecules. According to other embodiments, the peptide multimers in the peptide complex are non-covalently attached to each other. According to some embodiments, the peptide multimers in the peptide complex are non-covalently attached to each other through a biotin-avidin interactions. According to some embodiments, the peptide complex comprises at least two biotin moieties and an avidin/streptavidin moiety, wherein the at least two biotin moieties are covalently attached to the peptide multimers, and wherein the avidin/streptavidin moiety is non-covalently attached to the biotin moieties. According to specific embodiments, the peptide complex comprises 4 peptide multimers and an avidin/streptavidin moiety, wherein each one of the peptide multimers is covalently attached to a biotin moiety, and wherein the 4 peptide multimers are non-covalently attached to the avidin/streptavidin moiety.

According to some embodiments, the peptide and/or nanoparticle is a peptide and/or nanoparticle disclose in International Patent Publication WO2022003674 herein incorporated by reference in its entirety.

Compositions

In some embodiments, the compound of the invention is in a composition. In some embodiments, a nanoparticle of the invention is in a composition. In some embodiments, the composition is a pharmaceutical composition. In some embodiments, the composition comprises the compound of the invention, a pharmaceutically acceptable salt thereof or both. In some embodiments, the pharmaceutical composition of the invention comprises a therapeutically effective amount of the compound of the invention and/or any pharmaceutically acceptable salt thereof and/or derivative thereof. In some embodiments, the composition comprises the nanoparticle of the invention, a pharmaceutically acceptable salt thereof or both. In some embodiments, the pharmaceutical composition of the invention comprises a therapeutically effective amount of the nanoparticle of the invention and/or any pharmaceutically acceptable salt thereof and/or derivative thereof. In some embodiments, therapeutically effective amount is sufficient for reduction of at least one symptom, or for substantial reduction in the severity and/or inhibition of the progression of a disease, disorder, or condition as described hereinabove. In some embodiments, therapeutically effective amount is sufficient to inhibit neutrophils. In some embodiments, the therapeutically effective amount can be determined as described hereinbelow.

In some embodiments, there is provided herein a composition comprising one or more compounds of the invention, including any salt (e.g., a pharmaceutically acceptable salt), any tautomer, and/or any stereoisomer thereof. In some embodiments, the compound as described hereinabove is the only active ingredient within the composition of the invention (e.g., pharmaceutical composition).

Non-limiting examples of pharmaceutically acceptable salts include but are not limited to: acetate, aspartate, benzenesulfonate, benzoate, bicarbonate, carbonate, halide (such as bromide, chloride, iodide, fluoride), bitartrate, citrate, salicylate, stearate, succinate, sulfate, tartrate, decanoate, edetate, fumarate, gluconate, and lactate or any combination thereof.

In some embodiments, the liposomal composition comprises a salt of the compound, wherein the salt is sulfate, citrate, sucrosofate, a salt with a phosphorylated or sulfated polyol, or a salt with a phosphorylated or sulfated polyanionic polymer. In some embodiments, the liposomal composition comprises a sulfate salt of the compound.

In some embodiments, the composition comprises a pharmaceutically acceptable carrier, excipient or adjuvant. As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

In some embodiments, the pharmaceutical composition is for use in treating a disease or disorder. In some embodiments, the pharmaceutical composition is for use in treating a medical condition in which neutrophils are involved in the pathogenesis. In some embodiments, the pharmaceutical composition is for use in treating a neutrophil-associated disease or condition.

In some embodiments, a medical condition is a disease. In some embodiments, a medical condition is a condition. In some embodiments, a medical condition is a disorder. In some embodiments, the medical condition is a neutrophil-associated disease or condition. In some embodiments, the medical condition is a disease or condition mediated by neutrophils. In some embodiments, the medical condition is a disease or condition made worse by neutrophils. In some embodiments, the medical condition is a disease or condition associated with accumulation of neutrophils. In some embodiments, the accumulation is at a diseased tissue or site. In some embodiments, the accumulation is at an injured tissue or site. In some embodiments, the medical condition is selected from the group consisting of cancer, infectious disease, inflammatory disease or disorder and autoimmune disease or disorder. In some embodiments, the medical condition is cancer. In some embodiments, the medical condition is inflammation. In some embodiments, the medical condition is an inflammatory disease or condition. In some embodiments, the inflammatory disease or condition is an autoimmune inflammatory disease or condition.

In some embodiments, the pharmaceutical composition is for use in treating a neutrophil-associated disease or condition. In some embodiments, the pharmaceutical composition is for use in treating a disease or condition associated with accumulation of neutrophils to a diseased or injured tissue or site. In some embodiments, the disease or condition is selected from the group consisting of: a cancer, an inflammatory disease or condition and an inflammatory autoimmune disease or condition. In some embodiments, the disease or condition is an inflammatory disease or condition. In some embodiments, the disease or condition is cancer. In some embodiments, the disease or condition is inflammation. In some embodiments, the inflammation is neutrophil induced inflammation. In some embodiments the disease or condition is a skin disease. In some embodiments, the inflammatory disease or condition is inflammatory skin disease. In some embodiments, the skin disease is an inflammatory skin disease. In some embodiments, the skin disease comprises neutrophilic dermatoses (ND). In some embodiments, ND comprises neutrophils accumulation within a skin layer. In some embodiments the skin disease is selected from the group consisting of: Sweet's syndrome (SS), pyoderma gangrenosum (PG), rheumatoid neutrophilic dermatitis, bowel-associated dermatosis-arthritis syndrome, subcorneal pustular dermatosis (Sneddon Wilkinson), acute generalized exanthematous pustulosis (AGEP), acrodermatitis continua of Hallopeau (ACH), palmoplantare pustuloses (PPP), pustular bacterid (PB), neutrophilic eccrine hidradenitis, Hidradenitis suppurativa (HS), and Behçet's disease. In some embodiments the skin disease is selected from the group consisting of: SS, PPP, PG, and HS.

In some embodiments, the medical condition is a disease in which the release of neutrophil extracellular nets (NETosis) is part of the pathophysiology. In some embodiments, the medical condition is a disease characterized by excessive neutrophil-mediated tissue damage. Non limiting examples of disease characterized by excessive neutrophil-mediated tissue damage are pulmonary diseases such as acute respiratory distress syndrome (ARDS) and chronic obstructive pulmonary disease (COPD). In some embodiments, the medical condition is ARDS. In some embodiments, the medical condition is COPD. In some embodiments, the disease is COPD. In some embodiments, the medical condition is selected from the group consisting of: a cancer, an inflammatory disease, condition or disorder, and an autoimmune disease, condition or disorder. According to some embodiments, the autoimmune disease, condition or disorder is an inflammatory autoimmune disease, condition or disorder. According to other embodiments, the medical disease is selected from the group consisting of thrombosis, Alzheimer disease, and a neutrophil-mediated skin disease. According to some embodiments, the medical condition is neutrophil-mediated skin disease. According to some embodiments, the medical condition is cancer. According to some embodiments, the medical condition is an inflammatory condition. According to some embodiments, the medical condition is an inflammatory disease. According to some embodiments, the inflammatory disease or condition is selected from chronic obstructive pulmonary disease (COPD), inflammatory bowel disease (IBD) and peritonitis. According to some embodiments, the inflammatory disease or condition is COPD. According to some embodiments, the inflammatory disease or condition is IBD. According to some embodiments, IBD comprises Crohn's disease. According to some embodiments, IBD comprises colitis. In some embodiments, the inflammatory disease or condition is colitis. According to some embodiments, the inflammatory disease or condition is peritonitis. In some embodiments, IBD comprise colitis and Chron's disease. In some embodiments, IBD is colitis. In some embodiments, colitis is ulcerative colitis.

According to some embodiments, the inflammatory disease is a disease in which neutrophils are involved in the pathogenesis. According to some embodiments, the inflammatory disease or disorder is selected from the group consisting of peritonitis, colitis, vasculitis, atherosclerosis, chronic obstructive pulmonary disease (COPD), acute respiratory distress syndrome (ARDS), bronchiectasis, neutrophilic asthma, rheumatoid arthritis (RA), lupus, cystic fibrosis (CF), sepsis, multiple sclerosis, psoriasis and traumatic injury. Each possibility represents a separate embodiment of the present invention. According to some embodiments, the disease or disorder is Systemic Lupus Erythrocytes (SLE). According to some embodiments, the disease or disorder is rheumatoid arthritis (RA). According to some embodiments, the disease or disorder is gout. According to some embodiments, the disease or disorder is inflammatory arthritis.

According to some embodiments, the disease is cancer. In some embodiments, the cancer is a solid tumor. In some embodiments, the cancer is solid cancer. In some embodiments, the cancer is a hematological cancer. According to some embodiments, the cancer is selected from solid tumor cancer and hematological cancer. According to some embodiments, the solid cancer is selected from the group consisting of breast cancer, lung cancer, colon cancer, pancreatic cancer, liver cancer, head and neck cancer and kidney cancer. Each possibility represents a separate embodiment of the present invention. According to some embodiments the hematological cancer is leukemia. According to some embodiments the cancer is liver cancer. In some embodiments, liver cancer comprises hepatocellular carcinoma (HCC). In some embodiments, the cancer comprises head and neck squamous cell carcinoma (HNSCC). According to some embodiments the cancer is kidney cancer. In some embodiments, kidney cancer is selected from renal cell cancer (RCC), transitional cell cancer (TCC), and Wilms tumor.

In some embodiments, the pharmaceutical composition of the invention is for use as a medicament. In some embodiments, the composition is formulated for systemic administration. In some embodiments, the composition is formulated for administration to a subject. In some embodiments, the subject is a human. In some embodiments, the composition is formulated for intravenous administration. In some embodiments, the composition is formulated for subcutaneous administration. In some embodiments, the composition is formulated for topical administration. In some embodiments, the composition is formulated for oral administration. In some embodiments, the composition is formulated for rectal administration. In some embodiments, the composition is formulated for inhalation. In some embodiments, the composition is formulated for intratumoral administration. In some embodiments, the composition is formulated for local administration to a site of inflammation.

The pharmaceutical composition of the present invention may be administered by any know method. The terms "administering" or "administration of" a substance, a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

According to some embodiments, the pharmaceutical composition is administered by an invasive mode of administration such as intramuscularly, intravenously, intra-arterially, intraarticularly or parenterally. According to specific embodiments, the pharmaceutical composition is administered intravenously. According to some embodiments, the composition is administered systemically. According to some embodiments, the composition is administered to a site of inflammation. In some embodiments, the composition is formulated for administration to a subject. According to some embodiments, the composition is formulated for systemic administration. According to some embodiments, the composition is formulated for administration to a site of inflammation. In some embodiments, the composition is formulated for administration to a disease site. In some embodiments, the composition is formulated for intratumoral administration.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, it will be determined by the physician in the end. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

For example, the term "pharmaceutically acceptable" can mean approved by a regulatory agency of the Federal or a state government or listed in the U.S. Pharmacopcia or other generally recognized pharmacopeia for use in animals, and more particularly in humans. In some embodiments, the compound of the invention is referred to herein as an active ingredient of a pharmaceutical composition.

In some embodiments, the pharmaceutical composition comprising the compound of the invention is in a unit dosage form. In some embodiments, the pharmaceutical composition is prepared by any of the methods well known in the art of pharmacy. In some embodiments, the unit dosage form is in the form of a tablet, capsule, lozenge, wafer, patch, ampoule, vial or pre-filled syringe.

In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems. In some embodiments, the effective dose is determined as described hereinabove.

In another embodiment, the pharmaceutical composition of the invention is administered in any conventional oral, parenteral or transdermal dosage form.

Pharmaceutically Acceptable Salts

In some embodiments, the compounds of the present invention can exist in free form for treatment, or as a pharmaceutically acceptable salt.

As used herein, the term "pharmaceutically acceptable salt" refers to any non-toxic salt of a compound of the present invention that, upon administration to a subject, e.g., a human, is capable of providing, either directly or indirectly, a compound of this invention or an inhibitory active metabolite or residue thereof. For example, the term "pharmaceutically acceptable" can mean approved by a regulatory agency of the Federal or a state government or listed in the U. S. Pharmacopeia or other generally recognized pharmacopeia for use in animals, and more particularly in humans.

Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

In some embodiments, the compounds described herein are chiral compounds (i.e., possess an asymmetric carbon atom). In some embodiments, diastereomers, geometric isomers and individual isomers are encompassed within the scope of the present invention. In some embodiments, a chiral compound described herein is in form of a racemic mixture. In some embodiments, a chiral compound is in form of a single enantiomer, with an asymmetric carbon atom having the R configuration. In some embodiments, a chiral compound is in form of a single enantiomer, with an asymmetric carbon atom having the S configuration as described hereinabove.

In some embodiments, a chiral compound is in form of a single enantiomer with enantiomeric purity of more than 70%. In some embodiments, a chiral compound is in form of a single enantiomer with enantiomeric purity of more than 80%. In some embodiments, a chiral compound is in form of a single enantiomer with enantiomeric purity of more than 90%. In some embodiments, a chiral compound is in form of a single enantiomer with enantiomeric purity of more than 95%.

In some embodiments, the compound of the invention comprising an unsaturated bond is in a form of a trans-, or cis-isomer. In some embodiments, the compound of the invention is in a form of a single isomer with isomeric purity of more than 70%, more than 80%, more than 90%, between 90 and 99%, between 95 and 99%, 97 and 99%, between 95 and 97%, including any range between. In some embodiments, a chiral compound is in form of Z-isomer with isomeric purity of more than 95%. In some embodiments, the composition of the invention comprises a mixture of cis- and trans-isomers, as described hereinabove.

In some embodiments, the compounds described herein can exist in unsolvated form as well as in solvated form, including hydrated form. In general, the solvated form is equivalent to the unsolvated form and is encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this invention. Such compounds are useful, for example, as analytical tools or probes in biological assays.

In another embodiment, the compositions of the invention take the form of solutions, suspensions, emulsions, tablets, pills, capsules, powders, gels, creams, ointments, foams, pastes, sustained-release formulations and the like. In another embodiment, the compositions of the invention can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E.W. Martin, the contents of which are hereby incorporated by reference herein. Such compositions will contain a therapeutically effective amount of the polypeptide of the invention, preferably in a substantially purified form, together with a suitable amount of carrier so as to provide the form for proper administration to the subject.

Method of Use

According to some embodiments, the present invention provides a method of treating, preventing or ameliorating a neutrophil-associated disease or condition in a subject in need thereof, the method comprising administering to the subject the pharmaceutical composition described hereinabove. In some embodiments, the disease or condition is in a subject in need thereof. In some embodiments, the method comprises administering the compound. In some embodiments, the method comprises administering the nanoparticle. In some embodiments, the method comprises administering the composition.

In some embodiments, the disease or condition is selected from the group consisting of: a cancer, an inflammatory disease or condition and an inflammatory autoimmune disease or condition. In some embodiments, the disease or condition is a neutrophil-associated disease or condition. In some embodiments, the disease or condition is a disease or condition characterized by neutrophil pathology. In some embodiments, the disease or condition is a disease or condition characterized by neutrophil activity. In some embodiments, the disease or condition is a disease or condition characterized by neutrophil is a disease or condition treatable by inhibiting neutrophils. In some embodiments, inhibiting neutrophils comprises inhibiting neutrophil activation. In some embodiments, inhibiting neutrophils comprises inhibiting neutrophil degranulation. In some embodiments, inhibiting neutrophils comprises inhibiting neutrophil NETosis. In some embodiments, inhibiting neutrophils comprises inhibiting neutrophil exocytosis. In some embodiments, inhibiting neutrophils comprises inhibiting reactive oxygen species (ROS) production. In some embodiments, ROS production is ROS secretion. In some embodiments, inhibiting neutrophils comprises inhibiting neutrophil mediated killing. In some embodiments, inhibiting neutrophils comprises inhibiting neutrophil mediated cytotoxicity. In some embodiments, inhibiting neutrophils comprises inhibiting protease secretion. In some embodiments, inhibiting neutrophils comprises inhibiting NET production. In some embodiments, inhibiting neutrophils does not inhibit NET production. In some embodiments, inhibiting neutrophils comprises inhibiting inflammation. In some embodiments, inflammation is in the subject.

In some embodiments, the cancer comprises high neutrophil burden. In some embodiments, high neutrophil burden comprises elevated numbers of neutrophils, increased activity of neutrophils, or both. In some embodiments, a neutrophil burden comprises the ratio between the number of neutrophils to the number of lymphocytes. In some embodiments, a neutrophil burden is compared to a predetermined threshold. In some embodiments, a high neutrophil burden is above a predetermined threshold. In some embodiments, a neutrophil burden is examined in a biopsy obtained from the subject in need thereof. In some embodiments, a neutrophil burden is examined within a tumor tissue. In some embodiments a neutrophil burden is examined in a tumor microenvironment (TME).

According to some embodiments, the cancer is selected from solid tumor cancer and hematological cancer. Each possibility represents a separate embodiment of the present invention. According to some embodiments, the solid cancer is selected from the group consisting of breast cancer, lung cancer, colon cancer, pancreatic cancer, liver cancer, head and neck cancer and kidney cancer. According to some embodiments the hematological cancer is leukemia. According to some embodiments the cancer is kidney cancer. In some embodiments, kidney cancer comprises renal cell carcinoma (RCC). In some embodiments, the cancer comprises hepatocellular carcinoma (HCC). In some embodiments, the cancer comprises head and neck squamous cell carcinoma (HNSCC). Each possibility represents a separate embodiment of the present invention.

In some embodiments, treating cancer comprises administering the composition disclosed herein and an immune checkpoint inhibitor. In some embodiments, the immune checkpoint inhibitor comprises immune checkpoint blockade. In some embodiments, the immune checkpoint is programmed cell death protein 1 (PD-1), programmed cell death protein ligand 1 (PD-L1), cytotoxic T-lymphocyte-associated protein 4 (CTLA-4), or any combination thereof.

According to some embodiments, the inflammatory disease is a disease in which neutrophils are involved in the pathogenesis. According to some embodiments, the inflammatory disease or disorder is selected from the group consisting of peritonitis, colitis, vasculitis, atherosclerosis, chronic obstructive pulmonary disease (COPD), acute respiratory distress syndrome (ARDS), bronchiectasis, neutrophilic asthma, rheumatoid arthritis (RA), lupus, cystic fibrosis (CF), sepsis, multiple sclerosis, psoriasis and traumatic injury. Each possibility represents a separate embodiment of the present invention. According to some embodiments, the disease or disorder is Systemic Lupus Erythrocytes (SLE). According to some embodiments, the disease or disorder is rheumatoid arthritis (RA).

In some embodiments, the inflammatory disease or condition is selected from chronic obstructive pulmonary disease (COPD), inflammatory bowel disease (IBD) and peritonitis. In some embodiments, the inflammatory disease or condition is COPD. In some embodiments, the inflammatory disease or condition is IBD. In some embodiments, the inflammatory disease or condition is peritonitis. According to some embodiments, IBD comprises Crohn's disease. According to some embodiments, IBD comprises colitis. In some embodiments, the inflammatory disease or condition is colitis. In some embodiments, the colitis is ulcerative colitis (UC).

In some embodiments, the method comprises administering an effective amount of at least one of: the compound, the nanoparticle, the composition, or any combination thereof. In some embodiments, an effective amount is the human equivalent of a murine dose of 5 mg/kg body weight. In some embodiments, the human equivalent of the murine dose depends upon the route of administration. In some embodiments, an effective amount is the human equivalent of a murine dose of between 1.25 and 5 mg/kg body weight.

In some embodiments, an effective amount is the human equivalent of a murine dose of between 2.5 and 5 mg/kg body weight. In some embodiments, an effective amount is about 0.4 mg/kg body weight. In some embodiments, an effective amount is about 0.2 mg/kg body weight. In some embodiments, an effective amount is about 0.1 mg/kg body weight Chemical Definitions Compounds are described using standard nomenclature. Unless defined otherwise, all technical and scientific terms used herein have the same meaning as is commonly understood by one of skill in the art to which this invention belongs.

The compounds described herein include enantiomers, mixtures of enantiomers, diastereomers, tautomers, racemates and other isomers, such as rotamers, as if each is specifically described, unless otherwise indicated or otherwise excluded by context. It is to be understood that the compounds provided herein may contain chiral centers. Such chiral centers may be of either the (R—) or (S—) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R—) form is equivalent, for compounds that undergo epimerization in vivo, to administration of the compound in its (S—) form. Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A dash ("-") that is not between two letters or symbols is used to indicate a point of attachment for a substituent. For example, —(C=O)NH2 is attached through the carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example, a pyridyl group substituted by oxo is a pyridine. Combinations of substituents and/or variables are permissible only if such combinations result in stable compounds or useful synthetic intermediates. A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to: alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, oxo, silyl, sulfo-oxo, sulfonyl, sulfone, sulfoxide, sulfonylamino, or thiol. As used herein, the term "substituted" or the term "substituent" are related to one or more (e.g. 2, 3, 4, 5, or 6) substituents, wherein the substituent(s) is as described herein.

As used herein, the term substituent comprises halo, oxo, amino, hydroxy, —$NO_2$, —CN, —OH, —$CONH_2$, —$CONR'_2$, —$CNNR'_2$, —$CSNR'_2$, —CONH—OH, —CONH—$NH_2$, —NHCOR, —NHCSR, —NHCNR, —NC(=O)OR, —NC(=O)NR', —NC(=S)OR', —NC(=S)NR', —$SO_2R'$, —SOR', —SR', —$SO_2OR'$, —$SO_2N(R')_2$, —$NHNR'_2$, —NNR', $C_1$-$C_6$ haloalkyl, optionally substituted $C_1$-$C_6$ alkyl, —$NH_2$, —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), $C_1$-$C_6$ alkyl-$NR'_2$, $C_1$-$C_6$ alkyl-SR', —CONH($C_1$-$C_6$ alkyl), —CON($C_1$-$C_6$ alkyl)$_2$, —$CO_2H$, —$CO_2R'$, —OCOR, —OCOR', —OC(=O)OR', —OC(=O)NR', —OC(=S)OR', —OC(=S)NR', OR', —NR'R', or a combination thereof; wherein each R' independently represents hydrogen, or is selected from the group comprising optionally substituted $C_1$-$C_{10}$ alkyl, optionally substituted $C_1$-$C_{10}$ aminoalkyl, optionally substituted $C_1$-$C_{10}$ hydroxyalkyl, optionally substituted $C_3$-$C_{10}$ cycloalkyl, optionally substituted $C_3$-$C_{10}$ heterocyclyl, optionally substituted heteroaryl, optionally substituted aryl, amino, hydroxy, halo, oxo, cyano, optionally substituted $C_1$-$C_{10}$ alkyl, or any combination thereof as allowed by valency.

As used herein, the term "alkyl" describes an aliphatic hydrocarbon including straight chain and branched chain groups. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e. rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e. rings which share adjacent pairs of carbon atoms) groups having a completely conjugated pi-electron system. The aryl group may be substituted or unsubstituted, as indicated herein.

The term "alkoxy" describes both an O-alkyl and an —O-cycloalkyl group, as defined herein. The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, nitro, amino, hydroxyl, thiol, thioalkoxy, carboxy, amide, aryl and aryloxy, depending on the substituted group and its position in the molecule. Additional substituents are also contemplated.

The term "halide", "halogen" or "halo" describes fluorine, chlorine, bromine or iodine. The term "haloalkyl" describes an alkyl group as defined herein, further substituted by one or more halide(s). The term "haloalkoxy" describes an alkoxy group as defined herein, further substituted by one or more halide(s). The term "hydroxyl" or "hydroxy" describes a —OH group. The term "mercapto" or "thiol" describes a —SH group. The term "thioalkoxy" describes both an —S-alkyl group, and a —S-cycloalkyl group, as defined herein. The term "thioaryloxy" describes both an —S-aryl and a —S-heteroaryl group, as defined herein. The term "amino" describes a —NR'R" group, or a salt thereof, with R' and R" as described herein.

The term "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyran, morpholino and the like.

The term "carboxy" describes a —C(O)OR' group, or a carboxylate salt thereof, where R' is hydrogen, alkyl, cycloalkyl, alkenyl, aryl, heteroaryl(bonded through a ring carbon) or heterocyclyl(bonded through a ring carbon) as defined herein or "carboxylate"

The term "carbonyl" describes a —C(O)R' group, where R' is as defined hereinabove. The above-terms also encompass thio-derivatives thereof (thiocarboxy and thiocarbonyl).

The term "thiocarbonyl" describes a —C(S)R' group, where R' is as defined hereinabove. A "thiocarboxy" group describes a —C(S)OR' group, where R' is as defined herein. A "sulfinyl" group describes an —S(O)R' group, where R' is as defined herein. A "sulfonyl" or "sulfonate" group describes an —S(O)2R' group, where R' is as defined herein.

A "carbamyl" or "carbamate" group describes an —OC(O)NR'R" group, where R' is as defined herein and R" is as defined for R'. A "nitro" group refers to a —NO2 group. The term "amide" as used herein encompasses C-amide and N-amide. The term "C-amide" describes a —C(O)NR'R" end group or a —C(O)NR'-linking group, as these phrases are defined hereinabove, where R' and R" are as defined herein. The term "N-amide" describes a —NR"C(O)R'end group or a —NR'C(O)— linking group, as these phrases are defined hereinabove, where R' and R" are as defined herein.

A "cyano" or "nitrile" group refers to a —CN group. The term "azo" or "diazo" describes an —N=NR' end group or an —N=N— linking group, as these phrases are defined hereinabove, with R' as defined hereinabove. The term "guanidine" describes a —R'NC(N)NR"R'" end group or a —R'NC(N) NR"— linking group, as these phrases are defined hereinabove, where R', R" and R'" are as defined herein. As used herein, the term "azide" refers to a —N3 group. The term "sulfonamide" refers to a —S(O)$_2$NR'R" group, with R' and R" as defined herein.

The term "phosphonyl" or "phosphonate" describes an —OP(O)—(OR')2 group, with R' as defined hereinabove. The term "phosphinyl" describes a —PR'R" group, with R' and R" as defined hereinabove. The term "alkylaryl" describes an alkyl, as defined herein, which substituted by an aryl, as described herein. An exemplary alkylaryl is benzyl.

The term "heteroaryl" describes a monocyclic or fused ring (i.e. rings which share an adjacent pair of atoms) group having in the ring(s) one or more atoms, such as, for example, nitrogen, oxygen and sulfur and, in addition, having a completely conjugated pi-electron system. As used herein, the term "heteroaryl" refers to an aromatic ring in which at least one atom forming the aromatic ring is a heteroatom. Heteroaryl rings can be foamed by three, four, five, six, seven, eight, nine and more than nine atoms. Heteroaryl groups can be optionally substituted. Examples of heteroaryl groups include, but are not limited to, aromatic C3-8 heterocyclic groups containing one oxygen or sulfur atom, or two oxygen atoms, or two sulfur atoms or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl is selected from among oxazolyl, isoxazolyl, oxadiazolyl, thiazolyl, isothiazolyl, pyridinyl, pyridazinyl, pyrimidinal, pyrazinyl, indolyl, benzimidazolyl, quinolinyl, isoquinolinyl, quinazolinyl or quinoxalinyl.

In some embodiments, a heteroaryl group is selected from among pyrrolyl, furanyl (furyl), thiophenyl (thienyl), imidazolyl, pyrazolyl, 1,2,3-triazolyl, 1,2,4-triazolyl, 1,3-oxazolyl (oxazolyl), 1,2-oxazolyl (isoxazolyl), oxadiazolyl, 1,3-thiazolyl (thiazolyl), 1,2-thiazolyl (isothiazolyl), tetrazolyl, pyridinyl (pyridyl)pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, benzodioxolyl, acridinyl, quinolinyl, isoquinolinyl, quinazolinyl, quinoxalinyl, phthalazinyl, thienothiophenyl, 1,8-naphthyridinyl, other naphthyridinyls, pteridinyl or phenothiazinyl. Where the heteroaryl group includes more than one ring, each additional ring is the saturated form (perhydro form) or the partially unsaturated form (e.g., the dihydro form or tetrahydro form) or the maximally unsaturated (nonaromatic) form. The term heteroaryl thus includes bicyclic radicals in which the two rings are aromatic and bicyclic radicals in which only one ring is aromatic. Such examples of heteroaryl are include 3H-indolinyl, 2(1H)-quinolinonyl, 4-oxo-1,4-dihydroquinolinyl, 2H-1-oxoisoquinolyl, 1,2-dihydroquinolinyl, (2H)quinolinyl N-oxide, 3,4-dihydroquinolinyl, 1,2-dihydroisoquinolinyl, 3,4-dihydro-isoquinolinyl, chromonyl, 3,4-dihydroiso-quinoxalinyl, 4-(3H)quinazolinonyl, 4H-chromenyl, 4-chromanonyl, oxindolyl, 1,2,3,4-tetrahydroisoquinolinyl, 1,2,3,4-tetrahydro-quinolinyl, 1H-2,3-dihydroisoindolyl, 2,3-dihydrobenzo[f]isoindolyl, 1,2,3,4-tetrahydrobenzo-[g]isoquinolinyl, 1,2,3,4-tetrahydro-benzo[g]isoquinolinyl, chromanyl, isochromanonyl, 2,3-dihydrochromonyl, 1,4-benzo-dioxanyl, 1,2,3,4-tetrahydro-quinoxalinyl, 5,6-dihydro-quinolyl, 5,6-dihydroisoquinolyl, 5,6-dihydroquinoxalinyl, 5,6-dihydroquinazolinyl, 4,5-dihydro-1H-benzimidazolyl, 4,5-dihydro-benzoxazolyl, 1,4-naphthoquinolyl, 5,6,7,8-tetrahydro-quinolinyl, 5,6,7,8-tetrahydro-isoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydro-benzoxazolyl, 1H-4-oxa-1,5-diazanaphthalen-2-onyl, 1,3-dihydroimidizolo-[4,5]-pyridin-2-onyl, 2,3-dihydro-1,4-dinaphtho-quinonyl, 2,3-dihydro-1H-pyrrol[3,4-b]quinolinyl, 1,2,3,4-tetrahydrobenzo[b]-[1,7]naphthyridinyl, 1,2,3,4-tetra-hydrobenz[b][1,6]-naphthyridinyl, 1,2,3,4-tetrahydro-9H-pyrido[3,4-b]indolyl, 1,2,3,4-tetrahydro-9H-pyrido[4,3-b]indolyl, 2,3-dihydro-1H-pyrrolo-[3,4-b]indolyl, 1H-2,3,4,5-tetrahydro-azepino[3,4-b]indolyl, 1H-2,3,4,5-tetrahydroazepino-[4,3-b]indolyl, 1H-2,3,4,5-tetrahydro-azepino[4,5-b]indolyl, 5,6,7,8-tetrahydro[1,7]napthyridinyl, 1,2,3,4-tetrahydro-[2,7]-naphthyridyl, 2,3-dihydro[1,4]dioxino[2,3-b]pyridyl, 2,3-dihydro[1,4]-dioxino[2,3-b]pryidyl, 3,4-dihydro-2H-1-oxa[4,6]diazanaphthalenyl, 4,5,6,7-tetrahydro-3H-imidazo-[4,5-c]pyridyl, 6,7-dihydro[5,8]diazanaphthalenyl, 1,2,3,4-tetrahydro[1,5]-napthyridinyl, 1,2,3,4-tetrahydro[1,6]napthyridinyl, 1,2,3,4-tetrahydro[1,7]napthyridinyl, 1,2,3,4-tetrahydro-[1,8]napthyridinyl or 1,2,3,4-tetrahydro[2,6]napthyridinyl. In some embodiments, heteroaryl groups are optionally substituted. In one embodiment, the one or more substituents are each independently selected from among halo, hydroxy, amino, cyano, nitro, alkylamido, acyl, C1-6-alkyl, C1-6-haloalkyl, C1-6-hydroxyalkyl, C1-6-aminoalkyl, C1-6-alkylamino, alkylsulfenyl, alkylsulfinyl, alkylsulfonyl, sulfamoyl, or trifluoromethyl.

Examples of heteroaryl groups include, but are not limited to, unsubstituted and mono-or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline and quinoxaline. In some embodiments, the substituents are halo, hydroxy, cyano, O—C1-6-alkyl, C1-6-alkyl, hydroxy-C1-6-alkyl and amino-C1-6-alkyl.

As used herein, the terms "halo" and "halide", which are referred to herein interchangeably, describe an atom of a halogen, that is fluorine, chlorine, bromine or iodine, also referred to herein as fluoride, chloride, bromide and iodide.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic salts. Example of such salts include, but are not limited to, those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, mesylic, esylic, besylic, sulfanilic, 2-acetoxybenzoic, fumaric, toluenesulfonic, methanesulfone, ethane disulfonic, oxalic, isethionic, HOOC—(CH2)1-4—COOH, and the like, or using a different acid that produced the same counterion. Lists of additional suitable salts may be found, e.g., in Remington's Pharmaceutical Sciences, 17th ed., Mack Publishing Company, Easton, PA., p. 1418 (1985).

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

General

As used herein the term "about" refers to +10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Strategies for Protein Purification and Characterization—A Laboratory Course Manual" CSHL Press (1996); all of which are incorporated by reference. Other general references are provided throughout this document.

Methods

Degranulation assay (human neutrophils): 5 mL human blood was drawn into an EDTA containing tube. Neutrophils were purified on a FICCOL gradient, and 100,000 neutrophils were used per sample. Phorbol myristate acetate (PMA, 50 nM) was added for neutrophil stimulation. Samples were cultured either with PMA alone, or with the compounds (50 µM) for 30 minutes at 37° C. and then evaluated in FACS after staining with anti-CD66b Ab to detect neutrophil populations and with anti-CD11b Ab to detect degranulation. Nexinhib20 (50 µM) was used as a positive control. DMSO was used as a negative control. Mean fluorescence intensity (MFI) of CD11b was normalized to the levels after PMA stimulation.

Degranulation assay (mouse neutrophils): 1 mL mouse blood was drawn from the mouse heart into an EDTA containing tube. Neutrophils were purified on a FICCOL gradient, and 100,000 neutrophils were used per sample. Samples were cultured either with PMA alone (50 nM), or with the compounds (50 M) for 30 minutes at 37° C., and then evaluated in FACS after staining with anti-Ly6G Ab to detect neutrophil populations and anti-CD11b Ab to detect degranulation. Nexinhib20 (50 µM) was used as a positive control. DMSO was used as a negative control. MFI of CD11b was normalized to the levels after PMA stimulation.

ROS assay (human neutrophils): 5 mL human blood was drawn into an EDTA containing tube. Red blood cells (RBCs) were lysed and white blood cells (WBCs) were isolated by spin down and washes. An average of 5,000 WBCs/well were stimulated with 100 nM PMA and cultured in the presence of the compounds at a concentration of 5 µM for 30 minutes at 37° C. Luminol was added to the wells and activity was read with a luminescence plate reader (cycle #16, 22.5 minutes). Nexinhib20 (5 µM) and DPI (1 µM) were used as positive controls. HBSS buffer or buffer with DMSO added were used as negative controls. Luminescence signal was normalized to control (DMSO alone).

ROS assay (murine neutrophils): 0.5 mL mouse blood was drawn into an EDTA containing tube. RBCs were lysed, and WBCs were isolated by spin down and washes. An average of 2,000 WBCs/well were stimulated with 100 nM PMA and cultured in the presence of the compounds at a concentration of 5 µM for 30 minutes at 37° C. Luminol was added to the wells and activity was read with a luminescence plate reader (cycle #16, 22.5 minutes). Nexinhib20 (5 µM) and DPI (1 µM) were used as positive controls. HBSS buffer or buffer with DMSO added were used as negative controls. Luminescence signal was normalized to control (DMSO alone).

NETosis assay: The assay was carried out as previously described (Gupta et al., "A High-Throughput Real-Time Imaging Technique To Quantify NETosis and Distinguish Mechanisms of Cell Death in Human Neutrophils.", J Immunol. 2018; 200:869-879, herein incorporated by reference in its entirety). Briefly, human neutrophils (2×106 cells/mL) were incubated for 5 minutes in the dark at RT with the NUCLEAR-ID Red DNA dye to stain nuclei (Enzo Life Sciences, Inc.). Cells were washed twice and resuspended in 1 mL of RPMI media. NUCLEAR-ID Red stained-neutrophils were plated (20,000 neutrophils per 100 µL per well) in a 96-well flat microplate. Stimulation of neutrophils NETosis was performed with PMA alone (50 nM), or with PMA in the presence of T1 compound (10 µM) or T3 compound (10 µuM). Unstimulated neutrophils served as a negative control. Neutrophils stimulated with PMA in the presence of Trifluoperazine (Stelazine, 100 ng/ml) were used as positive control. A final concentration of 0.1 µM of the membrane impermeable dsDNA fluorescent Sytox® Green nucleic acid stain (Life Technologies, Inc.) was added to the plated cells concomitantly with the stimuli. Neutrophils were imaged within 10 minutes of plating using phase contrast, red (800 ms exposure) and green (400 ms exposure) channels in the IncuCyte ZOOM™ platform (Essen BioScience, Inc.), located within a cell incubator at 37° C. with 5% CO2. Four image sets from distinct regions per well using a 20x dry objective lens were taken every 20-30 minutes, for 8 hr. For red channel, filters were applied to exclude objects below radius of 10 μm, fluorescence threshold of 0.5 red corrected units, and area of 15 μm². The filters applied the green channel excluded objects below the radius of 10 μm, fluorescence threshold of 1.00 green corrected units, and area of 100 μm². The green object count divided by the red object count represents the percentage of cells going through NETosis of total neutrophils. Liposome preparation: 2.5% DSPE-PEG3400-Maleimide liposomes were prepared in 250 mM ammonium sulfate. Liposomes were prepared at a molar ration of 56.5:41: 2.5:0.09 of HSPC: Cholesterol: DSPE-PEG-Mal: DilC18 (5)-DS. Lipids were prepared by a standard ethanol injection protocol and following extrusion were found to have an average size of 118.9 nm and an average polydispersity index (DPI) of 0.085.

LQI monomer conjugation: Liposomes were buffer exchanged into PBS and empty, unconjugated liposomes were retained as control. The LQI peptide, LQIQSWSSSP (SEQ ID NO: 9), was extended to include a C-terminal cysteine (LQIQSWSSSPC, SEQ ID NO: 14) and was reacted with the maleimide on the surface of the liposome to covalently link the peptide to the liposome surface. Following conjugation free maleimides were quenched with L-cysteine and then the linked liposomes were washed and filtered.

Active drug loading to liposomes: 50 mg of drug were dissolved in 7.5% dextrose and the pH was adjusted to ~6 with MES buffer. Control "Empty" liposomes were still loaded with 7.5% dextrose with 10 μl of MES buffer added. For loading, liposomes were mixed with dissolved drug at 60° C. for 30 minutes and then cooled on ice for 15 minutes. Loaded liposomes had a size ranging from ~135-145 nm. Free drug that was not loaded was separated from the liposome using size exclusion with PD-10 columns. HPLC was used to measure drug and cholesterol content in the final liposomes.

The liposomes were also analyzed over 4 months of storage in order to monitor drug retention within the liposome. A small amount of leakage was observed, but even over 4 months the relative amount of drug to lipid was not greatly changed. The data on the liposome composition is provided in Table 1.

TABLE 1

Liposome composition loaded with T3.

|  | T3 conc. (ug/ml) | T3/Lipid Ratio (mg/mg) | Particle Size (diameter, nm) | PDI |
| --- | --- | --- | --- | --- |
| Time 0 | 960.462 | 0.08 | 133.3 | 0.149 |
| 2 Months | 865.52 | 0.076 | 137.3 | 0.152 |
| 4 Months | 838.06 | 0.0697 | 135.1 | 0.144 |

Example 1

The In-Vitro Effect of T1, T3 and T4 Compounds on Neutrophil Activation

Initially, the in-vitro effect of the compounds, T1, T3 and T4, on neutrophil activation were examined. The chemical structures of the compounds are presented in FIG. 1.

Figure 2A:
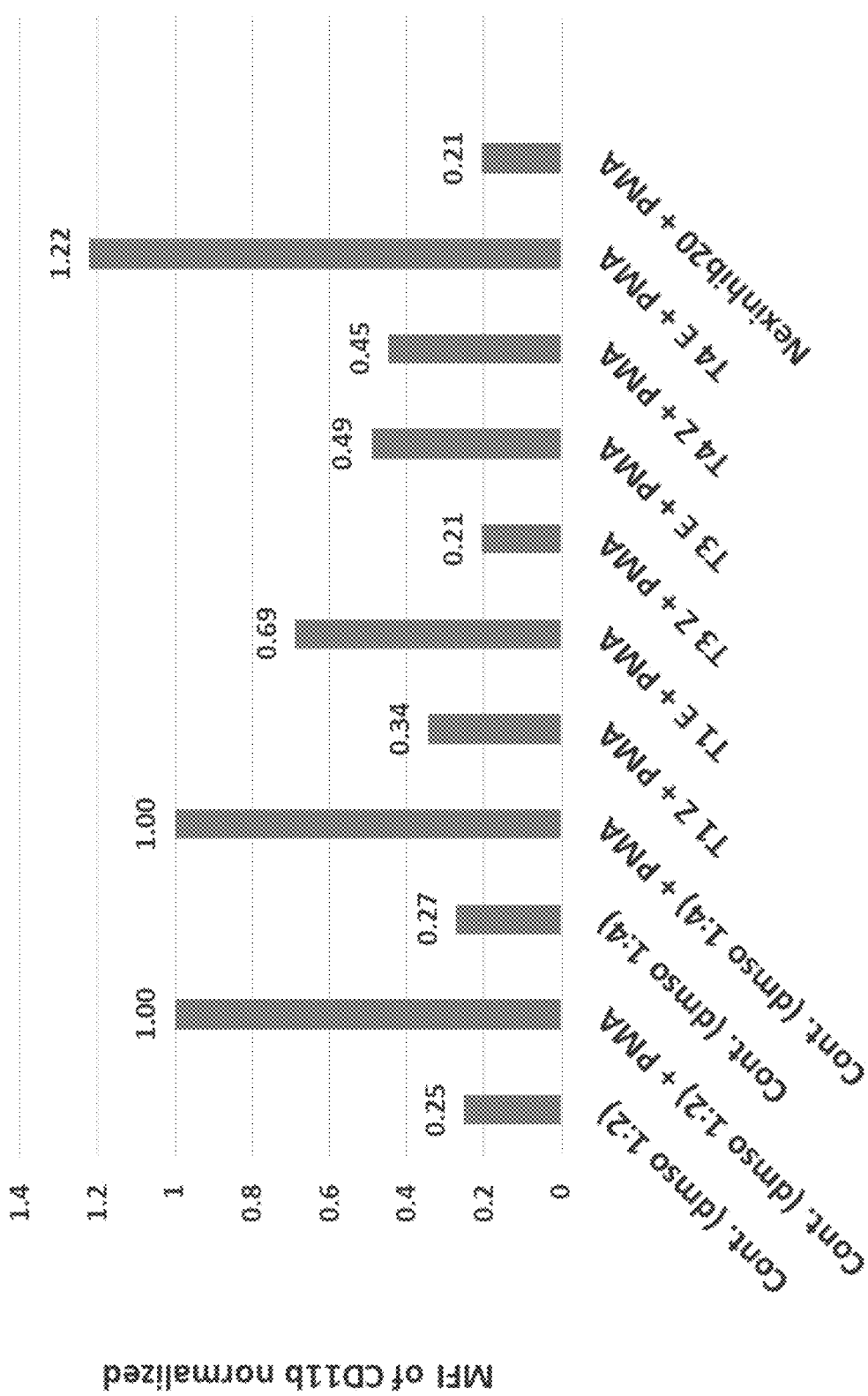
FIGS. 2A-B: Bar graphs showing the effect of the compounds T1, T3 and T4, in both E and Z isomers, on the degranulation process of stimulated (2A) human and (2B) murine neutrophils. Mean fluorescence intensity (MFI) of CD11b, a marker for degranulation, is provided. MFI level are normalized to the fluorescence after PMA stimulation of the controls.
Figure 2B:
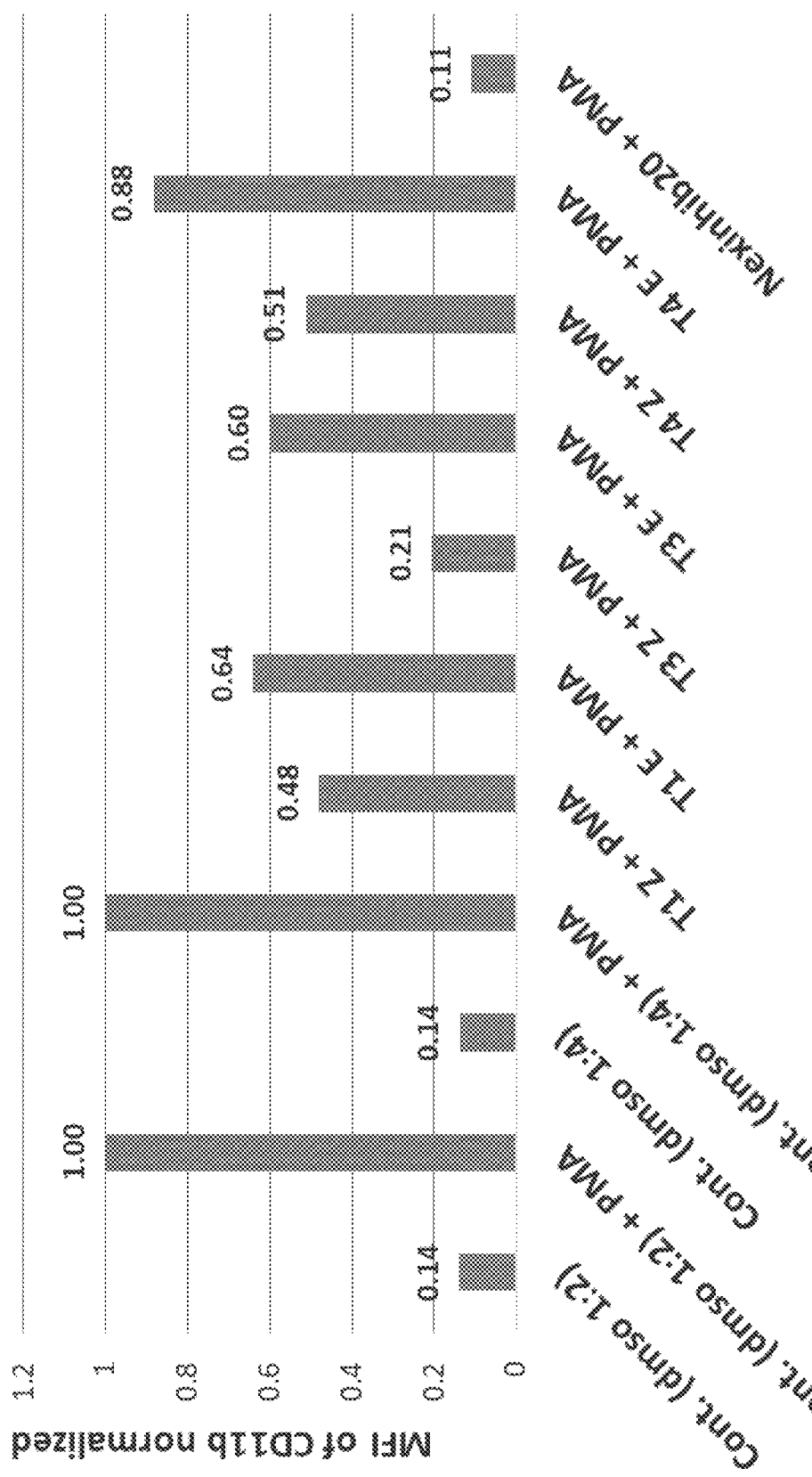

First, neutrophils were purified from human blood and were either left unstimulated or were stimulated with phorbol myristate acetate (PMA). The three compounds were added (50 μM) both to unstimulated and PMA stimulated cells, and DMSO was used as a negative control. Two isomers of each compound were examined: the Z and E isomers. Following PMA stimulation, neutrophils are known to degranulate, and increased surface expression of CD11b is a well-known marker of this phenomenon. Treatment of the neutrophils with T1 (E and Z isomers), T3 (E and Z isomers) and T4 (Z isomer) greatly reduced PMA-induced degranulation (FIG. 2A). Indeed, the T1 Z isomer and the T3 Z isomer were able to return CD11b levels back to that of unstimulated neutrophils. Notably, the Z isomers of all three molecules were superior to the E isomers. Nexinhib-20 is known to inhibit degranulation and the Z isomers of T3 was as good as Nexinhib-20. Similar results were obtained when murine neutrophils were tested (FIG. 2B).

Figure 3A:
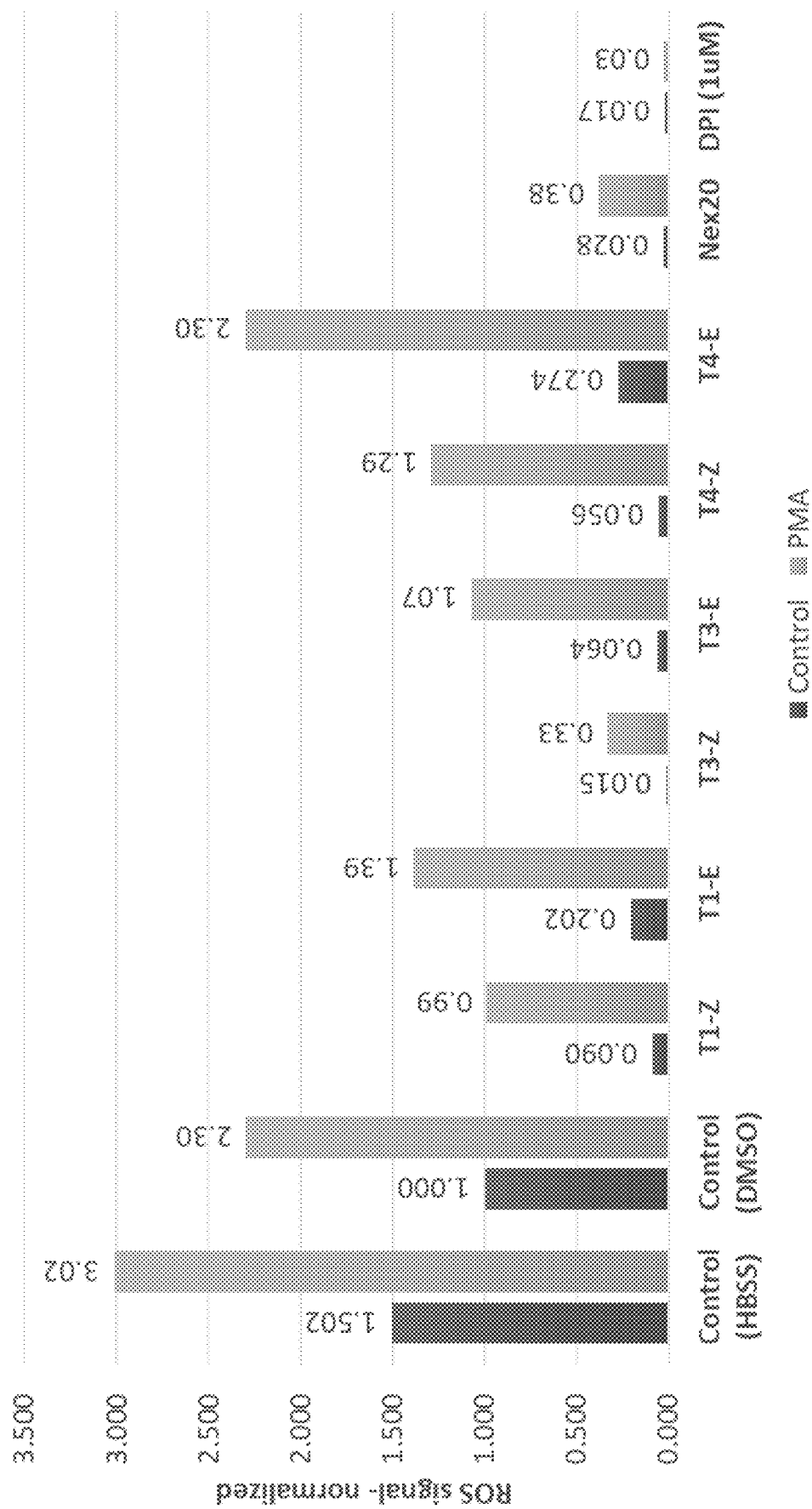
FIGS. 3A-B: Bar graphs showing the effect of the compounds T1, T3 and T4, in both E and Z isomers, on reactive oxygen species (ROS) production by stimulated (3A) human and (3B) murine neutrophils.
Figure 3B:
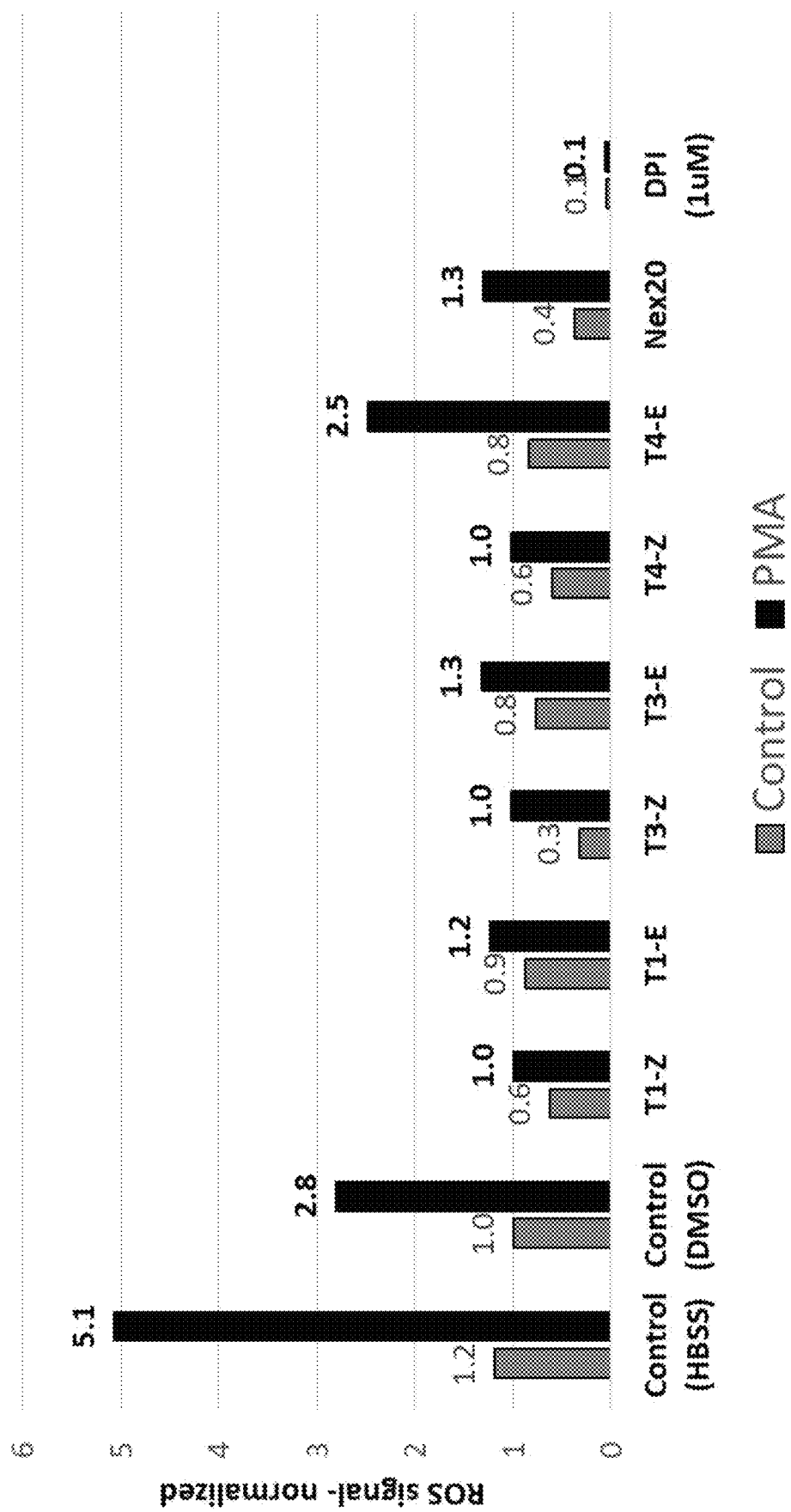

Neutrophil stimulation is also known to increase reactive oxygen species (ROS) production. The in-vitro effect of the compounds on PMA-induced ROS production by neutrophils was examined next. As expected, addition of PMA increased ROS production to 2-3 times basal levels in human neutrophils (FIG. 3A). All of the tested molecules, including both the E and Z isomers, greatly reduced ROS production in untreated neutrophils. This demonstrates that the molecules inhibit even basal ROS production. T1 (E and Z isomers), T3 (E and Z isomers) and T4 (Z isomer) also greatly decreased the PMA-induced ROS increase; with ROS levels reducing to at least those observed in the unstimulated neutrophils (FIG. 3A). The T3 Z isomer showed the best ROS inhibition, with levels after PMA stimulation that were greatly lower than even the control levels without PMA. This inhibition was comparable to the inhibition produced by Nexinhib20 and T3Z was nearly as strong as the inhibitor Diphenylenciodonium (DPI) which is known to nearly completely abolish ROS production by inhibiting NAD(P)H (FIG. 3A). Similar results were observed in murine PMA-stimulated neutrophils (FIG. 3B).

Figure 4:
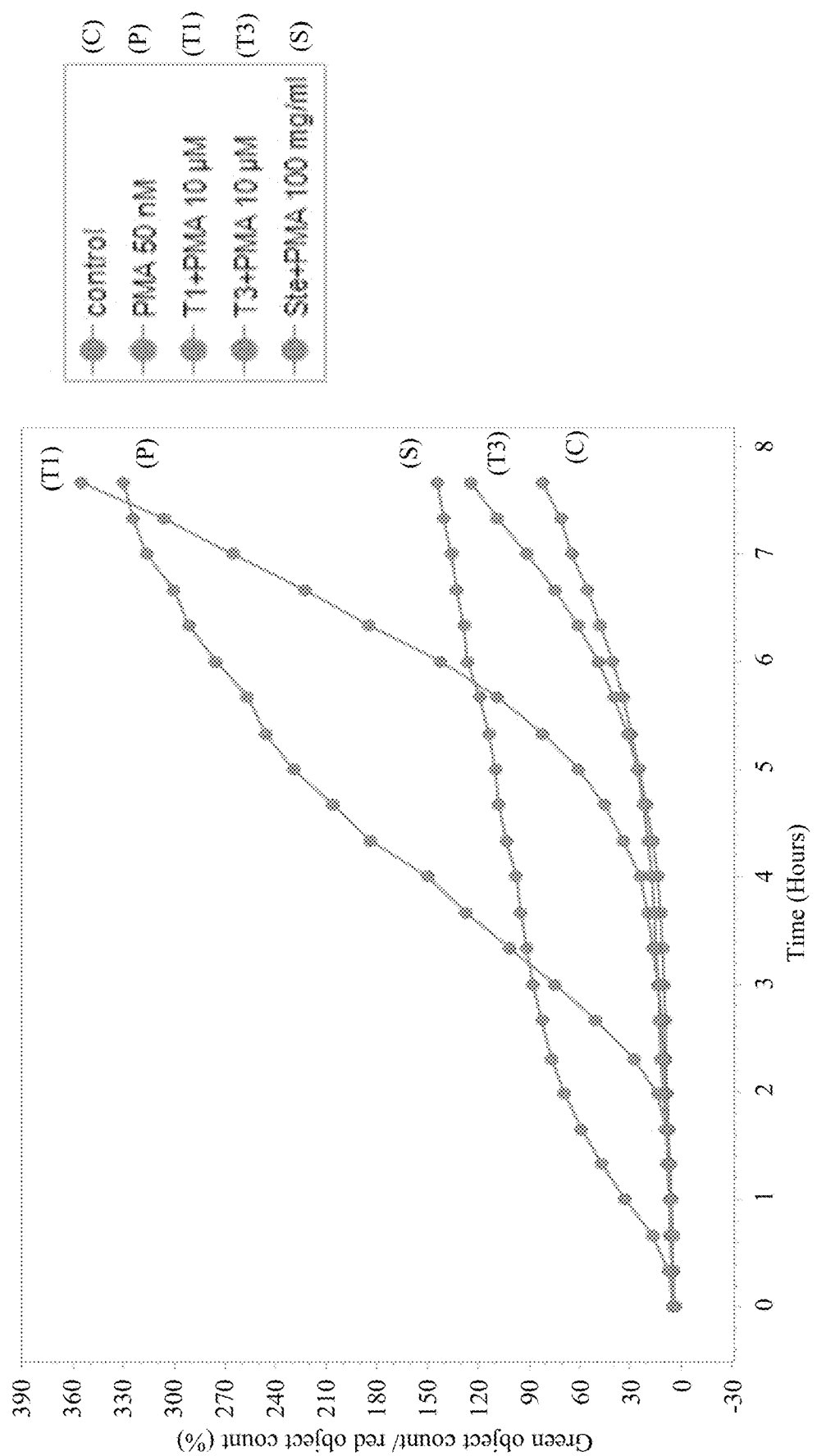
FIG. 4: Line graph showing the effect of T1 and T3 compounds on neutrophil NETosis induced by PMA. Stelazine® (Ste), previously identified neutrophil ROS inhibitor, is used as a positive control.

Besides degranulation, neutrophils can kill pathogens extracellularly by releasing neutrophil extracellular traps (NETs), a process known as NETosis. Examination of NETosis induced by PMA was monitored by an Incucyte live-cell analysis system (FIG. 4). PMA treatment produced a steady increase in NETosis positive events starting at 2 hours after treatment. Trifluoperazine (sold as Stelazine®), which is a known inhibitor of NETosis, produced a steady reduction after PMA treatment. In contrast, both T1 and T3 initially inhibited an increase in NETosis completely. An increase was only observed after 4 hours when T1 was used and after 5 hours when T3 was used. T3 was very similar to control showing only a small increase in NETosis events only at very late time points (FIG. 4).

Example 2

The In-Vivo Effect of T3 on Inflammation

The next objective was to examine the in-vivo effect of the T3 compound in inflammatory disease and cancer. The T3 compound (Z isomer) was prepared in three compositions: (i) T3 as a free molecule (free drug), (ii) T3 within a liposome; and (iii) T3 within a liposome targeted to neutrophils by surface peptides (TENN). Specifically, the liposome was bound to a peptide consisting of the sequence LQIQSWSSSP (SEQ ID NO: 9), designated as LQI-peptide. This peptide is known in the art to specifically bind neutrophils, as described in: "Völs et al., "Targeted nanoparticles modify neutrophil function in vivo." Front Immunol. 2022; Oct 5; 13:1003871", herein incorporated by reference in its entirety.

Figure 5:
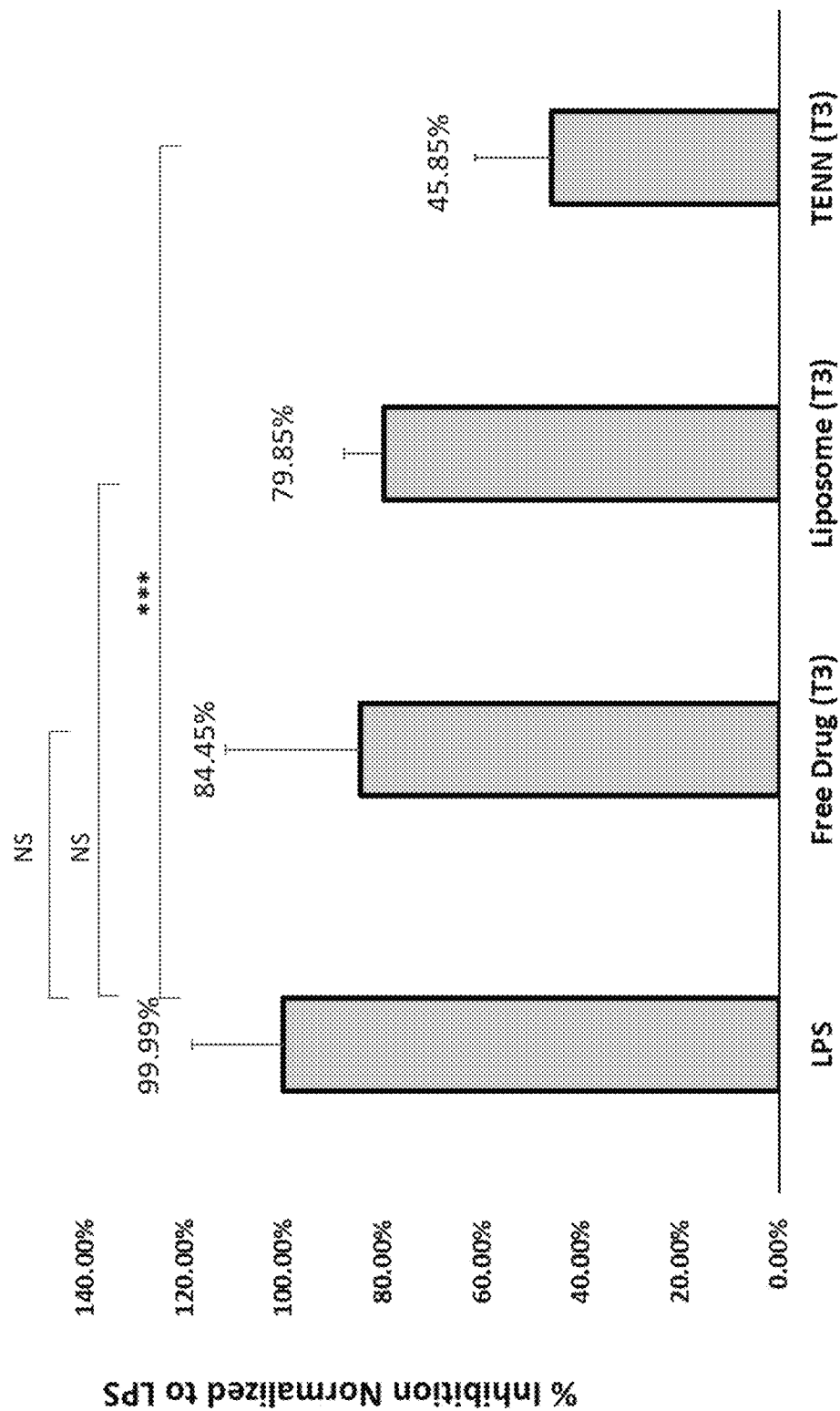
FIG. 5: Bar graph showing the in-vivo effect of T3 on LPS-induced inflammation. Free compound T3, T3 incorporated within a liposome, and T3 incorporated within a targeted liposome (TENN-T3) were tested for their effect on surface neutrophil CD11b levels after LPS stimulation. MFI of CD11b staining was normalized to the neutrophil CD11b levels after LPS stimulation. *** p<0.001.

The in-vivo effect of the three compositions of T3 was examined in a mouse model of inflammation. Balb/C mice were intraperitoneal injected with 1 mg/kg of LPS to induce inflammation and neutrophil toxicity. After 1 hour, T3—free molecule, T3 within a liposome, and T3 within a targeted liposome (TENN-T3) were IV administered at a final concentration of 3 mg/kg body weight. After 3 hours 0.5 mL of blood was drawn from each mouse and degranulation of peripheral blood neutrophils was evaluated by flow cytometry analysis of surface CD11b levels (neutrophils were identified by Ly6G staining). Neutrophils activated by LPS become toxic and degranulate; T3 in its free form induced a moderate but not statistically significant reduction in degranulation (FIG. 5). T3 within a liposome, produced only a slightly greater decrease which was also not statistically significant. However, the targeted liposome comprising T3 (TENN-T3) produced a greater than 50% reduction in granulation which was more than three times the reduction produced by the free molecule T3. Overall, it is clear that T3 inhibits neutrophil activation in vivo and that targeting greatly enhances the effect.

Figure 6A:
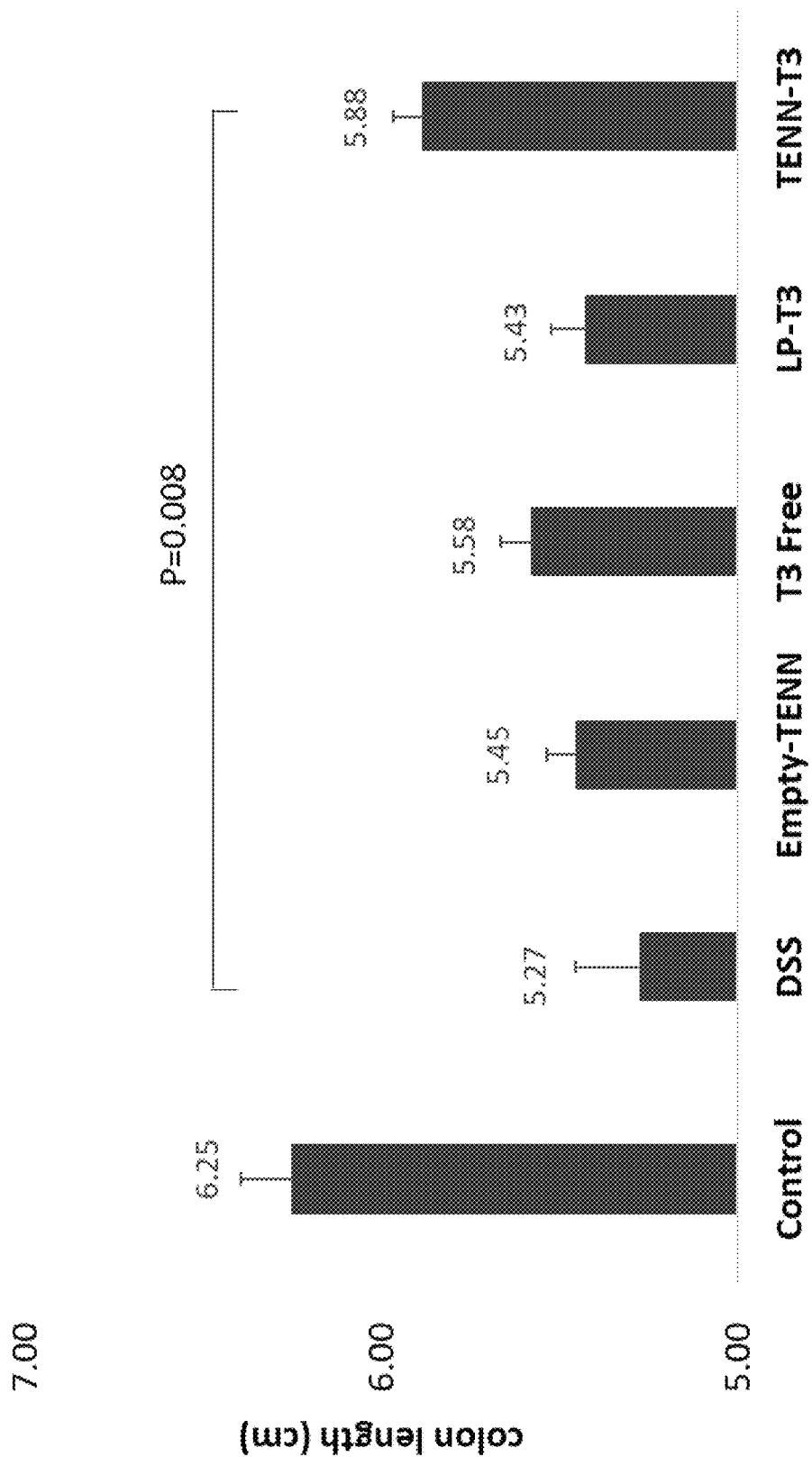
FIGS. 6A-C: (6A) Bar graph of colon length in the DSS colitis model mice treated with T3 in its various formulations and with empty targeted nanoparticles (TENNs). (6B) (Above) Micrograph of luminescence representing ROS levels in colons from healthy control mice, and DSS treated colitis mice with and without TENN-T3 administration. White arrows point to positive luminescence signal. (Below) Bar graph quantification of the luminescence. The luminescence in DSS-treated mice is increased as compared to control (no DSS treatment) while TENN-T3 lowers ROS levels. (6C) Bar graph of colon length in DSS colitis model mice treated with various concentrations of TENN-T3. Cyclosporine A (Cyclo) was used a positive control.
Figure 6B:
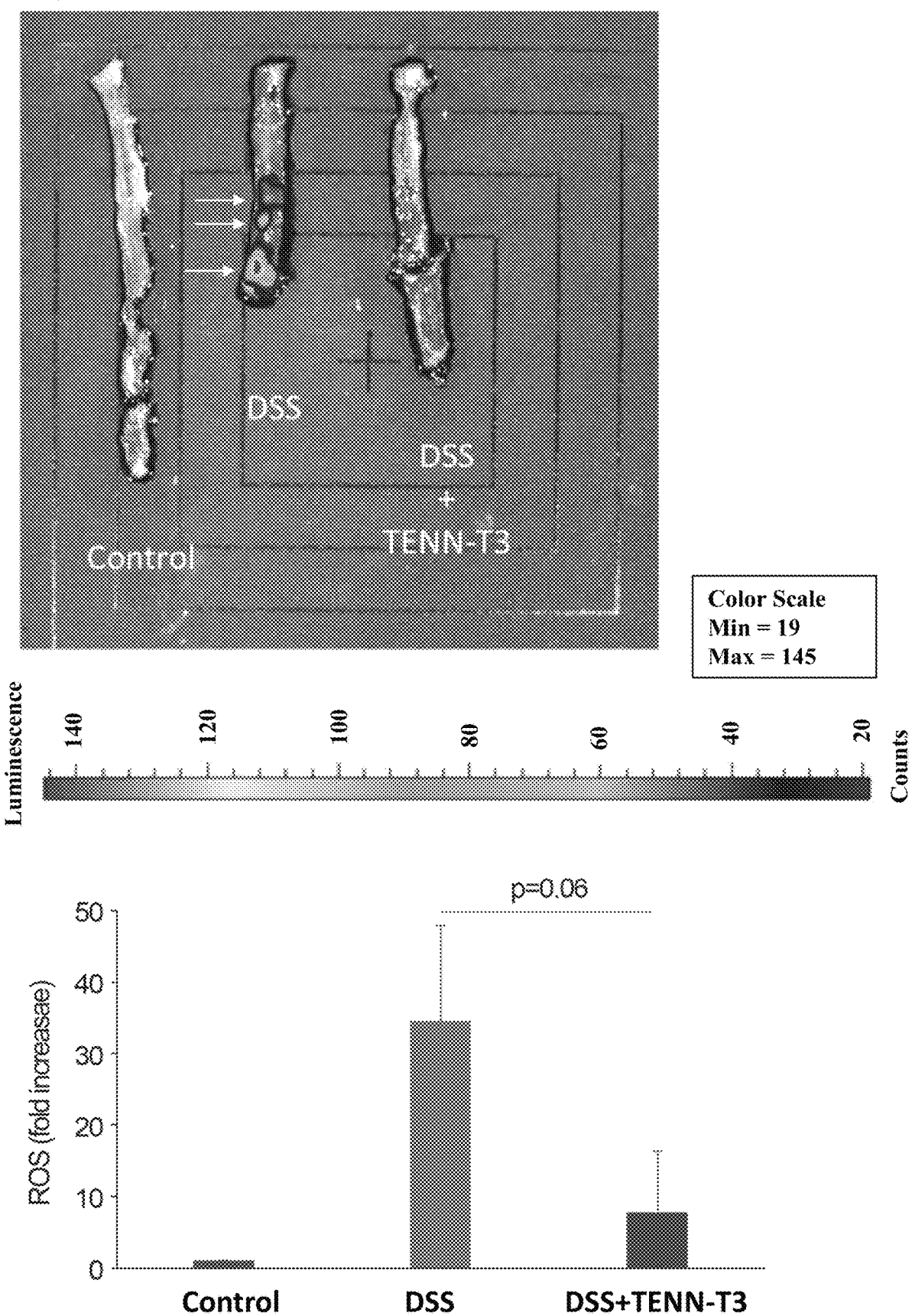

Next, the ability of T3 administration, to treat colitis, a disease caused at least in part by neutrophil cytotoxicity, was tested in a mouse model. Colitis was induced in C57BL/6 mice by administration of 3% dextran sulfate sodium (DSS) for 5 consecutive days in drinking water. 2.5 mg/kg of T3, in its three formulations, was administered on days 5, 7 and 9. Colitis induction by DSS caused a pronounced shortening of the mouse colon. Free T3 or T3 loaded into non-targeted liposomes were comparable to a negative control administration of empty targeted liposomes (FIG. 6A). However, T3 loaded into targeted liposomes (TENN-T3), produced a marked lengthening of the colon with an average improvement of ~62% as compared to the no treatment (DSS only) group. Moreover, measurement of ROS levels within the colons (from mice sacrificed on day 11), by luminol-based bioluminescence imaging, showed significantly reduced levels of ROS in the colons of the TENN-T3-treated mice as compared to the DSS alone group (FIG. 6B).

Figure 6C:
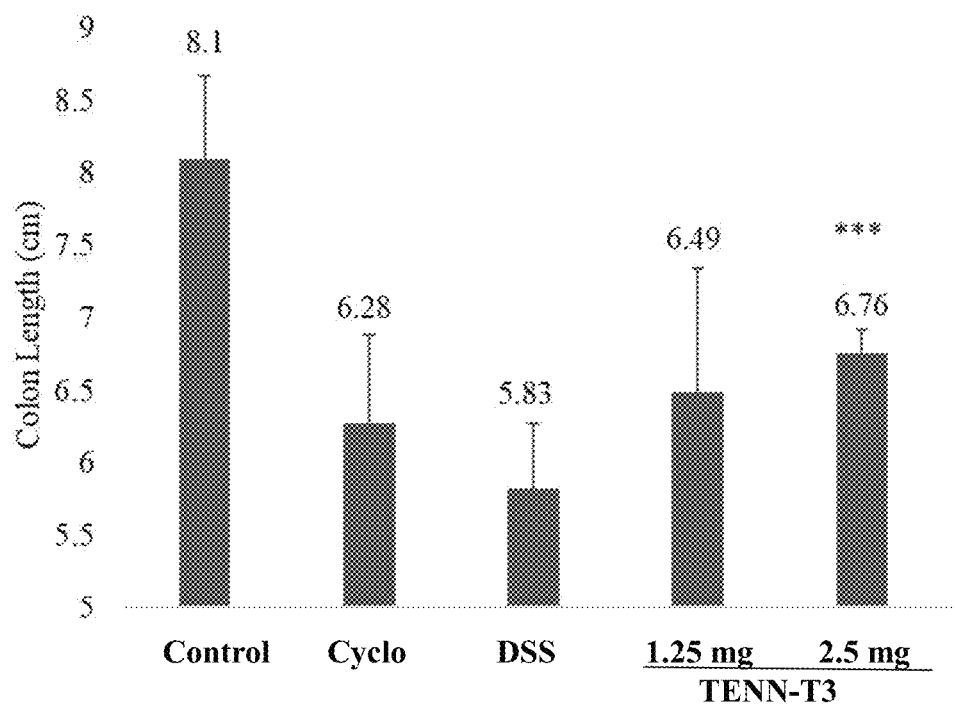

Lower doses of TENN-T3 were also tested. The targeted liposomes were administered at days 5 and 7 and mice were sacrificed on day 10 and colon length was measured. A dose of 1.25 mg/kg body weight was able to improve colon length better than cyclosporine (7.5 mg/kg body weight), a known colitis treatment and considered a positive control for the DSS model (FIG. 6C). A dose of 2.5 mg/kg of TENN-T3, had an even greater, and statistically significant, effect.

Example 3

The In-Vivo Treatment of Cancer with T3

Figure 7:
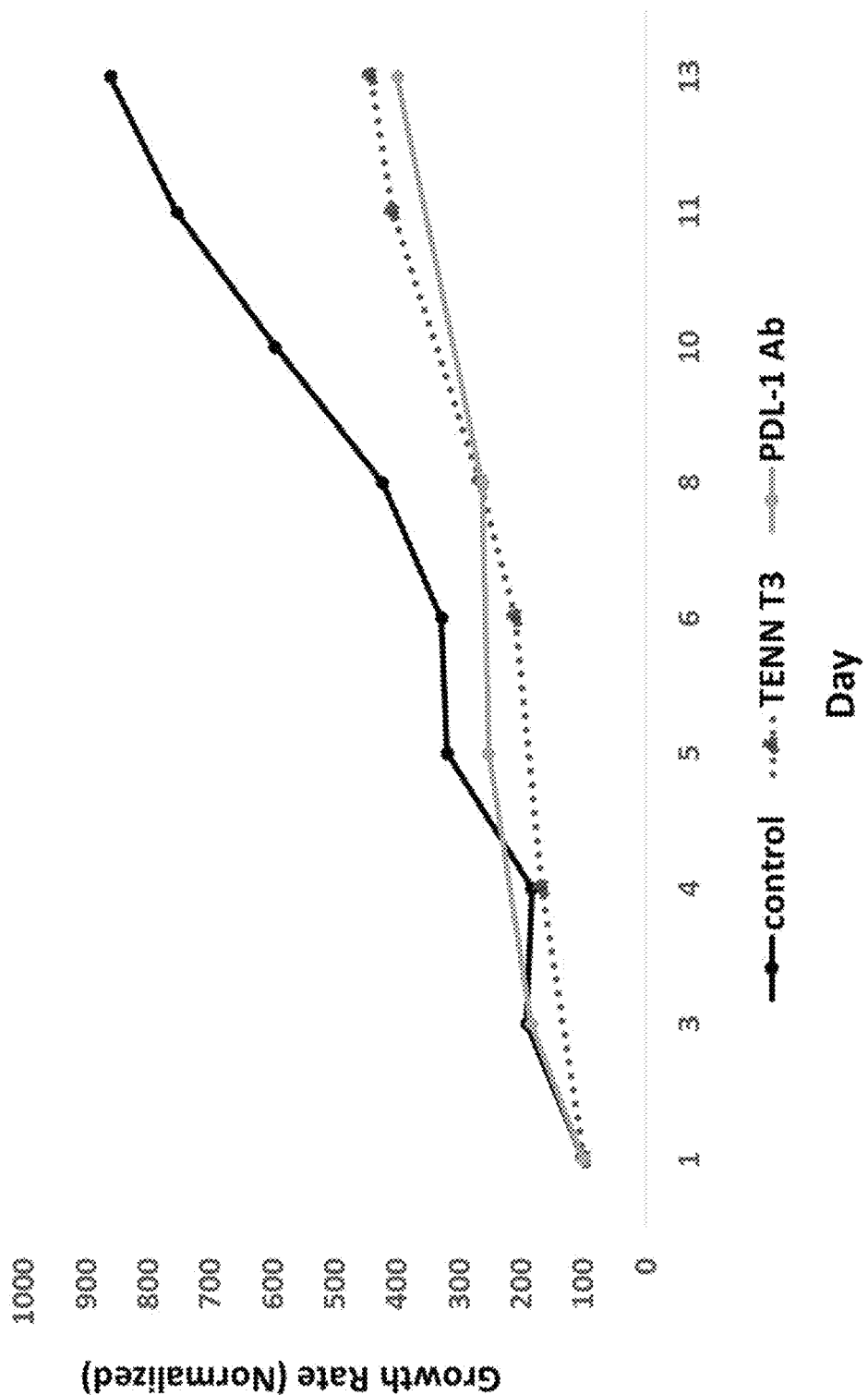
FIG. 7: A line graph of tumor growth in RENCA injected Balb/C mice. Two weeks post injection (day 0), once tumors reached 100 mm³, the mice were treated with TENN-T3 or an anti-PD-L1 antibody as a positive control. Tumor size was measured every other day (N=6 in each group). The tumor size in each mouse was normalized to its original tumor size, on day 0. Tumor growth rate is given as a percentage of the size at day 0. Thus, at day 0 all mice are plotted at a tumor size of 100%.

Neutrophils are known to have various cancer-promoting effects. Therefore, the therapeutic potential of TENN-T3 as a means of inhibiting solid tumor growth was examined. Renca cells are epithelial cells that were isolated from the kidney of a male mouse with renal cortical adenocarcinoma. The Renca syngeneic murine model is therefore a kidney cancer model utilized for studying antitumor drug efficacy. BALB/c mice were administered subcutaneous injections of 1 million Renca cells and tumors were allowed to grow to a size of 100 mm$^3$. Mice were then treated with TENN-T3 (5 mg/kg) twice a week for 2 weeks or with anti-PD-L1 antibody (0.2 mg/kg) every other day. It was surprisingly found that TENN-T3 significantly inhibited tumor cell growth, by about 50% as compared to vehicle treatment alone (FIG. 7). This result was comparable to the one produced by the anti-PD-L1 antibody.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:
1. A compound, including any stereoisomer or a salt thereof, wherein said compound is represented by Formula I:

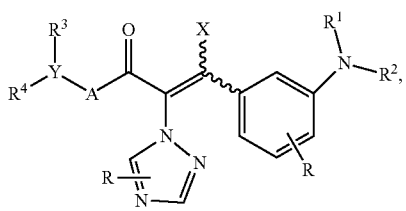

(I)

or by Formula (IIb):

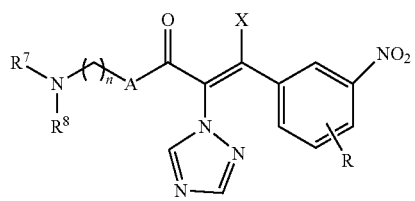

wherein:
A represents any one of a methyl group, isopropyl group, tert-butyl group, a linear or branched $C_1$-$C_{10}$ alkyl group, a linear or branched $C_2$-$C_{10}$ alkyl group substituted or not substituted, a substituted $C_2$-$C_{10}$ alkyl group, optionally substituted $C_3$-$C_{10}$ cycloalkyl group comprising one or more carbocyclic rings, an optionally substituted $C_2$-$C_{10}$ alkyl group comprising one or more heteroatom(s), a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, and a bicyclic aliphatic ring;
Y is absent or is selected from the group consisting of N, NH, $NR^1$, CH, $HCR^1$, $CH_2$, S, SH, and O;
n is an integer between 0 and 5;
X is hydrogen or represents a substituent selected from the group consisting of: a halo group, a methyl group, isopropyl group, $C_2$-$C_{10}$ alkyl group, a substituted $C_2$-$C_{10}$ alkyl group, an alkoxy group, an amino group, and a hydroxy group;
each R independently is absent or represents one or more substituents each independently comprising any one of a methyl group, isopropyl group, $C_2$-$C_{10}$ alkyl group, a substituted $C_2$-$C_{10}$ alkyl group, halo, oxo, —$NO_2$, amino, hydroxy, —CN, —OH, —$CONH_2$, —$CONR'_2$, —$CNNR'_2$, —CSNR'2, —CONH—OH, —CONH—$NH_2$, —NHCOR, —NHCSR, —NHCNR, —NC(=O) OR, —NC(=O)NR', —NC(=S) OR', —NC(=S)NR', —$SO_2R'$, —SOR', —SR', —$SO_2OR'$, —$SO_2N(R')_2$, —$NHNR'_2$, —NNR', $C_1$-$C_6$ haloalkyl, optionally substituted $C_1$-$C_6$ alkyl, —$NH_2$, —NR'R', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), $C_1$-$C_6$ alkyl-$NR'_2$, $C_1$-$C_6$ alkyl-SR', —CONH($C_1$-$C_6$ alkyl), —CON($C_1$-$C_6$ alkyl)$_2$, —$CO_2H$, —$CO_2R'$, —OCOR, —OCOR', —OC(=O)OR', —OC(=O) NR', —OC(=S)OR', —OC(=S)NR', —OR', —NR'R', or a combination thereof; wherein each R' independently represents hydrogen, or is selected from the group consisting of optionally substituted $C_1$-$C_{10}$ alkyl, optionally substituted $C_3$-$C_{10}$ cycloalkyl, optionally substituted $C_3$-$C_{10}$ heterocyclyl, optionally substituted heteroaryl, optionally substituted aryl, amino, hydroxy, halo, oxo, cyano, optionally substituted $C_1$-$C_{10}$ alkyl, or any combination thereof as allowed by valency;
$R^1$ and $R^2$ are each independently selected from the group consisting of hydrogen, $C_1$-$C_{20}$ alkyl group, optionally substituted linear or branched $C_1$-$C_{20}$ aminoalkyl group, optionally substituted linear, branched or cyclic $C_1$-$C_{20}$ alkyl group optionally comprising one or more heteroatom(s), a substituted $C_1$-$C_{20}$ alkyl group, a $C_1$-$C_{20}$ haloalkyl group, a substituted $C_1$-$C_{20}$ haloalkyl group, an aliphatic linear or branched $C_3$-$C_{20}$ aminoalkyl group optionally comprising one or more heterocyclic ring(s), or wherein $R^1$ and Y are interconnected so as to form an optionally substituted 4 to 8-membered ring, or wherein $R^1$ and $R^2$ are interconnected so as to form an optionally substituted 4 to 8-membered ring optionally comprising one or more heteroatoms;
$R^3$ is hydrogen, or is absent, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a thioalkoxy group, a thioalkyl group, a hydroxy group, a mercapto group, an allyl group, $C_1$-$C_{10}$ ether group, a vinyl group, a cyano group, a nitro group, a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^3$ and A are interconnected so as to form an optionally substituted 4 to 8-membered ring; or $R^3$ and Y are interconnected so as to form an optionally substituted 4 to 8-membered ring and
$R^4$ is absent, hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof, or wherein $R^3$ and $R^4$ are interconnected so as to form an optionally substituted 4 to 8-membered ring;

or wherein said compound is represented by Formula:

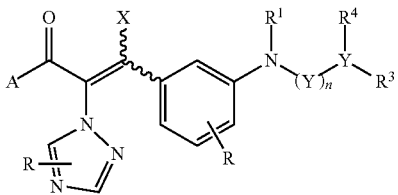

A represents a methyl group, isopropyl group, tert-butyl group, a linear or branched $C_1$-$C_{10}$ alkyl group, a linear or branched $C_2$-$C_{10}$ alkyl group substituted or not substituted, a substituted $C_2$-$C_{10}$ alkyl group, optionally substituted $C_3$-$C_{10}$ cycloalkyl group comprising one or more carbocyclic rings, an optionally substituted $C_2$-$C_{10}$ alkyl group comprising one or more heteroatom(s), a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof;

Y is selected from the group consisting of N, NH, $NR^1$, CH, $HCR^1$, CH2, S, SH, and 0;

n is an integer between 1 and 5;

X is hydrogen or represents a substituent selected from the group consisting of: a halo group, a methyl group, isopropyl group, $C_2$-$C_{10}$ alkyl group, a substituted $C_2$-$C_{10}$ alkyl group, an alkoxy group, an amino group, and a hydroxy group;

each R independently is absent or represents one or more substituents each independently comprising any one of a methyl group, isopropyl group, $C_2$-$C_{10}$ alkyl group, a substituted $C_2$-$C_{10}$ alkyl group, halo, oxo, —$NO_2$, amino, hydroxy, —CN, —OH, —$CONH_2$, —$CONR'_2$, —$CNNR'_2$, —$CSNR'_2$, —CONH—OH, —CONH—$NH_2$, —NHCOR, —NHCSR, —NHCNR, —NC(=O)OR, —NC(=O)NR', —NC(=S)OR', —NC(=S)NR', —$SO_2R'$, —SOR', —SR', —$SO_2OR'$, —$SO_2N(R')_2$, —$NHNR'_2$, —$NNR'_2$, $C_1$-$C_6$ haloalkyl, optionally substituted $C_1$-$C_6$ alkyl, —$NH_2$, —NR'R', —NH($C_1$-$C_6$ alkyl), —N($C_1$-$C_6$ alkyl)$_2$, $C_1$-$C_6$ alkoxy, $C_1$-$C_6$ haloalkoxy, hydroxy($C_1$-$C_6$ alkyl), hydroxy($C_1$-$C_6$ alkoxy), alkoxy($C_1$-$C_6$ alkyl), alkoxy($C_1$-$C_6$ alkoxy), $C_1$-$C_6$ alkyl-$NR'_2$, $C_1$-$C_6$ alkyl-SR', —CONH($C_1$-$C_6$ alkyl), —CON($C_1$-$C_6$ alkyl)$_2$, —$CO_2H$, —$CO_2R'$, —OCOR, —OCOR', —OC(=O)OR', —OC(=O) NR', —OC(=S)OR', —OC(=S)NR', —OR', —NR'R', or a combination thereof; wherein each R' independently represents hydrogen, or is selected from the group consisting of optionally substituted $C_1$-$C_{10}$ alkyl, optionally substituted $C_3$-$C_{10}$ cycloalkyl, optionally substituted $C_3$-$C_{10}$ heterocyclyl, optionally substituted heteroaryl, optionally substituted aryl, amino, hydroxy, halo, oxo, cyano, optionally substituted $C_1$-$C_{10}$ alkyl, or any combination thereof as allowed by valency;

$R^1$ is selected from the group consisting of hydrogen, oxygen, $C_1$-$C_{20}$ alkyl group, optionally substituted linear or branched $C_1$-$C_{20}$ aminoalkyl group, optionally substituted linear, branched or cyclic $C_1$-$C_{20}$ alkyl group optionally comprising one or more heteroatom(s), a substituted $C_1$-$C_{20}$ alkyl group, a $C_1$-$C_{20}$ haloalkyl group, a substituted $C_1$-$C_{20}$ haloalkyl group, and an aliphatic linear or branched $C_3$-$C_{20}$ aminoalkyl group optionally comprising one or more heterocyclic ring(s), or wherein $R^1$ and Y are interconnected so as to form an optionally substituted 4 to 8-membered ring;

$R^3$ is hydrogen, or is absent, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a thioalkoxy group, a thioalkyl group, a hydroxy group, a mercapto group, an allyl group, $C_1$-$C_{10}$ ether group, a vinyl group, a cyano group, a nitro group, a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, any combination thereof, or $R^3$ and A are interconnected so as to form an optionally substituted 4 to 8-membered ring; or $R^3$ and Y are interconnected so as to form an optionally substituted 4 to 8-membered ring and $R^4$ is absent, hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, a bicyclic aliphatic ring, or a combination thereof, or wherein $R^3$ and $R^4$ are interconnected so as to form an optionally substituted 4 to 8-membered ring.

2. The compound of claim 1, wherein said compound is represented by Formula IIa:

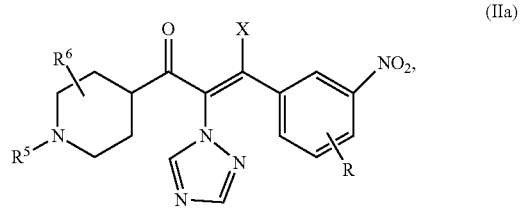

(IIa)

wherein:

$R^5$ and $R^6$ are each independently selected from the group consisting of hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring and, a bicyclic aliphatic ring, or any combination thereof, n is an integer ranging between 0 and 5; and $R^7$ and $R^8$ are each independently selected from the group consisting of hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, and a bicyclic aliphatic ring, or $R^7$ and $R^8$ are interconnected so as to form an optionally substituted 4 to 8-membered ring.

3. The compound of claim 1, wherein said compound is represented by Formula IIIa:

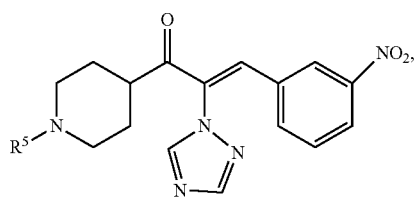

(IIIa)

or Formula IIIb:

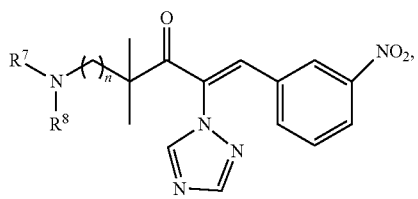

(IIIb)

wherein:

$R^7$ and $R^8$ are each independently selected from the group consisting of hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C^{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring, and a bicyclic aliphatic ring, or $R^7$ and $R^8$ are interconnected so as to form an optionally substituted 4 to 8-membered ring; and $R^5$ is selected from the group consisting of hydrogen, or represents a methyl group, isopropyl group, $C_2$-$C_{10}$ alkyl group, a substituted $C_2$-$C_{10}$ alkyl group, a $C_1$-$C_{10}$ haloalkyl group, a substituted $C_1$-$C_{10}$ haloalkyl group, a $C_1$-$C_{10}$ alkylhydroxy group, a halo group, a $C_1$-$C_{10}$ alkoxy group, an amino group, a hydroxy group, an allyl group, $C_1$-$C_{10}$ ether group, a vinyl group a $C_1$-$C_{10}$ alkylamino group, a $C_1$-$C_{10}$ alkylamide group, a $C_3$-$C_{10}$ cycloalkyl group, a substituted $C_3$-$C_{10}$ cycloalkyl, an heteroaryl, a substituted heteroaryl, an heterocyclyl, a substituted heterocyclyl, a bicyclic aromatic ring, an unsaturated aliphatic ring and a bicyclic aliphatic ring.

4. The compound of claim 1, wherein said compound is represented by Formula:

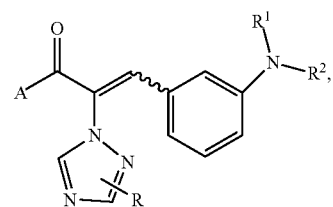

wherein A is selected from the group consisting of a methyl group, isopropyl group, tert-butyl group, a linear or branched $C_1$-$C_{10}$ alkyl group, optionally substituted $C_3$-$C_{10}$ cycloalkyl group comprising one or more carbocyclic rings, a linear or branched $C_2$-$C_{10}$ alkyl group, a linear or branched substituted $C_2$-$C_{10}$ alkyl group, $R^1$ and $R^2$ are each independently selected from the group consisting of comprising hydrogen, optionally substituted linear, branched or cyclic $C_1$-$C_{20}$ alkyl group optionally comprising one or more nitrogen atom(s); an optionally substituted $C_1$-$C_{20}$ alkyl group; an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; or wherein $R^1$ and $R^2$ are interconnected so as to form one or more 4 to 8-membered ring(s) optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; and wherein at least one of $R^1$ and $R^2$ is any one of branched or cyclic $C_1$-$C_{20}$ alkyl group comprising one or more nitrogen atom(s); an optionally substituted linear or branched $C_5$-$C_{20}$ alkyl-aminoalkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group.

5. The compound of any one of claim 1, wherein said compound is represented by Formula IVa:

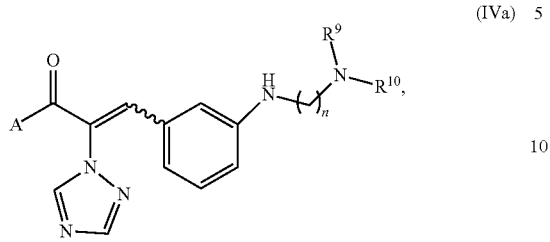

(IVa)

or Formula IVb:

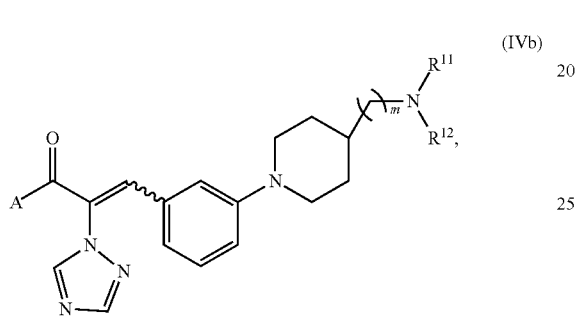

(IVb)

wherein:

R$^9$ and R$^{10}$ are each independently selected from the group consisting of hydrogen, or represents a methyl group, isopropyl group, C$_2$-C$_{10}$ alkyl group, a substituted C$_2$-C$_{10}$ alkyl group, a C$_1$-C$_{10}$ haloalkyl group, a substituted C$_1$-C$_{10}$ haloalkyl group, a C$_1$-C$_{10}$ alkylhydroxy group, a halo group, a C$_1$-C$_{10}$ alkoxy group, an amino group, a hydroxy group, an allyl group, C$_1$-C$_{10}$ ether group, a vinyl group a C$_1$-C$_{10}$ alkylamino group, a C$_1$-C$_{10}$ alkylamide group, a C$_3$-C$_{10}$ cycloalkyl group, a substituted C$_3$-C$_{10}$ cycloalkyl, an heteroaryl, a substituted heteroaryl, an heterocyclyl, a substituted heterocyclyl, a bicyclic aromatic ring, an unsaturated aliphatic ring, and a bicyclic aliphatic ring; or R$^9$ and R$^{10}$ are interconnected so as to form one or more optionally substituted 4 to 8-membered ring(s);

m is an integer ranging between 0 and 7; and

R$^{11}$ and R$^{12}$ are each independently selected from the group consisting of comprising hydrogen, or represents a methyl group, isopropyl group, C$_2$-C$_{10}$ alkyl group, a substituted C$_2$-C$_{10}$ alkyl group, a C$_1$-C$_{10}$ haloalkyl group, a substituted C$_1$-C$_{10}$ haloalkyl group, a C$_1$-C$_{10}$ alkylhydroxy group, a halo group, a C$_1$-C$_{10}$ alkoxy group, an amino group, a hydroxy group, an allyl group, C$_1$-C$_{10}$ ether group, a vinyl group, a C$_1$-C$_{10}$ alkylamino group, a C$_1$-C$_{10}$ alkylamide group, a C$_3$-C$_{10}$ cycloalkyl group, a substituted C$_3$-C$_{10}$ cycloalkyl, an heteroaryl, a substituted heteroaryl, an heterocyclyl, a substituted heterocyclyl, a bicyclic aromatic ring, an unsaturated aliphatic ring and a bicyclic aliphatic ring, or R$^{11}$ and R$^{12}$ are interconnected so as to form an optionally substituted 4 to 8-membered ring.

6. The compound of claim 1, wherein said compound is represented by Formula:

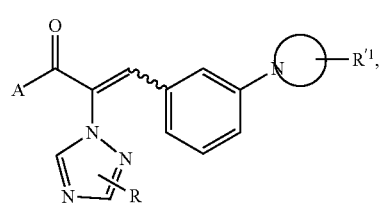

or by Formula:

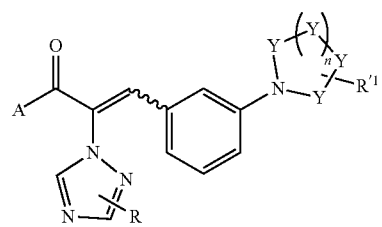

wherein n is 1-3; wherein each Y is independently CHR'$^1$ or NR'$^1$; and wherein R'$^1$ is absent or represents one or more substituents each independently selected from the group consisting of an optionally substituted linear, branched or cyclic C$_1$-C$_{20}$ alkyl group optionally comprising one or more nitrogen atom(s); an optionally substituted C$_1$-C$_{20}$ alkyl group; an optionally substituted linear or branched C$_5$-C$_{20}$ alkyl-aminoalkyl group; a linear, branched or cyclic C$_5$-C$_{20}$ aminoalkyl group comprising one or more nitrogen atoms and optionally substituted by one or more substituents independently selected from C$_1$-C$_{10}$ alkyl group, cyclic or non-cyclic C$_1$-C$_{10}$ alkylamino group, and cyclic or non-cyclic C1-C10 aminoalkyl group; halo, oxo, —NO$_2$, amino, hydroxy, —CN, —OH, —CONH$_2$, —CONR'$_2$, —CNNR'$_2$, —CSNR'$_2$, —CONH—OH, —CONH—NH$_2$, —NHCOR, —NHCSR, —NHCNR, —NC(=O)OR, —NC(=O)NR', —NC(=S)OR', —NC(=S)NR', —SO$_2$R', —SOR', —SR', —SO$_2$OR', —SO$_2$N(R')$_2$, —NHNR'$_2$, —NNR', C$_1$-C$_6$ haloalkyl, optionally substituted C$_1$-C$_6$ alkyl, —NH$_2$, —NR'R', —NH(C$_1$-C$_6$ alkyl), —N(C$_1$-C$_6$ alkyl)$_2$, C$_1$-C$_6$ alkoxy, C$_1$-C$_6$ haloalkoxy, hydroxy(C$_1$-C$_6$ alkyl), hydroxy(C$_1$-C$_6$ alkoxy), alkoxy(C$_1$-C$_6$ alkyl), alkoxy(C$_1$-C$_6$ alkoxy), C$_1$-C$_6$ alkyl-NR'$_2$, C$_1$-C$_6$ alkyl-SR', —CONH(C$_1$-C$_6$ alkyl), —CON(C$_1$-C$_6$ alkyl)$_2$, —CO$_2$H, —CO$_2$R', —OCOR, —OCOR', —OC(=O) OR', —OC(=O)NR', —OC(=S) OR', —OC(=S)NR', —OR', and —NR'R'; wherein each R' independently represents hydrogen, or is selected from the group consisting of optionally substituted C$_1$-C$_{10}$ alkyl, optionally substituted C$_3$-C$_{10}$ cycloalkyl, optionally substituted C$_3$-C$_{10}$ heterocyclyl, optionally substituted heteroaryl, optionally substituted aryl, amino, hydroxy, halo, oxo, cyano and optionally substituted C$_1$-C$_{10}$ alkyl.

7. The compound of claim 1, wherein A is tert-butyl; and wherein said compound is a Z-isomer.

8. The compound of claim 7, wherein said compound is represented by Formula:

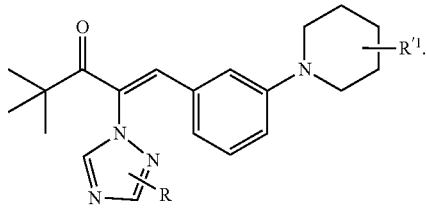
(Formula)

9. The compound of claim 8, wherein $R^{r1}$ is absent or represents one or more substituents each independently selected from the group comprising an optionally substituted cyclic $C_5$-$C_6$ aliphatic ring comprising one or more nitrogen atom(s); an optionally substituted linear, branched or cyclic $C_1$-$C_{20}$ alkyl group; a linear, branched or cyclic $C_5$-$C_{20}$ aminoalkyl group comprising one or more nitrogen atoms and optionally substituted by one or more substituents independently selected from $C_1$-$C_{10}$ alkyl group, cyclic or non-cyclic $C_1$-$C_{10}$ alkylamino group, and cyclic or non-cyclic $C_1$-$C_{10}$ aminoalkyl group; halo, oxo, —NO$_2$, amino, hydroxy, —CN, —OH, —CONH$_2$.

10. The compound of claim 9, wherein $R^{r1}$ is an optionally substituted cyclic $C_5$-$C_6$ aliphatic ring comprising one or more nitrogen atom(s); and wherein said optionally substituted cyclic $C_5$-$C_6$ aliphatic ring is bound via a nitrogen atom.

11. The compound of claim 1, wherein said compound is selected from the group consisting of:

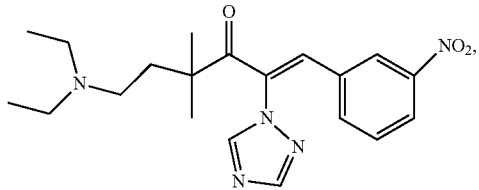
(T5)

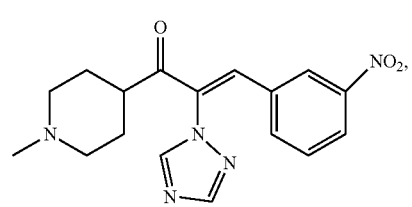
(T6)

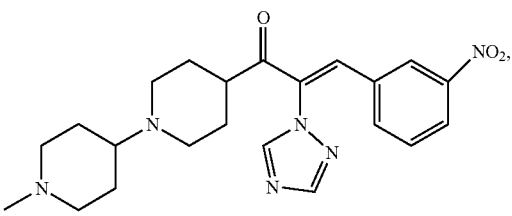
(T7)

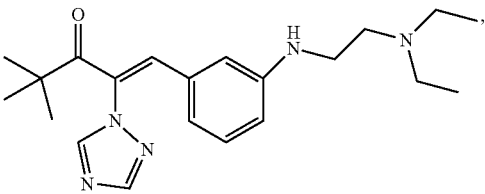
(T1)

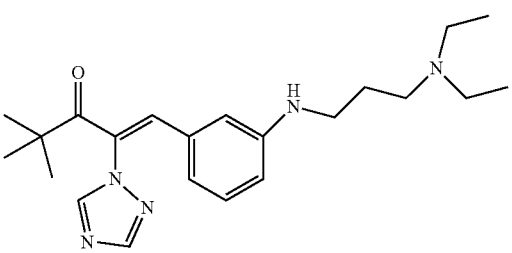
(T2)

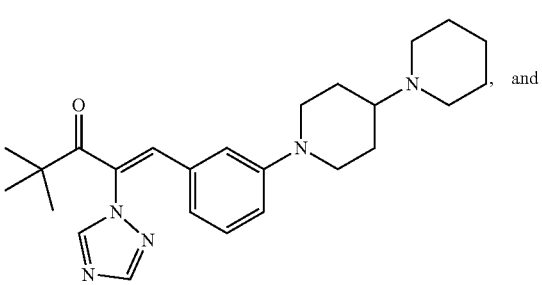
(T3), and

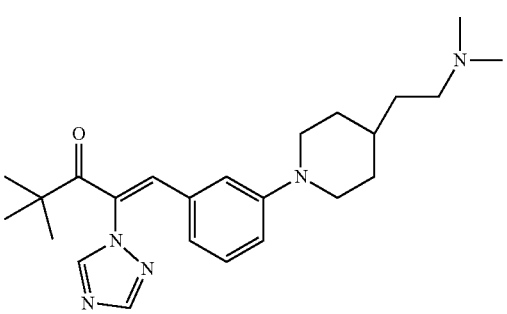
(T4)

including any cis-, or trans-isomer thereof.

12. The compound of claim 11, wherein said compound is T3.

13. A nanoparticle comprising a core and a shell, wherein the shell comprises a lipid layer, and the core comprises the compound of claim 1; wherein said lipid layer comprises, a phospholipid and a sterol; optionally wherein said nanoparticle is in a form of liposome or micelle.

14. The nanoparticle of claim 13, further comprising a peptide comprising an amino acid sequence selected from SEQ ID NO: 1-13.

15. The nanoparticle of claim 14, wherein said peptide is covalently conjugated to the outside of said shell.

16. A method of treating a neutrophil-associated disease or condition in a subject in need thereof, the method comprising administering to said subject a pharmaceutical composition comprising the nanoparticle of claim 13.

17. The method of claim 16, wherein said disease or condition is selected from the group consisting of: cancer, an inflammatory disease or condition and an inflammatory autoimmune disease or condition.

18. The method of claim 17, wherein said disease or condition is cancer.

19. The method of claim 17, wherein said inflammatory disease or condition is selected from COPD, IBD and peritonitis.

20. The method of claim 18, wherein said cancer is kidney cancer.

* * * * *